D (12) United States Patent
Ohmoto et al.

(10) Patent No.: US 7,833,995 B2
(45) Date of Patent: Nov. 16, 2010

(54) BLOOD FLOW PROMOTERS FOR CAUDA EQUINA TISSUES

(75) Inventors: Kazuyuki Ohmoto, Mishima-gun (JP); Akihiro Kinoshita, Mishima-gun (JP); Yoshihisa Kamanaka, Mishima-gun (JP); Hidekazu Matsuya, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 720 days.

(21) Appl. No.: 10/581,619

(22) PCT Filed: Dec. 2, 2004

(86) PCT No.: PCT/JP2004/017961

§ 371 (c)(1),
(2), (4) Date: Jan. 26, 2007

(87) PCT Pub. No.: WO2005/053707

PCT Pub. Date: Jun. 16, 2005

(65) Prior Publication Data

US 2007/0129327 A1    Jun. 7, 2007

(30) Foreign Application Priority Data

Dec. 5, 2003    (JP) ............................. 2003-407675

(51) Int. Cl.
*A01N 43/78*    (2006.01)
*A61K 31/425*    (2006.01)

(52) U.S. Cl. ...................................... 514/183; 514/365
(58) Field of Classification Search ........................ None
See application file for complete search history.

(56) References Cited

U.S. PATENT DOCUMENTS

| 6,288,119 | B1 | 9/2001 | Ohuchida |
| 2005/0020686 | A1 | 1/2005 | Maruyama et al. |
| 2005/0124577 | A1 | 6/2005 | Tani et al. |
| 2007/0129327 | A1 | 6/2007 | Ohmoto |
| 2009/0227644 | A1 | 9/2009 | Ohmoto et al. |

FOREIGN PATENT DOCUMENTS

| EP | 0 156 611 A2 | 10/1985 |
| EP | 1 481 976 A1 | 1/2004 |
| EP | 1 586 564 A1 | 10/2005 |
| EP | 1 609 480 A1 | 12/2005 |
| EP | 1 806 148 A1 | 11/2007 |
| JP | 11-130678 A | 5/1999 |
| WO | WO 03/009872 A1 | 2/2003 |
| WO | WO 03/074483 A1 | 9/2003 |
| WO | WO 2004/065365 A1 | 8/2004 |
| WO | 2004-089411 A1 | 10/2004 |
| WO | 2005-053707 A1 | 6/2005 |
| WO | 2005-061492 A1 | 7/2005 |
| WO | 2006-016689 A1 | 2/2006 |
| WO | 2006-043655 A1 | 4/2006 |

OTHER PUBLICATIONS

Y. Liu, "Rat Umao Shinkei Appaku Hoko Shogai Model Deno Beraprost Natrium to Limaprostal fadex Tono Hikaku", Basic Pharmacology & Therapeutics, 2002 pp. 875-880, vol. 30, No. 10.
M. Kiriyama, "Ligand binding specificities of the eight types and subtypes of the mouse prostanoid receptors expressed in Chinese hamster ovary cells", 1997, pp. 217-224, vol. 122, No. 2.
International Search Report for PCT/JP04/017961.
Bilak, M. et al., PGE2 Receptors Rescue Motor Neurons in a Model of Amyotrophic Lateral Sclerosis, Annals of Neurology, 2004, vol. 56, No. 2, pp. 240 to 248, full test, particularly, p. 243, left column, line 48 to p. 244, line 11, Fig 3., abstract, lines 1 to 3.
Supplementary European Search Report dated Feb. 12, 2010 in European Application No. 04819909.5.
Kato et al., "Successful Treatment of Intermittent Claudication Due to Spinal Canal Stenosis Using Beraprost Sodium, a Stable Prostaglandin I2 Analogue. A Case Report," The Journal of Vascular Diseases, vol. 48, No. 5, pp. 457-461 (1997).
Yone et al., "The effect of Lipo prostaglandin E1 on cauda equina blood flow in patients with lumbar spinal canal stenosis: myeloscopic observation," Spinal Cord, vol. 37, No. 4, pp. 269-274 (1999).
Konno et al., "Effects of OP-1206 (Prostaglandin E1) on Nerve-Conduction Velocity in the Dog Cauda Equina Subjected to Acute Experimental Compression," Journal of Spinal Disorders, vol. 9, No. 2, pp. 103-106 (1996).
Orendacova et al., "Cauda equina syndrome," Progress in Neurobiology, vol. 64, No. 6, pp. 613-637 (2001).
H. Kuwada, "Effects of prostaglandin derivatives on changes of gastric mucosal protein contents in ethanol-induced ulcer", Cytoprotection & Biology, 1985, pp. 217-225, vol. 3.
Kiyohiro Tsutsui, "Procylin Naifuku Toya go Soki Shita Livedo Kekkan'en no 1 Rei", The Journal of Medicine, 1994, pp. 611-613, vol. 32, No. 3.
Extended European Search Report for EP 06756919 dated Feb. 2, 2010 English.

*Primary Examiner*—Brandon J Fetterolf
*Assistant Examiner*—Craig Ricci
(74) *Attorney, Agent, or Firm*—Sughrue Mion, PLLC

(57) ABSTRACT

It is intended to provide highly safe and efficacious blood flow promoters for cauda equina tissues. Among prostaglandin-like compounds having a weak hypotensive effect, compounds having an effect of promoting the blood flow in cauda equina tissues (excluding limaprost) are useful as highly safe blood flow promoters for cauda equina tissues and, therefore, are efficacious in preventing and/or treating lumbar pain, lower limb pain, lower limb palsy, intermittent claudication, vesicorectal failure, hypogonadism, etc. caused by cauda equina injuries.

4 Claims, No Drawings

BLOOD FLOW PROMOTERS FOR CAUDA EQUINA TISSUES

TECHNICAL FIELD

The present invention relates to the agent to increase cauda equina blood flow having weak blood pressure-lowering effect.

BACKGROUND ART

Regarding the spinal canal, the front (abdomen side) is composed of the vertebral body and the interspinal disk, the lateral is composed of the pedicle, and the rear (back side) is composed of the intervertebral joint and the spinal process. The inside space surrounded by the elements of the front, the lateral and the rear is called the spinal canal. The spinal cord is present within the spinal canal, and is the cauda equina like a horse's tail under around the first lumbar vertebra. When the cauda equina is pressed by spinal canal stenosis or the like to thereby worsen blood circulation of a blood vessel which supplies nutrition to the cauda equina running through the spinal canal, disorders of nervous functions are caused to present symptoms such as lumbago, lower limb pain, lower limb numbness, intermittent claudication, bladder and rectal disorder, sexual dysfunction or the like.

On the one hand, prostaglandins (hereinafter, abbreviated as PG) has been known as a metabolite in the arachidonate cascade. It has been known that the action has cyto-protective activity, uterine contractive activity, a pain-inducing effect, a promoting effect on digestive peristalsis, an awakening effect, a suppressive effect on gastric acid secretion, hypotensive activity and diuretic activity and so on.

A recent study has proved existence of various PGE subtype receptors possessing a different physiological or pharmacological role from each other. At present, four receptor subtypes are known and they are called EP1, EP2, EP3, and EP4 (Negishi M., et al., *J. Lipid Mediators Cell Signaling*, 12, 379-391 (1995)).

It is described that a prostaglandin-like compound described in EP860430A1 has EP2 agonist action and is useful for prevention and/or treatment of immune diseases, asthma, abnormal bone formulation, neuron cell death, liver damage, abortion, premature birth or retinal neuropathy such as glaucoma etc. (Patent Reference 1).

It is described that a prostaglandin-like compound described in WO98/34916 has EP3 agonist action and is useful for prevention and/or treatment of liver diseases, Kidney disease, pancreatitis or myocardial infarction etc. (Patent Reference 2).

It is described that a prostaglandin-like compound described in WO2003/74483 has EP2 agonist action and is useful for prevention and/or treatment of immune diseases, allergic diseases, neuronal cell death, dysmenorrhea, premature birth, abortion, baldness, retinal neuropathy, erectile dysfunction, arthritis, pulmonary injury, pulmonary fibrosis, pulmonary emphysema, bronchitis, chronic obstructive pulmonary disease, hepatic injury, acute hepatitis, liver cirrhosis, shock nephritis, renal failure, circulatory diseases, systemic inflammatory response syndrome, sepsis, hemophagocytosis syndrome, macrophage activation syndrome, still disease, Kawasaki Disease, burn, systemic granuloma, ulcerative colitis, Crohn disease, hypercytokinemia at dialysis, multiple organ failure, or bone diseases etc. (Patent Reference 3).

However, it is neither described nor indicated that the prostaglandin-like compound increases cauda equina blood flow without the influence on blood pressure.

[Patent Reference 1] EP860430A1
[Patent Reference 2] WO98/34916
[Patent Reference 3] WO2003/74483

DISCLOSURE OF THE INVENTION

Problems to be Solved by the Invention

The safe and efficient agent to increase cauda equina blood flow for improving symptoms such as lumbago, lower limb pain, lower limb numbness, intermittent claudication, bladder and rectal disorder or sexual dysfunction due to cauda equina neurological disorder is desired.

Means for Solving the Problems

The present inventors studied eagerly, and as a result, found that a prostaglandin-like compound is useful as an agent to increase cauda equina blood flow and improves symptoms such as lumbago, lower limb pain, lower limb numbness, intermittent claudication, bladder and rectal disorder or sexual dysfunction. Also, the present inventors found that prostaglandin-like compounds having weak blood pressure-lowering effect have weak blood pressure-lowering effect as a side effect recognized by conventional prostaglandin-like compounds and are safe and excellent agents capable of increasing cauda equina blood flow. Thus, the present invention has been completed.

That is to say, the present invention relates to 1. an agent to increase cauda equina blood flow comprising a prostaglandin-like compound having weak blood press lowering effect (However, limaprost is excluded.), 2. the agent according to the above-described 1 wherein the prostaglandin-like compound is EP2 and/or EP3 agonist, 3. the agent according to the above-described 1 which improves one or more selected from lumbago, lower limb pain, lower limb numbness, intermittent claudication, bladder and rectal disorder and sexual dysfunction, 4. the agent according to the above-described 1 wherein the prostaglandin-like compound is a compound represented by formula (I)

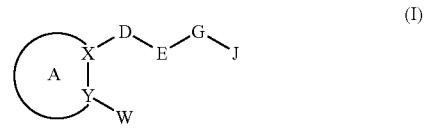

(wherein ring A is 5 or 6 membered ring which may comprise at least one hetero atom selected nitrogen, oxygen and sulfur, and may have a substituent(s), X and Y are each independently nitrogen or carbon, D is hydrocarbon group which may have a substituent(s), E is a bond, oxygen or optionally oxidized sulfur, G is a bond, hydrocarbon group which may have a substituent(s) or hetero ring which may have a substituent(s), J is acidic group which may be protected, W is hydrocarbon group which may have a substituent(s).), a salt thereof, an N-oxide thereof, a solvate thereof or prodrug thereof, or a cyclodextrin clathrate thereof, 5. the agent according to the above-described 4 wherein a compound represented by formula (I) is a compound represented by (I-1)

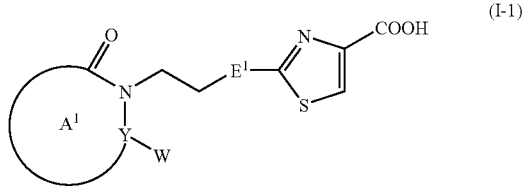

(wherein ring $A^1$ is 5 or 6 membered nitrogen-containing mono-heterocyclic ring may have a substituent(s), the ring $A^1$ may comprise, in addition, nitrogen, oxygen and/or sulfur, $E^1$ is optionally oxidized sulfur, Y is nitrogen or carbon, W is hydrocarbon group which may have a substituent(s).), 6. a medicament combined a prostaglandin-like compound having weak blood pressure-lowering effect (However, limaprost is excluded.) with one or more selected from prostaglandins, prostaglandin derivatives, nonsteroidal anti-inflammatory drugs, vitamins, muscle relaxants, antidepressants, nitric oxide synthase inhibitors, aldose reductase inhibitors, poly ADP-ribose polymerase inhibitors, excitatory amino acid receptor antagonists, radical scavengers, astrocyte modulators, phosphodiesterase inhibitor and immunosuppressive drugs, 7. a method for increasing cauda equina blood flow, which comprises administering to a mammal an effective amount of a prostaglandin-like compound having weak blood pressure-lowering effect (However, limaprost is excluded.), 8. use of a prostaglandin-like compound having weak blood pressure-lowering effect (However, limaprost is excluded.) for the manufacture of an agent to increase cauda equina blood flow, 9. a compound represented by formula (I-1)

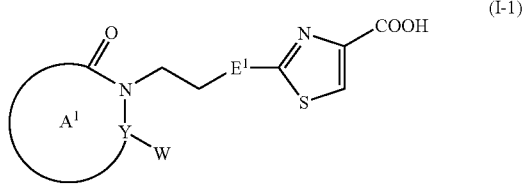

(wherein all symbols have same meanings as above-described 5), a salt thereof, an N-oxide thereof, a solvate thereof or prodrug thereof or a cyclodextrin clathrate thereof, 10. the compound according to the above-described 9 selected from 2-{[2-((4S)-4-{(1E,3R)-3-[1-(4-fluorobutyl)cyclobutyl]-3-hydroxy-1-propenyl}-2-oxo-1,3-oxazolidin-3-yl)ethyl]sulfanyl}-1,3-thiazole-4-carboxylic acid (compound 8-1), 2-[(2-{(4S)-4-[(1E,3R)-8-fluoro-3-hydroxy-4,4-dimethyl-1-octenyl]-2-oxo-1,3-oxazolidin-3-yl}ethyl)thio]-1,3-thiazole-4-carboxylic acid (compound 8-6), 2-{[2-((4S)-4{(1E,3R)-3-hydroxy-3-[1-(3-methoxypropyl)cyclobutyl]-1-propenyl}-2-oxo-1,3-oxazolidin-3-yl)ethyl]sulfanyl}-1,3-thiazole-4-carboxylic acid (compound 32-2), 2-{[2-((4S)-4-{(1E,3R)-3-[1-(2-cyclohexylethyl)cyclobutyl]-3-hydroxy-1-propenyl}-2-oxo-1,3-oxazolidin-3-yl)ethyl]sulfanyl}-1,3-thiazole-4-carboxylic acid (compound 32-14), 2-{[2-((4S,5S)-4-{(1E)-3-hydroxy-3-[1-(3-methoxypropyl)cyclobutyl]-1-propenyl}-5-methyl-2-oxo-1,3-oxazolidin-3-yl)ethyl]sulfanyl}-1,3-thiazole-4-carboxylic acid (compound 34-6) and 2-[(2-{(4S,5S)-4-[(1E)-4-hydroxy-4-methyl-1-nonenyl]-5-methyl-2-oxo-1,3-oxazolidin-3-yl}ethyl)sulfanyl]-1,3-thiazole-4-carboxylic acid (compound 45), 11. (2E)-7-{(1R,2R)-2-[(1E,3S,5S)-3-hydroxy-5-methyl-1-nonenyl]-5-oxocyclopentyl}-2-heptenoic acid (compound 24), (2E)-7-{(1R,2R,3R)-3-hydroxy-2-[(1E,3S,5S)-3-hydroxy-5-methyl-1-undecenyl]-5-oxocyclopentyl}-2-heptenoic acid (compound 25), (2E)-7-{(1R,2S)-2-[(1E,3S,5S)-3-hydroxy-5-methyl-1-nonenyl]-5-oxo-3-cyclopenten-1-yl}-2-heptenoic acid (compound 26), 2-[(2-{(1R,2R)-2-[(1E,3S,5S)-3-hydroxy-5-methyl-1-nonenyl]-5-oxocyclopentyl}ethyl)sulfanyl]-1,3-thiazole-4-carboxylic acid (compound 30), 2-[(2-{(1R,2R)-2-[(1E,3R)-3-hydroxy-4,4-dimethyl-1-octenyl]-5-oxocyclopentyl}ethyl)sulfanyl]-1,3-thiazole-4-carboxylic acid (compound 30-1), 7-{(1R,2R,3R)-3-hydroxy-2-[(1E,3S,5S)-3-hydroxy-5-methyl-1-nonenyl]-5-oxocyclopentyl}-6-oxoheptanoic acid (compound 31), 2-[(2-{(1R,2R)-2-[(1E)-5-cyclohexyl-4-hydroxy-4-methyl-1-pentenyl]-5-oxocyclopentyl}ethyl)sulfanyl]-1,3-thiazole-4-carboxylic acid (compound 53) or 3-{2-[((2R)-2-{(1E,3R)-3-[1-(4-fluorobutyl)cyclobutyl]-3-hydroxy-1-propenyl}-5-oxo-1-pyrrolidinyl)methyl]-1,3-thiazol-4-yl}propanoic acid (compound 76), a salt thereof an N-oxide thereof, a solvate thereof or prodrug thereof, or a cyclodextrin clathrate thereof.

Ring A in formula (I) may comprise at least one hetero atom selected from nitrogen, oxygen and sulfur. When X and/or Y in ring A is nitrogen, ring A may comprise one to three hetero atoms selected from nitrogen, oxygen and sulfur in addition to X and/or Y. The "5 or 6 membered ring" represented by "ring A" is, for example, "5 or 6 membered mono-carbocyclic ring" or "5 or 6 membered mono-heterocyclic ring" etc. The "5 or 6 membered mono-carbocyclic ring" includes, for example cyclopentane, cyclohexane, cyclopentene, cyclohexene, cyclopentadiene, cyclohexadiene or benzene ring etc. The "5 or 6 membered mono-heterocyclic ring" includes, for example pyrrole, imidazole, triazole, tetrazole, pyrazole, pyridine, pyrazine, pyrimidine, pyridazine, triazine, furan, thiophene, oxazole, isoxazole, thiazole, isothiazole, furazan, oxadiazole, thiadiazole, pyran, thiopyran, oxazine, oxadiazine, thiazine, thiadiazine, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, tetrahydrotriazine, dihydrofuran, dihydropyran, dihydrothiophene, dihydrothiopyran, dihydrooxazole, dihydroisoxazole, dihydrothiazole, dihydroisothiazole, dihydrofurazan, dihydrooxadiazole, dihydrooxazine, dihydrooxadiazine, dihydrothiadiazole, dihydrothiazine, dihydrothiadiazine, pyrrolidine, imidazolidine, triazolidine, tetrazolidine, pyrazolidine, piperidine, piperazine, perhydropyrimidine, perhydropyridazine, tetrahydrofuran, tetrahydropyran, perhydrooxepine, tetrahydrothiophene, tetrahydrothiopyran, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, tetrahydrothiadiazole (thiadiazolidine), tetrahydrothiazine, tetrahydrothiadiazine, morpholine, thiomorpholine, oxathiane or perhydrotriazine ring etc. 5 or 6 membered fused ring such as (1R,5S)-3-azabicyclo[3.1.0]hexane etc. is included in "5 or 6 membered ring". Preferred as ring A is cyclopentane, cyclopentene, pyrrolidine, imidazolidine, tetrahydrooxazole, tetrahydrothiazole or (1R,5S)-3-azabicyclo[3.1.0]hexane ring etc.

The "nitrogen-containing mono-heterocyclic ring" represented by ring $A^1$ in formula (I-1) may comprise, in addition, nitrogen, oxygen and/or sulfur. The ring $A^1$ is may comprise one to three nitrogen, oxygen and/or sulfur in addition to nitrogen and Y represented in ring $A^1$ of formula (I-1). The "5 or 6 membered nitrogen-containing mono-heterocyclic ring" includes, for example pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, tetrahydropyridazine, perhydropyridazine, dihydrooxazole, tetrahydrooxazole, dihydrothiazole, tetrahydrooxadiazole, dihydrooxazine, tetrahydrooxazine, dihydrooxadiazine, tetrahydrooxadiazine, dihydrothiazine, tetrahydrothiazine, dihydrothiadiazine, tetrahydrothiadiazine, morpholine, thiomorpholine, tetrahydrotriazine, tetrahydrothiadiazole or perhydrotriazine ring etc.

Preferred as ring $A^1$ is pyrrolidine, imidazolidine, tetrahydrooxazole or tetrahydrothiazole ring etc.

Ring A or ring $A^1$ may have a substituent(s). 1 to 5 substituents, preferably 1 to 3, may be substituted at replaceable positions. When the number of substituents is two or more, each substituent may be the same or different. When the number of substituents of ring A or ring $A^1$ is two or more, for example, two substituents of ring A taken together with atom of ring A may form ring (As for ring A1, it is similar). The formed ring includes C3-7 cycloalkyl (e.g. cyclopropyl, cyclobutyl, cyclopentyl, cyclohexyl, cyclopentyl etc.).

The substituent of ring A or ring $A^1$ includes, for example (1) hydrocarbon group which may have a substituent(s), (2) heterocyclic group which may have a substituent(s), (3) amino which may have a protecting group(s), (4) C1-4 alkylsulfonyl such as methylsulfonyl or ethylsulfonyl, (5) phenylsulfonyl, (6) halogen atom such as fluorine, chlorine, bromine or iodine, (7) carboxyl, (8) cyano, (9) nitro, (10) oxo, (11) thioxo, (12) hydroxy which may have a protecting group, (13) mercapto which may have a protecting group, (14) carbamoyl which may have a substituent(s), (15) sulfamoyl which may have a substituent(s), (16) alkoxycarbonyl (e.g. C1-6 alkoxycarbonyl such as methoxycarbonyl, ethoxycarbonyl, tert-butokycarbonyl), (17) sulfo (—$SO_3H$), (18) sulfino, (19) phosphono, (20) amidino, (21) imino, (22) —$B(OH)_2$ or (23) C1-6 acyl such as formyl, acetyl, propionyl or butylyl.

The "hydrocarbon group" in "(1) hydrocarbon group which may have a substituent(s)" as substituent of ring A or ring $A^1$ includes, for example straight or branched aliphatic hydrocarbon group; cyclic hydrocarbon group; C7-16 alalkyl such as benzyl or phenylethyl; (C3-8 cycloalkyl)-(C1-8 aliphatic hydrocarbon) group such as cyclohexylmethyl, cyclohexylethyl, cyclohexylpropyl, 1-methyl-1-cyclohexylmethyl, cyclobutylpropyl, cyclobutylpropenyl cyclobutylbutenyl cyclopentylpropyl or cyclopentylpropenyl etc. The "straight or branched aliphatic hydrocarbon group" includes, for example "C1-12 aliphatic hydrocarbon group". "C1-12 aliphatic hydrocarbon group" includes, for example C1-12 alkyl such as methyl, ethyl, propyl, isopropyl, butyl, sec-butyl, tert-butyl, pentyl, hexyl, heptyl, octyl, nonyl, decyl, undecyl or dodecyl; C2-12 alkenyl such as vinyl, propenyl, butenyl, pentenyl, hexenyl, heptenyl, octenyl, nonenyl, decenyl, undecenyl, dodecenyl, butadienyl, pentadienyl, hexadienyl, heptadienyl, octadienyl nonadienyl, decadienyl, undecadienyl, dodecadienyl, hexatrienyl, heptatrienyl, octatrienyl, nonatrienyl, decatrienyl, undecatrienyl or dodecatrienyl; C2-12 alkynyl such as ethynyl, propynyl, butynyl, pentynyl, hexynyl, heptynyl octynyl, nonynyl, decynyl, undecynyl dodecynyl, butadiynyl, pentadiynyl, hexadiynyl, heptadiynyl, octadiynyl, nonadiynyl decadiynyl, undecadiynyl dodecadiynyl, hexatriynyl, heptatriynyl, octatriynyl, nonatriynyl, decatriynyl, undecatriynyl or dodecatriynyl etc. The "cyclic hydrocarbon" includes "saturated cyclic hydrocarbon" or "unsaturated cyclic hydrocarbon". The "saturated cyclic hydrocarbon" includes, for example "3-15 membered saturated cyclic hydrocarbon" such as cycloalkane (e.g. cyclopropane, cyclobutane, cyclopentane, cyclohexane, cycloheptane, cyclooctane, cyclononane, cyclodecane, cycloundecane, cyclododecane, cyclotridecane, cyclotetradecane or cyclopentadecane), perhydropentalene, perhydroazulene, perhydroindene, perhydronaphthalene, perhydroheptalene, spiro[4.4]nonane, spiro[4.5]decane, spiro[5.5]undecane, bicyclo[2.2.1]heptane, bicyclo[3.1.1]heptane, bicyclo[2.2.2]octane, adamantane or noradamantane etc. The "unsaturated cyclic hydrocarbon" includes, for example "3-15 membered unsaturated cyclic hydrocarbon" such as cycloalkene (e.g. cyclopentene, cyclohexene, cycloheptene, cyclooctene, cyclopentadiene, cyclohexadiene, cycloheptadiene or cyclooctadiene), aromatic hydrocarbon (e.g. benzene, azulene, naphthalene phenanthrene or anthracene), pentalene, indene, indan, dihydronaphthalene, tetrahydronaphthalene, heptalene, biphenylene, as-indacene, s-indacene, acenaphthene, acenaphthylene, fluorene, phenalene, bicyclo[2.2.1]hept-2-ene, bicyclo[3.1.1]hept-2-ene or bicyclo[2.2.2]oct-2-ene etc.

The "substitutent" in "hydrocarbon group which may have a substituent(s)" as substituent of ring A or ring $A^1$ includes (1) hydrocarbon group (the "hydrocarbon group" has a same meaning as the above-described "hydrocarbon group".) which may have a substituent(s) (e.g. amino, sulfo, halogen atom (fluorine, chlorine, bromine, iodine etc.; Hereafter, the halogen atom is similar), carboxy, cyano, nitro, oxo, thioxo, hydroxy, C1-8, alkoxy (e.g. methoxy, ethoxy, propoxy, isopropoxy, butoxy, isobutoxy, sec-butoxy, tert-butoxy, cyclohexylmethyloxy, benzyloxy etc), trifluoromethyl, trifluoromethoxy etc.), (2) heterocyclic ring (the "heterocyclic ring" has the same meaning as the above-described "heterocyclic ring" as substituent of ring A or ring $A^1$.") which may have a substituent(s) (e.g. hydrocarbon group (the "hydrocarbon group" has a same meaning as the above-described "hydrocarbon group".), amino, sulfo, halogen atom, carboxy, cyano, nitro, oxo, thioxo, hydroxy, methoxy, trifluoromethyl, trifluoromethoxy, acetyl etc.), (3) amino, (4) C1-6 acylamino such as acetylamino or propionylamino, (5) primary or secondary amino substituted by hydrocarbon such as methylamino, ethylamino, propylamino, isopropylamino, butylamino, dimethylamino, diethylamino, cyclohexylamino, 1-carbamoyl-2-cyclohexylethylamino, N-butyl-N-cyclohexylmethylamino, phenylamino or butoxyphenylamino (the "hydrocarbon group" has a same meaning as the above-described "hydrocarbon group" and may be substituted by C1-4 alkoxy (e.g. methoxy, ethoxy, propoxy, isopropoxy, butoxy, isobutoxy, sec-butoxy, tert-butoxy), oxo, amino, carbamoyl etc., (6) C1-4 alkylsulfonylamino such as methylsulfonylamino or ethylsulfonylamino, (7) phenylsulfonylamino, (8) C1-4 alkylsulfonyl such as methylsulfonyl or ethylsulfonyl, (9) phenylsulfonyl, (10) halogen atom (e.g. fluorine, chlorine, bromine, iodine), (11) carboxy, (12) cyano, (13) nitro, (14) oxo, (15) thioxo, (16) hydroxy, (17) C1-8 alkoxy such as methoxy, ethoxy, propoxy, isopropoxy, butoxy, isobutoxy, sec-butoxy, tert-butoxy, cyclohexylmethyloxy or benzyloxy (the alkoxy may be substituted by halogen atom etc.), (18)

C3-8 cycloalkoxy such as cyclohexyloxy (the C3-8 cycloalkoxy may be substituted by halogen atom etc.), (19) phenoxy which may be substituted by methyl or halogen atom etc., (20) mercapto, (21) C1-4 alkylthio such as methylthio, ethylthio, propylthio, isopropylthio, butylthio or tert-butylthio, (22) phenylthio, (23) carbamoyl, (24) aminocarbonyl substituted by C1-8 hydrocarbon group such as N-butylaminocarbonyl, N-cyclohexylmethylaminocarbonyl, N-butyl-N-cyclohexylmethylaminocarbonyl, N-cyclohexylaminocarbonyl or phenylaminocarbonyl (the "hydrocarbon group" has a same meaning as the above-described "hydrocarbon group".), (25) sulfamoyl, (26) aminosulfonyl substituted by hydrocarbon group such as methylaminosulfonyl (the "hydrocarbon group" has a same meanings as the above-described "hydrocarbon group".), (27) aminosulfonyl which is substituted by hydrocarbon group substituted by amino such as dimethylaminoethylaminosulfonyl or dimethylaminoethylaminosulfonyl (the "hydrocarbon group" has a same meaning as the above-described "hydrocarbon group".), (28) C1-6 alkoxycarbonyl such as methoxycarbonyl, ethoxycarbonyl or tert-butoxycarbonyl, (29) sulfo ($-SO_3H$), (30) sulfino, (31) phosphono, (32) amidino, (33) imino, (34) $-B(OH)_2$, (35) C1-4 alkylsulfonyl such as methylsulfinyl or ethylsulfinyl, (36) C1-6 acyl such as formyl, acetyl, propionyl or butylyl, (37) benzoyl, (38) hydroxyimino or (39) alkyloxyimino such as methyloxyimino or ethyloxyimino etc. The "hydrocarbon which may have a substituent(s)" may have 1 to 5 substituents selected from the above-described (1) to (39). When the number of substituents is two or more, each substituent may be the same or different. Moreover, two substituents taken together with carbon atom on hydrocarbon group may form ring.

The "heterocyclic ring" in the "(2) heterocyclic ring which may have a substituent(s)" as the substituent of ring A or ring $A^1$ is mono-, bi- or tri-heterocyclic ring which may comprise one to seven hetero arom(s) selected from nitrogen, oxygen or sulfur. The "heterocyclic ring" includes for example "3 to 15 membered unsaturated mono-, bi- or tri-heterocyclic ring" or "3 to 15 membered saturated mono-, bi- or tri-heterocyclic ring".

The "3 to 15 membered unsaturated mono-, bi- or tri-heterocyclic ring" includes, for example mono-heteroaromatic ring such as pyrrole, imidazole, triazole, tetrazole, pyrazole, pyridine, pyrazine, pyrimidine, pyridazine, triazine, furan, thiophene, oxazole, isoxazole, thiazole, isothiazole, furazan, oxadiazole or thiadiazole ring; fused heteroaromatic ring such as indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazan, benzothiadiazole, benzotriazole, carbazole, β-carboline, acridine, phenazine, dibenzofuran, dibenzothiophene, phenanthridine, phenanthroline or pyrimidine ring; non-aromatic unsaturated heterocyclic ring such as azepine, diazepine, pyran, oxepine, thiopyran, thiepine, oxazine, oxadiazine, oxazepine, oxadiazepine, thiazine, thiadiazine, thiazepine, thiadiazepine, indolizine, dithianaphthalene, quinolizine, chromene, benzoxepine, benzoxazepine, benzoxadiazepine, benzothiepine, benzothiazepine, benzothiadiazepine, benzazepine, benzodiazepine, xanthene, phenothiazine, phenoxazine, phenoxathiin, thianthrene, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, tetrahydrotriazine, dihydroazepine, tetrahydroazepine, dihydrodiazepine, tetrahydrodiazepine, dihydrofuran, dihydropyran, dihydrooxepine, tetrahydrooxepine, dihydrothiophene, dihydrothiopyran, dihydrothiepine, tetrahydrothiepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, tetrahydrothiazepine, dihydrothiadiazepine, tetrahydrothiadiazepine, indoline, isoindoline, dihydrobenzofuran, dihydroisobenzofuran, dihydrobenzothiophene, dihydroisobenzothiophene, dihydroindazole, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, benzoxathiane, dihydrobenzoxazine, dihydrobenzothiazine, pyrazinomorpholine, dihydrobenzoxazole, dihydrobenzothiazole, dihydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, dihydro-β-carboline, tetrahydro-β-carboline, dihydroacridine, tetrahydroacridine, dihydrodibenzofuran, dihydrodibenzothiophene, tetrahydrodibenzofuran, tetrahydrodibenzothiophene, dioxaindan, benzodioxane, chroman, benzodithiolane, benzodithiane, 6,7,8,9-tetrahydro-5H-pyrido[4',3':4,5]pyrrolo[2,3-b]pyridine, 2,3,4,5-tetrahydro-1H-pyrido[4,3-b]indole or 6,7,8,9-tetrahydro-5H-pyrido[3',4':4,5]pyrrolo[2,3-b]pyridine ring etc. The "3 to 15 membered saturated mono-, bi- or tri-heterocyclic ring" includes, for example aziridine, azetidine, pyrrolidine, imidazolidine, triazolidine, tetrazolidine, pyrazolidine, piperidine, piperazine, perhydropyrimidine, perhydropyridazine, perhydroazepine, perhydrodiazepine, perhydroazocine, oxirane, oxetane, tetrahydrofuran, tetrahydropyran, perhydrooxepine, thiirane, thietane, tetrahydrothiophene, tetrahydrothiopyran, perhydrothiepine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepine, morpholine, thiomorpholine, oxathiane, perhydrobenzofuran, perhydroisobenzofuran, perhydrobenzothiophene, perhydroisobenzothiophene, perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole, perhydrocarbazole, perhydro-β-carboline, perhydroacridine, perhydrodibenzofuran, perhydrodibenzothiophene, dioxolane, dioxane, dithiolane or dithianering etc.

The "substituent" in the "(2) heterocyclic ring which may have a substituent(s)" as the substituent of ring A or ring $A^1$ includes, for example hydrocarbon group (the "hydrocarbon group" has a same meaning as the above-described "hydrocarbon group".), amino, sulfo, halogen atom, carboxy, cyano, nitro, oxo, thioxo, hydroxy, methoxy, trifluoromethyl, trifluoromethoxy or acetyl etc. The "(2) heterocyclic ring which may have a substituent(s)" may have one to five substituent(s) selected from described above. When the number of substituents is two or more, each substituent may be the same or different.

The "protecting group" in the "(3) amino which may have a protecting group(s)" as the substituent of ring A or ring $A^1$ includes, for example hydrocarbon group which may have a substituent(s), sulfo or sulfonyl bound to hydrocarbon group. The "hydrocarbon group which may have a substituent(s)" has a same meaning as the above-described "(1) hydrocarbon group which may have a substituent(s)" as the substituent of ring A or ring $A^1$.

The "protecting group" in the "(12) hydroxy which may have a protecting group" or the "(13) mercapto which may have a protecting group" as the substituent of ring A or ring $A^1$ includes, for example hydrocarbon group which may have a substituent(s). The "hydrocarbon group which may have a substituent(s)" has a same meaning as the above-described "(1) hydrocarbon group which may have a substituent(s)" as the substituent of ring A or ring $A^1$.

The "substituent" in the "(14) carbamoyl which may have a substituent(s)" or the "(15) sulfamoyl which may have a substituent(s)" as the substituent of ring A or ring $A^1$ includes, for example hydrocarbon group which may have a substituent(s). The "hydrocarbon group which may have a substituent(s)" has a same meaning as the above-described "(1) hydrocarbon group which may have a substituent(s)" as the substituent of ring A or ring $A^1$.

Preferred as substituent of ring A or ring $A^1$ is C1-4 alkyl such as methyl, ethyl, propyl or butyl, oxo, hydroxy or halogen arom etc.

The "hydrocarbon group" in the "hydrocarbon group may have a substituent(s)" represented by D or G includes, for example a divalent straight or branched aliphatic hydrocarbon group etc. The "straight or branched aliphatic hydrocarbon group" includes, for example "C1-8 aliphatic hydrocarbon group" etc. The "C1-8 aliphatic hydrocarbon group" includes, for example C1-8 alkylene such as methylene, ethylene, propylene, isopropylene, butylene, sec-butylene, tert-butylene, pentylene, hexylene, heptylene or octylene; C2-8 alkenylene such as vinylene, propenylene, butenylene, pentenylene, hexenylene, heptenylene, octenylene, butadienylene, pentadienylene, hexadienylene, heptadienylene, ocatadienylene, hexatrienylene, heptatrienylene or octatrienylene; C2-8 alkynylene such as ethynylene, propynylene, butynylene, pentynylene, hexynylene, heptynylene, octynylene, butadiynylene, pentadiynylene, hexadiynylene, heptadiynylene, octadiynylene, hexatriynylene, heptatriynylene or octatriynylene etc. The "hydrocarbon group" may substituted by "(1) hydrocarbon group which may have a substituent(s)" as the substituent of ring A or ring $A^1$.

Preferred as D is, for example C1-6 alkylene or C2-6 alkylene etc.

The "heterocyclic ring" represented by G has a same meaning as the above-described "heterocyclic ring" as the substituent of ring A or ring $A^1$. Preferred is, for example

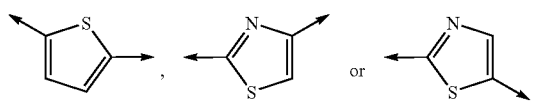

(wherein the arrow is a binding part of E to J.) etc.

The "optionally oxidized sulfur" represented by E includes, for example —S—, —SO— or —$SO_2$—. Preferred as E is optionally oxidized sulfur and more preferred is —S— or —$SO_2$—.

The "acidic group which may be protected" represented by J represents the "acidic group" which may be protected by a "protecting group". Examples of the "acidic group" include carboxy (—COOH), sulfo (—$SO_3H$), sulfino (—$SO_2H$), sulfonamide (—$SO_2NH_2$ or —$NR^{101}SO_3H$ ($R^{101}$ is hydrogen atom or hydrocarbon group which may have a substituent(s).)), phosphono (—$PO(OH)_2$), phenol (—$C_6H_4OH$) or various types of Brφnsted acid such as a nitrogen-containing ring residue having hydrogen from which can be removed as proton. The "Brφnsted acid" means a substance which gives hydrogen ion to other substance. Examples of the "nitrogen-containing ring residue having hydrogen from which can be removed as proton" include:

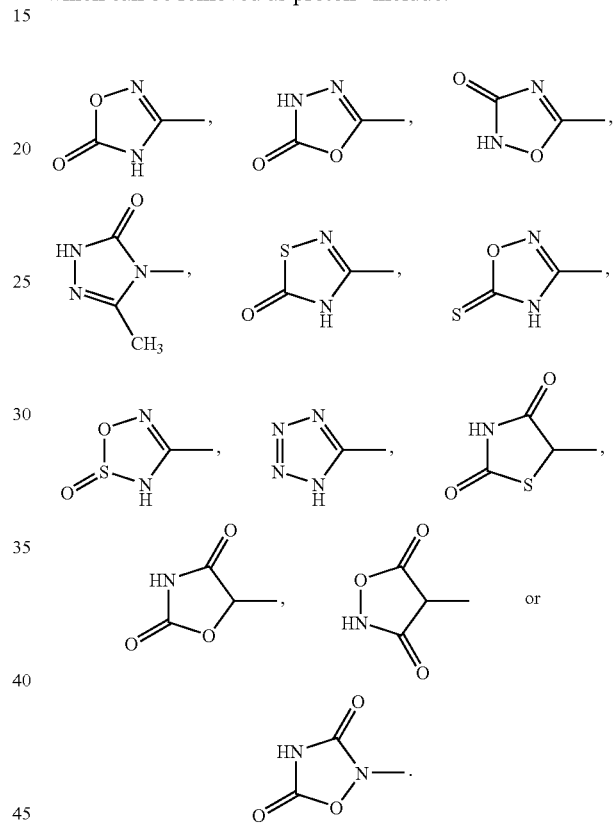

Preferred as "acidic group" is carboxy.

The "protecting group" includes hydrocarbon group which may have a substituent(s), C1-6 alkoxy or amino which may have a protecting group(s) etc. Preferred as the protecting group is methyl, ethyl, propyl, isopropyl, butyl or tert-butyl etc.

The "hydrocarbon group which may have a substituent(s)" represented by W has a same meaning as the above-described "(1) hydrocarbon group which may have a substituent(s)" as the substituent of ring A or ring $A^1$.

Preferred as W is

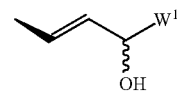

(wherein W¹ is hydrocarbon group which may have a substituent(s).) or

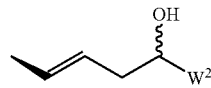

(wherein W² is hydrocarbon group which may have a substituent(s).).

In the specification, the compound having "weak blood pressure-lowing effect" is a compound in which about 20 mmHg or more, preferably 10 mmHg or more, of blood pressure is not lowered at dose that increases significantly cauda equina blood flow.

In the specification, the "prostaglandin-like compound" includes, for example C20 mono-carboxylic acid (prostanoic acid), i.e. a compound of basic skeleton represented by

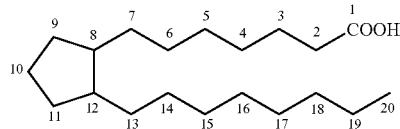

The "prostaglandin-like compound" includes, for example a unsaturated fatty acid of the above-described basic skeleton having double bond or hydroxy; a compound from which carbon atom at 8th or 12th position etc. is converted into nitrogen; a compound from which carbon atom at 5th or 10th position etc. is converted into oxygen or optionally oxidized sulfur; or a compound having a substituent(s) such as oxo, hydroxy or hydrocarbon at optional position (the substituent is optional and two substituents taken together with an atom on the basic skeleton may form ring). Moreover, a compound has prostaglandin-like action; a compound which has an action stimulating synthesis of prostaglandin or an action inhibiting degradation of prostaglandin; or a compound which has an action inhibiting synthesis of prostaglandin or an action stimulating degradation of prostaglandin are included. The prostaglandin-like compound includes, for example compounds described in EP860430A1, WO99/33794, EP974580A1, WO2003/74483, WO95/19964, U.S. Pat. No. 5,698,598, U.S. Pat. No. 6,376,533, WO98/28264, WO99/19300, EP0911321A1 or WO98/58911, and AH-13205, CP-533536, Butaprost, Rioprostil, Misoprostol, AY23626, in addition, compounds described in WO98/34916, JP7-215929, JP-239356, WO97/05091, JP07-233145, JP10-168056, JP11-012249 or WO99/25358, and TEI-3356, M&B-28767, GR63799X, SC-46275, Enprostil, Sulprostone, compounds described in EP855389A1, WO99/02164, WO2000/03980, U.S. Pat. No. 6,043,275, WO2000/15608, WO2000/54808, EP1110949A1, WO2001/37877, WO2001/49661, WO2001/66518, WO2002/24647, WO2002/42268, WO2003/007941, WO2003/008377, WO2003/009872, WO2003/035064, WO2003/053923 or U.S. Pat. No. 6,552,067 etc.

Moreover, for example a compound represented by formula (I)

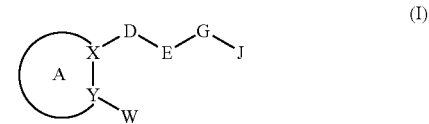

(wherein all symbols have same meanings as described above.) is included. Preferred is a compound represented by formula (I-1)

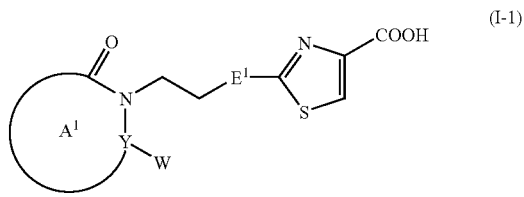

(wherein all symbols have same meanings as described above.).

More preferred as prostaglandin-like compound is compounds described in Example. Specifically preferred compound described in Example is 2-{[2-((4S)-4-{(1E,3R)-3-[1-(4-fluorobutyl)cyclobutyl]-3-hydroxy-1-propenyl}-2-oxo-1,3-oxazolidin-3-yl)ethyl]sulfanyl}-1,3-thiazole-4-carboxylic acid (compound 8-1), 2-[(2-{(4S)-4-[(1E,3R)-8-fluoro-3-hydroxy-4,4-dimethyl-1-octenyl]-2-oxo-1,3-oxazolidin-3-yl}ethyl)thio]-1,3-thiazole-4-carboxylic acid (compound 8-6), (2E)-7-{(1R,2R)-2-[(1E,3S,5S)-3-hydroxy-5-methyl-1-nonenyl]-5-oxocyclopentyl}-2-heptanoic acid (compound 24), (2E)-7-{(1R,2R,3R)-3-hydroxy-2-[(1E,3S,5S)-3-hydroxy-5-methyl-1-undecenyl]-5-oxocyclopentyl}-2-heptanoic acid (compound 25), (2E)-7-{(1R,2S)-2-[(1E,3S,5S)-3-hydroxy-5-methyl-1-nonenyl]-5-oxo-3-cyclopentene-1-yl}-2-heptanoic acid (compound 26), 2-{[2-((4S)-4-{(1E,3R)-3-hydroxy-3-[1-(3-methoxypropyl)cyclobutyl]-1-propenyl}-2-oxo-1,3-oxazolidin-3-yl)ethyl]sulfanyl}-1,3-thiazole-4-carboxylic acid (compound 32-2), 2-{[2-((4S)-4-{(1E,3R)-3-[1-(2-cyclohexylethyl)cyclobutyl]-3-hydroxy-1-propenyl}-2-oxo-1,3-oxazolidin-3-yl)ethyl]sulfanyl}-1,3-thiazole-4-carboxylic acid (compound 32-14), 2-{[2-((4S,5S)-4-{(1E)-3-hydroxy-3-[1-(3-methoxypropyl)cyclobutyl]-1-propenyl}-5-methyl-2-oxo-1,3-oxazolidin-3-yl)ethyl]sulfanyl}-1,3-thiazole-4-carboxylic acid (compound 34-6), 2-[(2-{(4S,5S)-4-[(1E)-4-hydroxy-4-methyl-1-nonenyl]-5-methyl-2-oxo-1,3-oxazolidin-3-yl}ethyl)sulfanyl]-1,3-thiazole-4-carboxylic acid (compound 45), 2-[(2-{(1R,2R)-2-[(1E)-5-cyclohexyl-4-hydroxy-4-methyl-1-pentenyl]-5-oxocyclopentyl}ethyl)sulfanyl]-1,3-thiazole-4-carboxylic acid (compound 53), 2-[(2-{(4S)-4-[(1E,3R)-3-hydroxy-4,4-dimethyl-1-octenyl]-2-oxo-1,3-oxazolidin-3-yl}ethyl)sulfanyl]-1,3-thiazole-4-carboxylic acid (compound 8), 2-[(2-{(4S)-4-[(1E,3S,5S)-3-hydroxy-5-methyl-1-nonenyl]-2-oxo-1,3-oxazolidin-3-yl}ethyl)sulfanyl]-1,3-thiazole-4-carboxylic acid (compound 8-3), 2-{[2-((2R)-2-{(1E,3R)-3-[1-(4-fluorobutyl)cyclobutyl]-3-hydroxy-1-propenyl}-5-oxo-1-pyrrolidinyl)ethyl]sulfanyl}-1,3-thiazole-4-carboxylic acid (compound 9-6), 2-[(2-{(1R,2R)-

2-[(1E,3S,5S)-3-hydroxy-5-methyl-1-nonenyl]-5-oxocyclopentyl}ethyl)sulfanyl]-1,3-thiazole-4-carboxylic acid (compound 30), 2-[(2-{(1R,2R)-2-[(1E,3R)-3-hydroxy-4,4-dimethyl-1-octenyl]-5-oxocyclopentyl}ethyl)sulfanyl]-1,3-thiazole-4-carboxylic acid (compound 30-1), 7-{(1R,2R,3R)-3-hydroxy-2-[(1E,3S,5S)-3-hydroxy-5-methyl-1-nonenyl]-5-oxocyclopentyl}-6-oxoheptanoic acid (compound 31), 2-[(2-{(4S)-4-[(1E,3R)-3-(1-butylcyclobutyl)-3-hydroxy-1-propenyl]-2-oxo-1,3-oxazolidin-3-yl}ethyl)sulfanyl]-1,3-thiazole-4-carboxylic acid (compound 32-1), 2-{[2-((4S)-4-{(1E,3R)-3-hydroxy-3-[1-(2-phenylethyl)cyclobutyl]-1-propenyl}-2-oxo-1,3-oxazolidin-3-yl)ethyl]sulfanyl}-1,3-thiazole-4-carboxylic acid (compound 32-4), 2-{[2-((4S)-4-{(1E)-3-[1-(2-ethoxyethyl)cyclobutyl]-3-hydroxy-1-propenyl}-2-oxo-1,3-oxazolidin-3-yl)ethyl]sulfanyl}-1,3-thiazole-4-carboxylic acid (compound 32-5), 2-{[2-((4S)-4-{(1E,3R)-3-hydroxy-3-[1-(2-methoxyethyl)cyclobutyl]-1-propenyl}-2-oxo-1,3-oxazolidin-3-yl)ethyl]sulfanyl}-1,3-thiazole-4-carboxylic acid (compound 32-10), 2-{[2-(4S)-4-{(1E,3R)-3-hydroxy-3-[1-(4-methylpentyl)cyclobutyl]-1-propenyl}-2-oxo-1,3-oxazolidin-3-yl)ethyl]sulfanyl}-1,3-thiazole-4-carboxylic acid (compound 32-11), 2-{[2-((4S)-4-{(1E,3R)-3-[1-(5-fluoropentyl)cyclobutyl]-3-hydroxy-1-propenyl}-2-oxo-1,3-oxazolidin-3-yl)ethyl]sulfanyl}-1,3-thiazole-4-carboxylic acid (compound 32-17), 2-[(2-{(2R)-2-[(1E)-3-hydroxy-4-(2-methylphenoxy)-1-butenyl]-5-oxo-1-pyrrolidinyl}ethyl)sulfanyl]-1,3-thiazole-4-carboxylic acid (compound 33-3), 2-[(2-{(4S,5S)-4-[(1E)-3-hydroxy-7-methoxy-4,4-dimethyl-1-heptenyl]-5-methyl-2-oxo-1,3-oxazolidin-3-yl}ethyl)sulfanyl]-1,3-thiazole-4-carboxylic acid (compound 34-7), 2-{[2-((4S,5S)-4-{(1E)-3-hydroxy-3-[1-(4-methoxybenzyl)cyclobutyl]-1-propenyl}-5-methyl-2-oxo-1,3-oxazolidin-3-yl)ethyl]sulfanyl}-1,3-thiazole-4-carboxylic acid (compound 34-10), 2-{[2-((4S,5S)-4-{(1E)-3-hydroxy-3-[1-(3-methoxypropyl)cyclopentyl]-1-propenyl}-5-methyl-2-oxo-1,3-oxazolidin-3-yl)ethyl]sulfanyl}-1,3-thiazole-4-carboxylic acid (compound 34-12), 2-{[2-((4S,5S)-4-{(1E,3R)-3-hydroxy-3-[1-(3-methoxypropyl)cyclobutyl]-1-propenyl}-5-methyl-2-oxo-1,3-oxazolidin-3-yl)ethyl]sulfanyl}-1,3-thiazole-4-carboxylic acid (compound 34-13), 2-{[2-((4S,5S)-4-{(1E)-3-hydroxy-3-[1-(4-methyl-3-pentenyl)cyclobutyl]-1-propenyl}-5-methyl-2-oxo-1,3-oxazolidin-3-yl)ethyl]sulfanyl}-1,3-thiazole-4-carboxylic acid (compound 34-14), 2-[(2-{(4S)-4-[(1E)-4-hydroxy-4-methyl-1-nonenyl]-2-oxo-1,3-oxazolidin-3-yl}ethyl)sulfanyl]-1,3-thiazole-4-carboxylic acid (compound 45-2), 2-[(2-{(4S)-4-[(1E)-5-cyclohexyl-4-hydroxy-4-methyl-1-pentenyl]-2-oxo-1,3-oxazolidin-3-yl}ethyl)sulfanyl]-1,3-thiazole-4-carboxylic acid (compound 45-3), 2-[(2-{(4S)-2-oxo-4-[(1E)-8,8,8-trifluoro-4-hydroxy-4-methyl-1-octenyl]-1,3-oxazolidin-3-yl}ethyl)sulfanyl]-1,3-thiazole-4-carboxylic acid (compound 45-4), 2-(2-{(4S,5S)-4-[4-hydroxy-7-methoxy-4-methyl-1-heptenyl]-5-methyl-2-oxo-1,3-oxazolidin-3-yl}ethyl)sulfanyl]-1,3-thiazole-4-carboxylic acid (compound 45-6), 2-[(2-{(4S,5S)-4-[(1E)-4-hydroxy-4-methyl-1-octenyl]-5-methyl-2-oxo-1,3-oxazolidin-3-yl}ethyl)sulfanyl]-1,3-thiazole-4-carboxylic acid (compound 45-7), 2-[(2-{(4S,5S)-4-[(1E)-4-hydroxy-4-methyl-1-decenyl]-5-methyl-2-oxo-1,3-oxazolidin-3-yl}ethyl)sulfanyl]-1,3-thiazole-4-carboxylic acid (compound 45-8), 2-[(2-{(4S,5S)-4-[(1E)-4-hydroxy-4-methyl-1-pentenyl]-5-methyl-2-oxo-1,3-oxazolidin-3-yl}ethyl)sulfanyl]-1,3-thiazole-4-carboxylic acid (compound 45-12), 2-[(2-{(4S,5S)-4-[1E)-10-fluoro-4-hydroxy-4-methyl-1-decenyl]-5-methyl-2-oxo-1,3-oxazolidin-3-yl}ethyl)sulfanyl]-1,3-thiazole-4-carboxylic acid (compound 45-14), 2-[(2-{(4S,5S)-4-[(1E,6E)-4-hydroxy-4-methyl-1,6-nonadienyl]-5-methyl-2-oxo-1,3-oxazolidin-3-yl}ethyl)sulfanyl]-1,3-thiazole-4-carboxylic acid (compound 45-15), 2-[(2-{(4S,5S)-4-[(1E)-5-cyclobutyl-4-hydroxy-4-methyl-1-pentenyl]-5-methyl-2-oxo-1,3-oxazolidin-3-yl}ethyl)sulfanyl]-1,3-thiazole-4-carboxylic acid (compound 45-17), 2-[(2-{(4S,5S)-4-[(1E)-5-cyclopropyl-4-hydroxy-4-methyl-1-pentenyl]-5-methyl-2-oxo-1,3-oxazolidin-3-yl}ethyl)sulfanyl]-1,3-thiazole-4-carboxylic acid (compound 45-18), 2-[(2-{(4S,5S)-4-[(1E)-4-hydroxy-1-nonenyl]-5-methyl-2-oxo-1,3-oxazolidin-3-yl}ethyl)sulfanyl]-1,3-thiazole-4-carboxylic acid (compound 45-22), 2-[(2-{(4S,5S)-4-[3-(1-butylcyclobutyl)-3-hydroxypropyl]-5-methyl-2-oxo-1,3-oxazolidin-3-yl}ethyl)sulfanyl]-1,3-thiazole-4-carboxylic acid (compound 46), 2-[(2-{(1R,2R)-2-[(1E)-4-hydroxy-4-methyl-1-nonenyl]-5-oxocyclopentyl}ethyl)sulfanyl]-1,3-thiazole-4-carboxylic acid (compound 57), 2-{[2-((4S)-4-{(1E,3R)-3-[1-(4-fluorobutyl)cyclobutyl]-3-hydroxy-1-propenyl}-2-oxo-1,3-oxazolidin-3-yl)ethyl]sulfonyl}-1,3-thiazole-4-carboxylic acid (compound 63), 2-[(2-{(4S)-2-oxo-4-[(1E,4S)-8,8,8-trifluoro-4-hydroxy-4-methyl-1-octenyl]-1,3-oxazolidin-3-yl}ethyl)sulfanyl]-1,3-thiazole-4-carboxylic acid (compound 65-2) or 3-{2-[((2R)-2-{(1E,3R)-3-[1-(4-fluorobutyl)cyclobutyl]-3-hydroxy-1-propenyl}-5-oxo-1-pyrrolidinyl)methyl]-1,3-thiazol-4-yl}propanoic acid (compound 76) etc.

Moreover, specifically preferred compound is compound 8-1, compound 8-6, compound 24, compound 25, compound 26, compound 30, compound 30-1, compound 31, compound 32-2, compound 34-6, compound 32-14, compound 45, compound 53 or compound 76 etc.

In the specification, limaprost is a compound represented by following formula

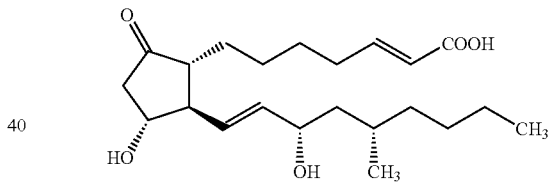

and its chemical name is (E)-7-[(1R,2R,3R)-3-hydroxy-2-[(3S,5S)-(E)-3-hydroxy-5-methyl-1-nonenyl]-5-oxocyclopentyl]-2-heptanoic acid. Limaprost alfadex tablet comprising limaprost as an active ingredient is sold as a drug which is effective for improving symptoms of thromboangiitis obliterans or lumbar spinal canal stenosis etc.

According to the present invention, unless otherwise indicated and as is apparent for those skilled in the art, symbol ⁀ indicates that it is bound to the opposite side of the sheet (namely α-configuration), symbol ⁀ indicates that it is bound to the front side of the sheet (namely β-configuration), ⁀ indicates that it is a α-configuration, β-configuration or a optional mixture thereof, and symbol ⁀ indicates that it is a optional mixture of α-configuration and β-configuration.

For example, in formula (I) or (I-1), a bond of X-D or a bond of Y—W may be a α-configuration, β-configuration or a mixture thereof.

Unless otherwise specifically mentioned, all isomers are included in the present invention. For example, alkyl, alkenyl, alkynyl, alkoxy, alkylthio, alkylene, alkenylene and alkynylene include straight chain and branched ones. Moreover, all of isomers due to double bond, ring and fused ring (E-, Z-, cis- and trans-forms), isomers due to presence of asymmetric carbon(s) etc. (R-, S-, α- and β-configuration, enantiomer and diastereomer), optically active compounds having optical rotation (D-, L-, d- and l-forms), polar compound by chromatographic separation (more polar compound and less polar compound), equilibrium compounds, rotational isomers, a mixture thereof in any proportion and a racemic mixture are included in the present invention. The optically active compound may include not only the one of 100% pure but also others comprising less than 50% of other optical isomers.

The salt is preferably water-soluble. The suitable salt includes salt with alkaline metal (e.g. potassium, sodium), salt with alkaline earth metal (e.g. calcium magnesium), ammonium salt, salt with pharmaceutically acceptable organic amine (e.g. tetramethylammonium, triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine) or acid addition salt etc.

The above-described acid addition salt is preferably water-soluble. The suitable acid addition salt includes such as inorganic acid salt such as hydrochloride, hydrobromide, hydroiodide, sulfate, phosphate and nitrate, or organic acid salt such as acetate, lactate, tartrate, benzoate, citrate, methanesulfonate, ethanesulfonate, benzenesulfonate, toluenesulfonate, isothionate, glucuronate and gluconate etc.

The compound of the present invention or the salt thereof may be converted to a solvate.

The solvate is preferably non-toxic and water-soluble. The suitable solvate includes, for example solvate of water or alcohol (e.g. ethanol).

The compound of the present invention and the pharmaceutically acceptable salt thereof are all preferable. Concretely, compounds described in Example and pharmaceutically acceptable salts thereof are included.

Moreover, the salt includes a quaternary ammonium salt. The quaternary ammonium salt is the compound where nitrogen is quarternalized by $R^0$.

$R^0$ is C1-8 alkyl or C1-8 alkyl substituted by phenyl.

The compound of the present invention can be converted into an N-oxide by known methods. The N-oxide is the compound in which nitrogen is oxidized.

The compound of the present invention can be converted into a cyclodextrin clathrate thereof by the method described in JP50-3362, JP52-31404 or JP61-52146 using α-, β- or γ-cyclodextrin, or a mixture thereof. Converting into the corresponding cyclodextrin clathrates serves to increase the stability and solubility in water of the compounds, and therefore it is useful in the use for pharmaceuticals.

A prodrug of the compound of the present invention means a compound which is converted to the compound of the present invention by reaction with an enzyme, gastric acid or the like in the living body. For example, with regard to a prodrug of the compound of the present invention, when the compound of the present invention has an amino group, compounds in which the amino group is, for example, acylated, alkylated or phosphorylated (e.g. compounds which is the amino group of the compound of the present invention is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, etc.); when the compound of the present invention has a hydroxyl group, compounds in which the hydroxyl group is, for example, acylated, alkylated, phosphorylated or borated (e.g., compounds in which the hydroxyl group of the compound of the present invention is acetylated, palmitoylated, propanoylated, pivaloylated, succinylated, fumarylated, alanylated or dimethylaminomethylcarbonylated); and that the carboxyl group of the compound of the present invention is, for example, esterified or amidated (e.g., compounds in which the carboxyl group of the compound of the present invention is made into ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide). Those compounds may be produced by a known method per se. The prodrug of the compound of the present invention may be either a hydrate or a non-hydrate. A prodrug of the compound of the present invention may also be a compound which is converted to the compound of the present invention under physiologic condition as described in "*Iyakuhin no kaihatsu*, Vol. 7 (Bunshi-sekkei), pp. 163~198 (Hirokawa-Shoten), 1990". And the compound of the present invention may also be labeled by a radio isotope (such as $^3H$, $^{14}C$, $^{35}S$, $^{125}I$, etc,).

Processes for the Preparation of the Compound of the Present Invention:

The compound represented by formula (I) of the present invention can be prepared by methods which properly improved and combined known methods such as a method described in JP52-27753, JP55-100360, WO2003/74483, Synlett 2002, No. 1, 239-242 or Comprehensive Organic Transformations: A Guide to Functional Group Preparations 2nd Edition (Richard C. Larock, John Wiley & Sons Inc, 1999), a method described below, or a method described in Examples.

For example, among the compounds represented by formula (I), a compound wherein W is

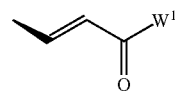

(wherein $W^1$ is hydrocarbon which may have a substituent(s).), i.e. a compound represented by formula (Ia)

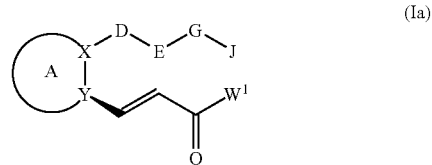

(wherein all symbols have same meanings as described above.) can be prepared by the below reaction using a compound represented by formula (II)

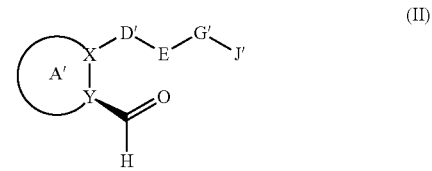

(wherein ring A', D', G' and J' have the same meanings as ring A, D, G and J respectively. With proviso that, carboxy group, hydroxy group, amino group or thiol group in ring A', D', G' and J' may be protected, if necessary. Other symbols have the same meaning as described above.) and a compound represented by formula (III)

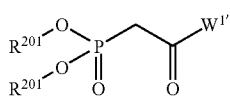

(wherein $R^{201}$ is C1-4 alkyl, $W^{1'}$ has the same meaning as $W^1$. With proviso that, carboxy group, hydroxy group, amino group or thiol group in $W^{1'}$ may be protected, if necessary.), if necessary, followed by removal of the protecting group.

The reaction of the above-described compounds represented by formulae (II) and (III) can be carried out by the known method. It is preferable that the reaction is carried out in organic solvent using strong base. The above-described organic solvent is, for example anhydrous tetrahydrofuran, dimethylformamide or dioxane etc. The above-described strong base is, for example sodium hydride, sodium amide or tert-butoxy potassium etc. Preferred as a reaction temperature is about −15 to 30° C.

The above-described protecting group of carboxy includes, for example, methyl, ethyl, allyl, tert-butyl, trichloroethyl, benzyl (Bn) and phenacyl etc.

The above-described protecting group of hydroxy includes, for example, methyl trityl, methoxymethyl (MOM), 1-ethoxyethyl (EE), methoxyethoxymethyl (MEM), 2-tetrahydropyranyl (THP), trimethylsilyl (TMS), triethylsilyl (TES), tert-butyldimethylsilyl (TBDMS), tert-butyldiphenylsilyl (TBDPS), acetyl (Ac), pivaloyl, benzoyl, benzyl (Bn), p-methoxybenzyl, allyloxycarbonyl (Alloc), and 2,2,2-trichloroethoxycarbonyl (Troc) etc.

The above-described protect group of amino includes, for example benzyloxycarbonyl, tert-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl, benzyl (Bn), p-methoxybenzyl, benzyloxymethyl (BOM) and 2-(trimethylsilyl)ethoxymethyl (SEM) etc.

The above-described protective group of thiol includes, for example, benzyl, methoxybenzyl, methoxymethyl (MOM), 2-tetrahydropyranyl (THP), diphenylmethyl and acetyl (Ac) etc.

The reaction for removing the protective group for carboxyl hydroxyl, amino or thiol is known and its examples are as follows.

(1) a hydrolyzing reaction with an alkali;
(2) a deprotection reaction under an acidic condition;
(3) a deprotection reaction by hydrogenolysis;
(4) a deprotection reaction of silyl;
(5) a deprotection reaction using a metal; and
(6) a deprotection reaction using metal complex.

Those methods will be specifically illustrated as follows.

(1) It is preferable that a deprotection reaction using an alkali is carried out, for example, at 0 to 40° C. using a hydroxide of alkaline metal (such as sodium hydroxide, potassium hydroxide and lithium hydroxide), a hydroxide of alkaline earth metal (such as barium hydroxide and calcium hydroxide), a carbonate (such as sodium carbonate and potassium carbonate), an aqueous solution thereof or a mixture thereof in an organic solvent (such as methanol, tetrahydrofuran and dioxane etc.).

(2) It is preferable that deprotection reaction under an acidic condition is carried out for example, at 0 to 100° C. in an organic acid (e.g. acetic acid, trifluoroacetic acid, methanesulfonic acid or p-tosylate), an inorganic acid (e.g. hydrochloric acid and sulfuric acid) or a mixture thereof (such as hydrogen bromide/acetic acid) in an organic solvent (such as dichloromethane, chloroform, dioxane, ethyl acetate and anisole etc.).

(3) It is preferable that a deprotection reaction by hydrogenolysis is carried out, for example, at 0 to 200° C. in a hydrogen atmosphere of ordinary pressure or high pressure or in the presence of ammonium formate in the presence of a catalyst (such as palladium-carbon, palladium black, palladium hydroxide, platinum oxide and Raney nickel) in a solvent [such as an ether type (such as tetrahydrofuran, dioxane, dimethoxyethane and diethyl ether), an alcohol type (such as methanol and ethanol), a benzene type (such as benzene and toluene), a ketone type (such as acetone and methyl ethyl ketone), a nitrile type (such as acetonitrile), an amide type (such as dimethylformamide), water, ethyl acetate, acetic acid or a mixed solvent comprising two or more thereof].

(4) It is preferable that a deprotection reaction of silyl is carried out, for example, at 0 to 40° C. using tetrabutylammonium fluoride in an organic solvent miscible with water (such as tetrahydrofuran and acetonitrile etc.).

(5) It is preferable that a deprotection reaction using metal is carried out, for example, at 0 to 40° C. with or without ultrasonic wave in the presence of powdery zinc in an acidic solvent (such as acetic acid, a buffer of pH 4.2 to 7.2 and a mixed solution of the solution with an organic solvent such as tetrahydrofuran).

(6) It is preferable that a deprotection reaction using a metal complex is carried out, for example, at 0 to 40° C. using a metal complex [such as tetrakistriphenylphosphine palladium (0), bis(triphenylphosphine) palladium (II) dichloride, palladium (II) acetate and tris(triphenylphosphine) rhodium (I) chloride] in the presence or absence of a phosphine agent (such as triphenyl phosphine) in the presence of a trap reagent (such as tributyltin hydride, triethylsilane, dimedone, morpholine, diethylamine and pyrrolidine), an organic acid (such as acetic acid, formic acid and 2-ethylhexanoic acid) and/or an organic acid salt (such as sodium 2-ethylhexanoate and potassium 2-ethylhexanoate) in an organic solvent (such as dichloromethane, dimethylformamide, tetrahydrofuran, ethyl acetate, acetonitrile, dioxane and ethanol), water or a mixed solvent thereof.

Apart from the above, the deprotection may also be effected, for example, according to the methods described in T. W. Greene, *Protective Groups in Organic Synthesis*, Wiley, New York, 1999.

As persons skilled in the art can easily understand that the aimed compound of the present invention is able to be easily produced by using appropriate ones among those deprotection reactions.

Among the compound represented by formula (I), a compound wherein W is

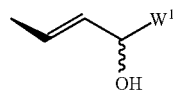

(wherein all symbols have the same meanings as described above.), i.e. a compound represented by formula (Ia-1)

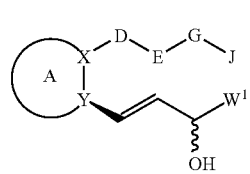

(wherein all symbols have the same meanings as described above.) can be prepared by reduction of a compound represented by formula (IV)

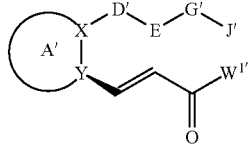

(wherein all symbols have the same meanings as described above.), if necessary,

The reduction may be carried out by the known method. It is preferred that the above-described compound represented by formula (IV) is treated with a reducing agent in organic solvent. Preferred as the organic solvent is, for example anhydrous tetrahydrofuran, methanol or dichloromethane etc. The reducing agent is, for example sodium borohydride, borane-tetrahydrofuran complex or borane-dimethyl sulfide complex etc. Preferred as a reaction temperature are about −78 to 30° C. The reduction may be carried out in the presence of (R)-2-methyl-CBS-oxazaborolidin or (S)-2-methyl-CBS-oxazaborolidin. The reduction may be carried out in the presence of lanthanide chloride. The lanthanide chloride includes cerium trichloride, samarium trichloride or europium trichloride. Specifically, cerium trichloride is preferable.

The removal of the protecting group can be carried out by the same method as described above.

Among the compound represented by formula (I), a compound wherein W is

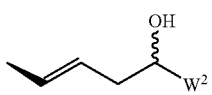

(wherein $W^2$ is hydrocarbon group which may have a substituent(s).), i.e. a compound represented by formula (Ib)

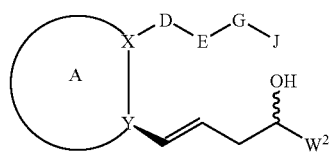

(wherein all symbols have the same meanings as described above.) can be prepared by the following reaction of the compound represented by formula (II) and a compound represented by formula (V)

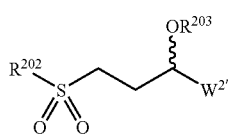

(wherein $R^{202}$ is aryl such as 1-phenyl-1H-tetrazolyl and phenyl, $R^{203}$ is a protecting group such as trimethylsilyl, tert-butyldimethylsilyl, and $W^{2'}$ has the same meaning as $W^1$. With proviso that, carboxy group, hydroxy group, amino group or thiol group in $W^{2'}$ may be protected, if necessary.), if necessary, followed by removal of the protecting group.

The reaction of the above-described compounds represented by formulae (II) and (V) can be carried out by the known method. In the reaction, it is preferable that the above-described compounds represented by formulae (II) and (V) are treated with base in organic solvent. The organic solvent includes, for example anhydrous tetrahydrofuran, dimethoxyethane, toluene or dimethylformamide etc. The base includes, for example potassium hexamethyldisilazide, lithium diisopropylamide or butyl lithium etc. Preferred as a reaction temperature are about −100 to −20° C.

The removal of the protecting group can be carried out by the same method as described above.

The compound represented by formula (Ib) can be prepared by the following reaction of the compound represented by formula (II) and a compound represented by formula (VI)

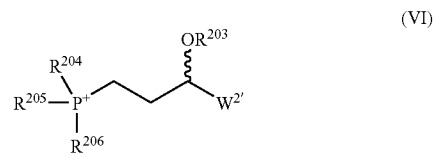

(wherein $R^{204}$, $R^{205}$ and $R^{206}$ are, each independently aryl such as phenyl and the other symbols have the same meanings as described above.), if necessary, followed by removal of the protecting group.

The reaction of the above-described compounds represented by formulae (II) and (VI) can be carried out by the known method. In the reaction, it is preferable that the above-described compounds represented by formulae (II) and (VI) are treated with strong base in organic solvent. The organic solvent includes, for example anhydrous tetrahydrofuran, dimethoxyethane, toluene or dimethylformamide etc. The strong base includes, for example lithium diisopropylamide, butyl lithium or sodium hydride etc. Preferred as a reaction temperature are about −100 to −20° C.

Among the compound represented by formula (I), a compound wherein W is

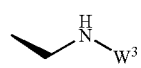

(wherein $W^3$ is hydrocarbon group which may have a substituent(s).), i.e. a compound represented by formula (Ic)

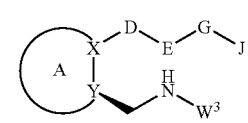

(wherein all symbols have the same meanings as described above.) can be prepared by reductive amination of the compound represented by formula (II) and a compound represented by formula (VII)

(wherein W³' has the same meaning as W³. With proviso that, carboxy group, hydroxy group, amino group or thiol group in W³' may be protected, if necessary.), if necessary, followed by removal of the protecting group.

The reductive amination can be carried out by the known method. It is preferable that the above-described compounds represented by formulae (II) and (VII) are treated with a reducing agent in organic solvent. The organic solvent includes, for example methanol, ethanol, dichloromethane, tetrahydrofuran, dimethoxyethane or diethylether etc. The reducing agent includes, for example sodium cyanoborohydride, sodium borohydride, sodium triacetoxyborohydride or pyridineborane etc. Preferred as a reaction temperature are about 0 to 100° C.

The removal of the protecting group can be carried out by the same method as described above.

Among the compound of the present invention, other compounds than the above-described can be prepared easily by combination of known methods such as the methods described in JP52-27753, JP55-100360, WO2003/174483 or *Comprehensive Organic Transformations: A Guide to Functional Group Preparations,* 2nd Edition (Richard C. Larock, John Wiley & Sons Inc, 1999) or methods modified partially thereof.

Other starting compounds or compounds used as reagent are known compounds can be prepared easily by combination of known methods such as the methods described in JP52-27753, JP55-100360, WO2003/74483, *Comprehensive Organic Transformations: A Guide to Functional Group Preparations,* 2nd Edition (Richard C. Larock, John Wiley & Sons Inc, 1999) or Elmer J. Rauckman et. al., J. Org. Chem., vol. 41, No. 3, 1976, p 564-565 etc. Moreover, the starting compounds may be used as salts thereof. As the salts, ones described as the above-described salts of the compounds of the present invention are used.

In each reaction of the specification, the reactions with heating, as will be apparent to those skilled in the art, it may be carried with water bath, oil bath, sand bath and microwave.

In each reaction of the specification, it may be used a solid phase reagent which is supported by polymer (for example, polystyrene, polyacrylamide, polypropylene or polyethyleneglycol etc.).

In each reaction of the specification, the obtained products may be purified by conventional techniques. For example, the purification may be carried out by distillation at atmospheric or reduced pressure, by high performance liquid chromatography with silica gel or magnesium silicate, by thin layer chromatography, by ion-exchange resin, by scavenger resin, by column chromatography, by washing or by recrystallization. The purification may be done each reaction or after several reactions.

Toxicity:

The toxicity of the compounds of the present invention is very low and therefore the compounds may be considered safe for pharmaceutical use.

Application to Pharmaceuticals:

The prostaglandin-like compound having weak blood pressure-lowering effect has an effect increasing cauda equina blood flow in the condition with a small influence on the general circulation. Therefore, it is effective for prevention and/or treatment for lumbago, lower limb pain, lower limb numbness, intermittent claudication, bladder disorders, rectal disorders or sexual dysfunction, and it is unlikely to be caused severe side effects to the general circulation.

Moreover, the compound of the present invention has weak blood pressure-lowering effect and an effect increasing cauda equina blood flow in mammal, especially human, so they are used for prevention and/or treatment of the above-described diseases.

The bladder disorder means dysuria due to compression of cauda equina nerve. It includes pollakiuria, delayed urination, forceless urinary stream, anuresis and urinary incontinence. Furthermore, the rectal disorder means defecation disorder due to compression of cauda equina nerve.

The agent of the present invention which has an effect increasing cauda equina blood flow can be used as a prevention and/or treatment for spinal canal stenosis.

When the agent of the present invention is used as the prevention and/or treatment for the lumbar spinal canal stenosis, the therapeutic effect is thought to be based on the improvement of hypofunction of the surrounding tissue of spinal canal such as intervertebral disk, the improvement of hyperplasia of yellow ligament, posterior ligament or the like; the improvement of inflammation or reduction of blood flow due to nerve compression; or the nerve protection.

The medicaments of the present invention may be administered as a combined preparation by combining with other medicaments for the purpose of 1) supplementing and/or enhancing of prevention and/or treatment effect of the compound, 2) improvement in pharmacokinetics and absorption and reduction of dose of the compound, and/or 3) reduction of side effect of the compound.

The combined preparation of the medicaments of the present invention with other medicaments may be administered in a form of a compounded agent in which both components are compounded in a preparation or may be in a form in which they are administered by means of separate preparations. The case of administration by means of separate preparations includes a simultaneous administration and administrations with time difference. In the case of administrations with time difference, the medicament of the present invention may be firstly administered followed by administering the other medicament or the other medicament may be administered firstly followed by administering the medicament of the present invention. Methods for each of the administration are the same or different.

Diseases prevented and/or treated by the concomitant medication are especially no limited. Any disease supplementing and/or enhancing the effect of the agent of the present invention is included.

The other medicaments for the purpose of supplementing and/or enhancing of prevention and/or treatment effect of the compound of the present invention include, for example, prostaglandins, prostaglandin derivatives formulations, non-steroidal anti-inflammatory drugs (NSAID), vitamins, muscle relaxants, antidepressants, nitric oxide synthase inhibitor, aldose reductase inhibitors, poly ADP-ribose polymerase (PARP) inhibitors, excitatory amino acid receptor antagonists (such as NMDA receptor antagonists and AMPA receptor antagonists), radical scavengers, astrocyte modulators, phosphodiesterase (PDE) inhibitors and immunosuppressive drugs (such as cyclosporine and FK506).

Examples of prostaglandins (hereinafter, abbreviated as PG) include PG receptor agonists and the like. Examples of PG receptors include PGE receptors (EP1, EP2, EP3 and EP4), PGD receptors (DP, CRTH2), PGF receptors (FP), PGI receptors (IP), TX receptors (TP), and the like. In addition, examples of prostaglandin derivative formulations include limaprost, limaprost alfadex beraprost and the like.

Examples of NSAID include sasapyrine, sodium salicylate, aspirin, aspirin dialuminate, diflunisal, indometacin, suprofen, ufenamate, dimethyl isopropylazulene, bufexamac, felbinac, diclofenac, tolmetin sodium, clinoril, fenbufen, nabumetone, proglumetacin, indometacin farnesil, acemetacin, proglumetacin maleate, amfenac sodium, mofezolac, etodolac, ibuprofen, ibuprofen piconol, naproxen, flurbiprofen, flurbiprofenaxetil, ketoprofen, fenoprofen calcium, tiaprofenic acid, oxaprozin, pranoprofen, loxoprofen sodium, alminoprofen, zaltoprofen, mefenamic acid, mefenamic acid aluminium, tolfenamic acid, floctafenine, ketophenylbutazon, oxyphenbutasone, piroxicam, tenoxicam, ampiroxicam, napageln ointment, epirizole, tiaramide hydrochloride, tinoridine hydrochloride, emorfazone, sulpyrine, migrenin, Saridon, Sedes G, amipylo-N, solvon, pyrine compounding cold medicine, acetaminophen, phenacetin, dimetotiazine mesilate, cimetoride-combined drug, non-pyrine-combined cold medicine and the like.

Examples of muscle relaxants include tolperisone hydrochloride, chlorzoxazone, chlormezanone, methocarbamol, phenprobamate, pridinol mesilate, chlorphenesin carbamate, baclofen, eperisone hydrochloride, afloqualone, tizaindine hydrochloride, alcuronium chloride, suxamethonium chloride, tubocurarine chloride, dantrolene sodium, pancuronium bromide, vecuronium bromide and the like.

Antidepressants include tricyclic antidepressants or tetracyclic antidepressants etc. Examples of tricyclic antidepressants include imipramine hydrochloride, desipramine hydrochloride, clomipramine hydrochloride, trimipramine maleate, amitriptyline hydrochloride, nortriptyline hydrochloride, lofepramine hydrochloride, amoxapine, dosulepin hydrochloride and the like. Examples of tetracyclic antidepressants include maprotiline, mianserin and the like.

Phosphodiesterase (PDE) inhibitors include, for example PDE3 inhibitors, PDE4 inhibitors or PDE5 inhibitors. Examples of PDE3 inhibitors include amrinone, milrinone, vesnarinone, cilostazol, sildenafil and the like. Examples of PDE4 inhibitors include Cilomilast (brand name; Ariflo), Roflumilast (BY-217), Arofylline, OPC-635, ONO-6126, IC-485, AWD-12-281, CC-10004, CC-1088, KW-4490, Iirimilast, ZK-117137, YM-976, BY-61-9987, CC-7085, CDC-998, MEM-1414, ND-1251, Bay19-8004, D-4396, PD-168787, Atizoram (CP-80633), Cipamfylline (BRL-61063), Rolipram, NIK-616, SCH-351591 or V-11294A etc. Examples of PDE5 inhibitors include Sildenafil, Sildenafil citrate and the like. Examples of the other PDE inhibitors include NT-702 and the like.

It is not especially limited compared with the weight of the medicaments of the present invention and other medicaments.

The other medicaments may be administrated with an optional combination of two or more kinds which are same or different.

Moreover, examples of the other medicaments for supplementing and/or enhancing the preventive and/or treatment effect of the medicaments of the present invention include not only known compounds but also new compound on the basis of the above-described mechanism.

In order to use the medicaments of the present invention or the medicaments of the present invention in combination with the other medicaments, these are normally administered to the entire or local part of human body orally or parentally.

The doses to be administered are determined depending upon, for example, age, body weight, symptom, the desired therapeutic effect, the route of administration, and the duration of the treatment as well as the medicament used in the invention. In the human adult, the doses per person are generally from 1 ng to 100 mg, by oral administration, up to several times per day, and from 0.1 ng to 10 mg, by parenteral administration, up to several times per day, or continuous administration from 1 to 24 hours per day from vein.

As mentioned above, the doses depend upon various conditions. Therefore, there are cases in which doses lower than or greater than the ranges specified above may be used.

The medicaments of the present invention, or concomitant medication combined the medicaments with other medicaments may be administered in the composition of, for example, solid compositions or liquid compositions, each for oral administration, or injections, external use, suppositories or inhalant each for parenteral administration.

Examples of the solid preparations for internal use for oral administration include tablets, pills, capsules, powders, granules and the like. The capsules include hard capsules and soft capsules.

Such a solid preparation for internal use is prepared by a formulation method commonly employed by using one or more active substances either as it is or as a mixture with an excipient (lactose, mannitol, glucose, microcrystalline cellulose, starch, etc.), a binder (hydroxypropylcellulose, polyvinylpyrrolidone, magnesium metasilicate aluminate, etc.), a disintegrating agent (calcium cellulose glycolate, etc.), a lubricant (magnesium stearate, etc.), a stabilizer and a dissolution aid (glutamic acid, aspartic acid, etc.). If necessary, it may be coated with a coating agent (sucrose, gelatin, hydroxypropylcellulose, hydroxypropylmethylcellulose phthalate, etc.). It may be coated with two or more layers. Moreover, capsules made of an absorbable material such as gelatin are involved in the scope thereof.

Liquid forms for oral administration include pharmaceutically acceptable solutions, suspensions and emulsions, syrups and elixirs. In such forms, one or more of the active compound(s) may be dissolved, suspended or emulized into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent.

In the parenteral administration, formulation of external use include, for example, ointment, gel, cream, poultice, patch, liniment, atomized agent, inhalation, spray and nasal spray, etc. They includes one or more of the active compound(s) and be prepared by known method or usual method.

Ointment is prepared by known method or usual method. For example, it is prepared by levigation or fusion of one or more of the active compound(s) and substrate. The substrate of ointment is selected from known or usual one. For example, higher fatty acid or higher fatty acid ester (adipic acid, myristic acid, palmitic acid, stearic acid, oleic acid, adipic acid ester, myristic acid ester, palmitic acid ester, stearic acid ester, oleic acid ester, etc.), wax (yellow beeswax, Spermaceti, ceresin, etc.), surfactant (polyoxyethylene alkyl ether phosphoric acid ester, etc.), higher alcohol (cetanol, stearil alcohol, cetostearyl alcohol, etc.), silicon oil (dimethyl polysiloxane, etc.), hydrocarbon hydrophilic petrolatum, white petrolatum, purified lanolin, light liquid paraffin, etc.), glycol (ethylene glycol, diethylene glycol, propylene glycol, polyethylene glycol, macrogol, etc.), vegetable oil (castor oil, olive oil, sesame oil, turpentine oil, etc.), animal oil (mink oil, egg yolk oil, squalane, squalene, etc.), water, absorption accelerator, skin fit inhibitor, etc. are used as single substance selected from them or mixture which consists of two or more kinds that is selected from them. Moreover, humectant, preservative agent, stabilizer, antioxidative agent, fragrant materials, etc. may be contained.

Gel is prepared by known method or usual method. For example, it is prepared by fusion of one or more of the active compound(s) and substrate. The substrate of gel is selected from known or usual one. For example, lower alcohol (ethanol, isopropylalcohol, etc.), gelling agent (carboxy methyl cellulose, hydroxy ethyl cellulose, hydroxy propyl cellulose, ethyl cellulose, etc.), neutralizing agent, (triethanolamine, diisopropanolamine, etc.), surfactant, (polyethylene glycol monostearate, etc.), gum, water, absorption accelerator, skin fit inhibitor, etc. are used as single substance selected from them or mixture which consists of two or more kinds that is selected from them. Moreover, preservative agent, antioxidative agent, fragrant materials, etc. may be contained.

Cream is prepared by known method or usual method. For example, it is prepared by fusion or emulsification of one or more of the active compound(s) and substrate. The substrate of cream is selected from known or usual one. For example, higher fatty acid ester, lower alcohol, hydrocarbon, polyalcohol (propylene glycol, 1,3-butylene glycol, etc.), higher alcohol (2-hexyldecanol cetanol, etc.), emulsifying agent (polyoxyethylene alkyl ether, fatty acid ester, etc.), water, absorption accelerator, skin fit inhibitor, etc. are used as single substance selected from them or mixture which consists of two or more kinds that is selected from them. Moreover, preservative agent, antioxidative agent, fragrant materials, etc. may be contained.

Poultice is prepared by known method or usual method. For example, it is prepared by fusion of one or more of the active compound(s) and substrate, and then the kneaded one is laid over support medium. The substrate for poultice is selected from known or usual one. For example, thickening agent (polyacrylic acid, polyvinylpyrrolidone, gum acacia, starch, gelatin, methyl cellulose, etc.), swelling agent (urea, glycerin, propylene glycol), bulking agent (kaolin, zinc oxide, talc, calcium, magnesium, etc.), water, solubilizing agent, thickener, skin fit inhibitor, etc. are used as single substance selected from them or mixture which consists of two or more kinds that is selected from them. Moreover, preservative agent, antioxidative agent, fragrant materials, etc. may be contained.

Patch is prepared by known method or usual method. For example, it is prepared by fusion of one or more of the active compound(s) and substrate, and then laid over support medium. The substrate for patch is selected from known or usual one. For example, polymer substrate, fat, higher fatty acid, thickener, skin fit inhibitor, etc. are used as single substance selected from them or mixture which consists of two or more kinds that is selected from them. Moreover, preservative agent, antioxidative agent, fragrant materials, etc. may be contained.

Liniment is prepared by known method or usual method. For example, one or more of the active compound(s) may be dissolved, suspended or emulsified in water, alcohol (ethanol, polyethylene glycol, etc.), higher fatty acid, glycerin, soap, emulsifying agent, suspending agent, etc. as single substance selected from them or mixture which consists of two or more kinds that is selected from them. Moreover, preservative agent, antioxidative agent, fragrant materials, etc. may be contained.

Atomized agent, inhalation and spray may comprise in addition to a diluent, a stabilizer such as sodium bisulfite and an isotonization buffer such as sodium chloride, sodium citrate or citric acid. The preparation process of sprays is described in detail in, for example, U.S. Pat. Nos. 2,868,691 and 3,095,355. Moreover, it is used aerosol agents.

Injections for parenteral administration include sterile aqueous, suspensions, emulsions and solid forms which are dissolved or suspended into solvent(s) for injection immediately before use. In injections, one or more of the active compound(s) may be dissolved, suspended or emulized into solvent(s). The solvents may include distilled water for injection, physiological salt solution, vegetable oil, propylene glycol, polyethylene glycol, alcohol, e.g. ethanol, or a mixture thereof. Injections may comprise some additives, such as stabilizing agents, solution adjuvants (such as glutamic acid, aspartic acid or POLYSORBATE80 (registered trade mark)), suspending agents, emulsifying agents, soothing agent, buffering agents, preservative. They may be sterilized at a final step, or may be prepared by an aseptic manipulation. They may also be manufactured in the form of sterile solid forms, for example, freeze-dried products, which may be dissolved in sterile water or some other sterile diluent(s) for injection immediately before use.

The dosage of inhalations for parenteral administration include aerosol, powders for inhalation or liquids for inhalation. The liquids for inhalation may be dissolved or suspended in water or the other appropriate solvent as needed.

Such inhalations are prepared in a known method.

For example, a liquid for inhalation is prepared by selecting proper additives from an antiseptic (such as benzalkonium chloride or p-aminobenzonic acid), a coloring agent, a buffering agent (such as sodium phosphate or sodium acetate), an isotonizing agent (such as sodium chloride or concentrated glycerin), thickening agent (such as carboxyvinylpolymer), or an accelerator of absorption, etc., if necessary.

A powder for inhalation is prepared by selecting proper additives from a lubricant agent (such as stearin acid and the salt thereof), a binding agent, (such as starch, dextrin), a diluting agent (such as lactose, cellulose), a coloring agent, an antiseptic (such as benzalkonium chloride or p-aminobenzonic acid), an accelerator of absorption, etc., if necessary.

In case of administration of liquid for inhalation, spray (atomizer, nebulizer) is usually used and in case of administration of powder for inhalation, inhalation administration apparatus for powder agents is usually used.

The other compositions for parenteral administration include suppositories for intrarectal administration and pessaries for vaginal administration which comprise one or more of the active substance(s) and may be prepared by methods known per se.

EFFECT OF THE INVENTION

The agent of the present invention has the advantage of having weak blood pressure-lowering effect and increasing cauda equina blood flow.

BEST MODE FOR CARRYING OUT THE INVENTION

The present invention is explained below in detail based on Examples, but the present invention is not limited thereto.

In chromatographic separations and TLC, the solvents in parenthesis show the eluting and developing solvents and the ratios of the solvents used are by volume.

Unless otherwise specified, NMR data is $^1$H-NMR data.

The solvents in parenthesis in NMR show the solvents used for measurement.

All the compounds described in the present specification were named using ACD/Name (registered trademark) or ACD/Name Batch (registered trademark) which names generally on the basis of IUPAC, or named according to IUPAC nomenclature system. For example, a compound represented by

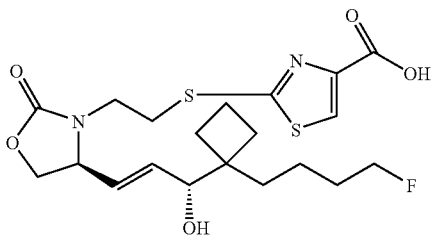

was named 2-{[2-((4S)-4-{(1E,3R)-3-[1-(4-fluorobutyl)cyclobutyl]-3-hydroxy-1-propenyl}-2-oxo-1,3-oxazolidin-3-yl)ethyl]sulfanyl}-1,3-thiazole-4-carboxylic acid (compound 8-1).

Example 1

(4S)-4-(hydroxymethyl)-1,3-oxazolidin-2-one (Compound 1)

D-serine methylester hydrochloride (5.76 g) was dissolved in water (52.0 mL). To the reaction solution was added potassium bicarbonate (4.08 g) and the solution was stirred for 10 minutes. To the reaction solution were added potassium bicarbonate (5.63 g) and a solution of triphosgen (14.3 g) in toluene (26.0 mL) at 0° C. and the solution was stirred for 2 hours. The reaction mixture as diluted with ethyl acetate and the water layer was concentrated. The obtained residue was extracted with methylene chloride, dried over anhydrous sodium sulfate and concentrated. To a solution of the obtained residue in ethanol (73.0 mL) was added sodium borohydride (1.34 g) and the solution was stirred at 3 hours. To the reaction mixture was added saturated ammonium chloride at 0° C. and the solution was stirred 30 minutes at room temperature. The reaction mixture was filtrated and concentrated. The obtained residue was purified by column chromatography on silica gel (ethyl acetate:methanol=4:1), to give the title compound (2.28 g) having the following physical data.

TLC: Rf 0.29 (ethyl acetate:methanol=10:1);

NMR (CDCl$_3$): δ 3.62 (dd, J=11.44, 5.77 Hz, 1H) 3.73 (m, 1H) 4.01 (m, 1H) 4.23 (m, 1H) 4.49 (t, J=8.70 Hz, 1H) 5.99 (s, 1H).

Example 2

(4R)-4-({[tert-butyl(dimethyl)silyl]oxy}methyl)-3-(2-hydroxyethyl)-1,3-oxazolidin-2-one (Compound 2)

Reaction A: To a solution of the compound 1 (2.28 g) in dimethylformamide (20.0 mL) were added imidazole (1.60 g) and tert-butyldimethylsilyl chloride (3.09 g) and the solution was stirred at room temperature over night. The reaction solution was poured into ice and extracted with ethyl acetate. The obtained organic layer was washed with water and brine, dried over anhydrous sodium sulfate and concentrated.

Reaction B: To a solution of the obtained residue in anhydrous tetrahydrofuran (45.0 mL) was added tert-butoxy potassium (2.41 g) under cooling with ice and the solution was stirred at 10 minutes. Bromo ethyl acetate (2.40 mL) was added dropwise to the reaction solution, which was stirred at room temperature for 3 hours. To the reaction mixture was added saturated ammonium chloride and the solution was extracted with ethyl acetate. The obtained organic layer was washed with brine, dried over anhydrous sodium sulfate and concentrated. To a solution of the obtained residue in tetrahydrofuran/ethanol (7:1) (46.0 mL) was added sodium borohydride (2.22 g) and the solution was stirred at room temperature for 2 hours. The reaction mixture was poured into ice/saturated ammonium chloride and extracted with ethyl acetate. The obtained organic layer was washed with water and brine, dried over anhydrous sodium sulfate and concentrated to give the title compound (4.62 g) having the following physical data. The compound was used in the next reaction without purification.

TLC Rf: 0.35 (hexane:ethyl acetate=1:2);

NMR (CDCl$_3$): δ 0.09 (s, 6H) 0.90 (s, 9H) 2.76 (s, 1H) 3.45 (m, 2H) 3.83 (m, 5H) 4.13 (dd, J=8.60, 5.68 Hz, 1H) 4.38 (dd, J=8.79, 8.60 Hz, 1H).

Example 3

S-{2-[(4R)-4-({[(tert-butyl(dimethyl)silyl]oxy}methyl)-2-oxo-1,3-oxazolidin-3-yl]ethyl}ethanethioate (Compound 3)

Methanesulfonyl chloride (1.43 mL) was added dropwise to a solution of the compound 2 (4.58 g) and triethylamine (3.50 mL) in methylene chloride (32.0 mL) under cooling with ice and the solution was stirred at 0° C. for 1 hour. To the reaction solution was added water and the solution was extracted with ethyl acetate. The organic layer was washed with 1N hydrochloric acid, water and brine, dried over anhydrous magnesium sulfate and concentrated. To a solution of the obtained residue in dimethylformamide (17.0 mL) was added potassium thioacetate (1.91 g) and the solution was stirred at room temperature for 2 hours. To the reaction solution was added water and the solution was extracted with ethyl acetate. The organic layer was washed with water and brine, dried over anhydrous sodium sulfate and concentrated to give the title compound (5.56 g) having the following physical data. The compound was used in the next reaction without purification.

TLC: Rf 0.76 (hexane:ethyl acetate=1:2);

NMR (CDCl$_3$): δ 0.08 (s, 6H) 0.89 (s, 9H) 2.35 (s, 3H) 3.07 (m, 2H) 3.31 (m, 1H) 3.57 (m, 1H) 3.68 (dd, J=10.80, 4.03 Hz, 1H) 3.79 (m, 1H) 3.93 (m, 1H) 4.12 (m, 1H) 4.33 (t, J=8.70 Hz, 1H).

Example 4

Ethyl 2-({2-[(4S)-4-(hydroxymethyl)-2-oxo-1,3-oxazolidin-3-yl]ethyl}thio)-1,3-thiazol-4-carboxylate (Compound 4)

Reaction A: To a solution of the compound 3 (5.56 g), ethyl 2-bromo-1,3-thiazole-4-carboxylata (4.34 g) and tributylphosphine (0.46 mL) in ethanol (36.0 mL) was added potassium carbonate (3.70 g) under cooling with ice and the solution was stirred at room temperature for 1 hour and subsequently at 50° C. overnight. To the reaction solution was added water and the solution was extracted with ethyl acetate. The organic layer was washed with water and brine, dried over anhydrous magnesium sulfate and concentrated.

Reaction B: To a solution of the obtained residue in tetrahydrofuran (18.0 mL) was a solution of 1M tetrabutylammonium iodide in tetrahydrofuran (18.4 mL) at 0° C. and the solution was stirred at room temperature for 1 hour. To the reaction solution was added water and the solution was extracted with ethyl acetate. The organic layer was washed with water and brine, dried over anhydrous magnesium sulfate and concentrated. The obtained residue was purified by column chromatography on silica gel (hexane:ethyl acetate=2:3), to give the title compound (4.29 g) having the following physical data.

TLC: Rf0.43 (ethyl acetate);

NMR (CDCl$_3$): δ 1.39 (m, 3H) 3.66 (m, 6H) 4.14 (m, 2H) 4.39 (m, 3H) 8.02 (s, 1H).

Example 5

Ethyl 2-({2-[(4R)-4-formyl-2-oxo-1,3-oxazolidin-3-yl]ethyl}thio)-1,3-thiazole-4-carboxylate (Compound 5)

To a solution of the compound 4 (338 mg) in dimethylsulfoxide (3.40 mL)/ethyl acetate (6.80 mL) were added triethylamine (1.00 mL) and sulfur trioxide-pyridine complex (650 mg) at 10° C. and the solution was stirred at room temperature for 1 hour. To the reaction solution was added 1N hydrochloric acid and the solution was extracted with ethyl acetate. The organic layer was washed water and brine, dried over anhydrous sodium sulfate and concentrated to give the title compound (336 mg) having the following physical data. The compound was used in the next reaction without purification.

TLC: Rf0.44 (ethyl acetate);

NMR (CDCl$_3$): δ 1.38 (t, J=7.05 Hz, 3H) 3.84 (m, 9H) 8.02 (m, 1H) 9.81 (s, 1H).

Example 6

Ethyl 2-[(2-{(4S)-4-[(1E)-4,4-dimethyl-3-oxo-1-octenyl]-2-oxo-1,3-oxazolidin-3-yl}ethyl)thio]-1,3-thiazole-4-carboxylate (Compound 6)

To sodium hydride (60.0% in oil) (49.0 mg) was added slowly a solution of dimethyl (3,3-dimethyl-2-oxoheptyl)phosphonate (332 mg) in anhydrous tetrahydrofuran (7.30 mL) at 0° C. and the solution was stirred at room temperate for 1 hour. To the reaction solution was added slowly a solution of the compound 5 (336 mg) in anhydrous tetrahydrofuran (2.90 mL) at room temperature and the solution was stirred for 2 hours. To the reaction solution was added 1N hydrochloric acid at 0° C. and the solution was extracted with ethyl acetate. The organic layer was washed with water and brine, dried over anhydrous sodium sulfate and concentrated. The obtained residue was purified by column chromatography on silica gel (hexane:ethyl acetate=3:2), to give the title compound (211 mg) having the following physical data.

TLC: Rf0.50 (hexane:ethyl acetate=1:1);

NMR (CDCl$_3$): δ 0.83 (t, J=7.14 Hz, 3H) 1.11 (m, 10H) 1.43 (m, 5H) 3.32 (m, 1H) 3.53 (m, 2H) 3.80 (m, 1H) 4.03 (m, 1H) 4.41 (m, 3H) 4.76 (m, 1H) 6.71 (m, 2H).

Example 7

Ethyl 2-[(2-{(4S)-4-[(1E,3R)-3-hydroxy-4,4-dimethyl-1-octenyl]-2-oxo-1,3-oxazolidin-3-yl}ethyl)thio]-1,3-thiazole-4-carboxylate (Compound 7)

To a solution of the compound 6 (124 mg) in anhydrous methanol (1.40 mL) were added sodium borohydride (10.4 mg) and a catalytic amount of acetic acid at −78° C. and the solution was stirred at the same temperature for 1 hour. After return to room temperature, to the reaction solution was added water and the solution was extracted with ethyl acetate. The organic layer was washed with brine, dried over anhydrous sodium sulfate and concentrated. The obtained residue was purified by column chromatography on silica gel (hexane:ethyl acetate=1:1), to give the title compound (87.2 mg) having the following physical data.

TLC: Rf0.25 (hexane:ethyl acetate=1:1);

NMR (CDCl$_3$): δ 0.84 (m, 9H) 1.26 (m, 6H) 1.39 (t, J=7.14 Hz, 3H) 3.54 (m, 4H) 3.85 (d, J=6.04 Hz, 1H) 3.99 (m, 1H) 4.40 (m, 4H) 5.66 (m, 1H) 5.92 (m, 1H) 8.02 (s, 1H).

Example 8

2-[(2-{(4S)-4-[(1E,3R)-3-hydroxy-4,4-dimethyl-1-octenyl]-2-oxo-1,3-oxazolidin-3-yl}ethyl)sulfanyl]-1,3-thiazole-4-carboxylic acid (Compound 8)

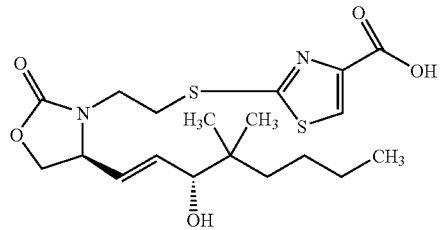

To a solution of the compound 7 (84.0 mg) in methanol (1.00 mL) was added an aqueous solution of 2N sodium hydroxide (0.19 mL) at 0° C. and the solution was stirred at room temperature for 1 hour. To the reaction solution was added an aqueous solution of 2N hydrochloric acid (0.30 mL). The solution was extracted with ethyl acetate and washed with water and brine. The reaction solution was dried over anhydrous sodium sulfate and concentrated to give the title compound (78.8 mg) having the following physical data.

TLC: Rf0.80 (ethyl acetate:methanol:acetic acid=8:1:1);

NMR (CDCl$_3$): δ 0.88 (m, 9H) 1.23 (m, 6H) 3.56 (m, 6H) 3.91 (d, J=5.95 Hz, 1H) 4.00 (m, 1H) 4.43 (m, 2H) 5.64 (dd, J=15.10, 7.60 Hz, 1H) 5.96 (dd, J=15.10, 5.95 Hz, 1H) 8.12 (s, 1H).

Example 8(1)-8(6)

By the same procedure as a series of reactions of example 6→example 7→example 8 using a corresponding phosphonate instead of dimethyl (3,3-dimethyl-2-oxoheptyl)phosphonate, the following compounds were obtained.

Example 8(1)

2-{[2-((4S)-4-{(1E,3R)-3-[1-(4-fluorobutyl)cyclobutyl]-3-hydroxy-1-propenyl}-2-oxo-1,3-oxazolidin-3-yl)ethyl]sulfanyl}-1,3-thiazole-4-carboxylic acid (Compound 8-1)

TLC: Rf0.56 (ethyl acetate:methanol:acetic acid=15:1:1);
NMR (CDCl$_3$): δ 1.62 (m, 12H) 3.48 (m, 3H) 3.69 (m, 1H) 3.98 (m, 1H) 4.02 (m, 2H) 4.14 (m, 1H) 4.45 (m, 4H) 5.71 (dd, J=15.29, 7.23 Hz, 1H) 5.94 (dd, J=15.27, 5.58 Hz, 1H) 8.13 (s, 1H).

Example 8(2)

2-{[2-((4S)-4-{(1E,3S)-3-[1-(4-fluorobutyl)cyclobutyl]-3-hydroxy-1-propenyl}-2-oxo-1,3-oxazolidin-3-yl)ethyl]sulfanyl}-1,3-thiazole-4-carboxylic acid (Compound 8-2)

TLC: Rf0.55 (ethyl acetate:methanol:acetic acid=15:1:1);
NMR (CDCl$_3$): δ 1.67 (m, 12H) 3.55 (m, 4H) 3.95 (m, 2H) 3.97 (m, 1H) 4.13 (m, 1H) 4.45 (m, 4H) 5.69 (dd, J=15.74, 8.24 Hz, 1H) 5.93 (dd, J=15.27, 6.12 Hz, 1H) 8.11 (s, 1H).

Example 8(3)

2-[(2-{(4S)-4-[(1E,3S,5S)-3-hydroxy-5-methyl-1-nonenyl]-2-oxo-1,3-oxazolidin-3-yl}ethyl)sulfanyl]-1,3-thiazole-4-carboxylic acid (Compound 8-3)

TLC: Rf0.44 (ethyl acetate:methanol:acetic acid=15:1:1);
NMR (CDCl$_3$): δ 0.90 (m, 6H) 1.30 (m, 9H) 3.51 (m, 6H) 3.99 (m, 1H) 4.29 (m, 1H) 4.42 (m, 2H) 5.62 (dd, J=15.29, 8.15 Hz, 1H) 5.94 (dd, J=15.29, 5.77 Hz, 1H) 8.12 (s, 1H).

Example 8(4)

2-{[2-((4S)-4-{(3S)-3-[1-(4-fluorobutyl)cyclobutyl]-3-hydroxypropyl}-2-oxo-1,3-oxazolidin-3-yl)ethyl]thio}-1,3-thiazole-4-carboxylic acid (Compound 8-4)

TLC: Rf0.31 (methylene chloride:methanol:acetic acid=18:1:1);
NMR (CDCl$_3$): δ 1.59 (m, 15H), 2.29 (m, 1H), 3.36 (m, 1H), 3.49 (m, 1H), 3.60 (m, 2H), 3.79 (m, 1H), 3.99 (m, 2H), 4.40 (m, 2H), 4.56 (t, J=5.86 Hz, 1H), 8.10 (s, 1H).

Example 8(5)

2-{[2-((4S)-4-{(3R)-3-[1-(4-fluorobutyl)cyclobutyl]-3-hydroxypropyl}-2-oxo-1,3-oxazolidin-3-yl)ethyl]thio}-1,3-thiazole-4-carboxylic acid (Compound 8-5)

TLC: Rf0.25 (methylene chloride:methanol:acetic acid=18:1:1);
NMR (CDCl$_3$): δ 1.62 (m, 16H), 3.59 (m, 5H), 4.01 (m, 2H), 4.39 (m, 2H), 4.56 (t, J=5.95 Hz, 1H), 8.11 (s, 1H).

Example 8(6)

2-[(2-{(4S)-4-[(1E,3R)-8-fluoro-3-hydroxy-4,4-dimethyl-1-octenyl]-2-oxo-1,3-oxazolidin-3-yl}ethyl)thio]-1,3-thiazole-4-carboxylic acid (Compound 8-6)

TLC: Rf0.54 (ethyl acetate:methanol:acetic acid=15:1:1);
NMR (CDCl$_3$): δ 0.85 (s, 3H) 0.87 (s, 3H) 1.34 (m, 4H) 1.65 (m, 2H) 3.43 (m, 5H) 3.69 (m, 1H) 3.97 (m, 2H) 4.45 (m, 4H) 5.66 (dd, J=15.10, 8.88 Hz, 1H) 5.95 (dd, J=15.10, 5.70 Hz, 1H) 8.12 (s, 1H).

Example 9(1)-9(7)

By the same procedure as a series of reactions of example 2→example 3→example 4→example 5→example 6→example 7→example 8 using (5R)-5-(hydroxymethyl)pyrrolidin-2-one instead of the compound 1 and using dimethyl (3,3-dimethyl-2-oxoheptyl)phosphonate or a corresponding phosphonate, the following compounds were obtained.

Example 9(1)

2-[(2-{(2R)-2-[(1E,3R)-3-hydroxy-4,4-dimethyl-1-octenyl]-5-oxo-1-pyrrolidinyl}ethyl)sulfanyl]-1,3-thiazole-4-carboxyl acid (Compound 9-1)

TLC: Rf0.54 (ethyl acetate:methanol:acetic acid=8:1:1);
NMR (CDCl$_3$): δ 0.89 (m, 9H) 1.27 (m, 6H) 1.81 (m, 1H) 2.34 (m, 3H) 3.41 (m, 3H) 3.83 (m, 2H) 4.17 (m, 1H) 5.57 (dd, J=14.92, 8.33 Hz, 1H) 5.84 (dd, J=14.92, 6.30 Hz, 1H) 8.09 (s, 1H).

Example 9(2)

2-[(2-{(2R)-2-[(1E,3R)-3-hydroxy-4,4-dimethyl-1-pentenyl]-5-oxo-1-pyrrolidinyl}ethyl)sulfanyl]-1,3-thiazole-4-carboxylic acid (Compound 9-2)

TLC: Rf0.34 (ethyl acetate:methanol:acetic acid=8:1:1);
NMR (CDCl$_3$): δ 0.91 (s, 9H) 1.79 (m, 1H) 2.36 (m, 3H) 3.75 (m, 7H) 5.57 (dd, J=14.92, 8.70 Hz, 1H) 5.82 (dd, J=15.20, 6.41 Hz, 1H) 8.09 (s, 1H).

Example 9(3)

2-[(2-{(2R)-2-[(1E,3R-3-hydroxy-4,4-dimethyl-1-hexenyl]-5-oxo-1-pyrrolidinyl}ethyl)sulfanyl]-1,3-thiazole-4-carboxylic acid (Compound 9-3)

TLC: Rf0.36 (ethyl acetate:methanol:acetic acid=8:1:1);
NMR (CDCl$_3$): δ 0.86 (m, 9H) 1.30 (m, 2H) 1.78 (m, 1H) 2.37 (m, 3H) 3.69 (m, 7H) 5.57 (dd, J=15.47, 8.33 Hz, 1H) 5.83 (m, J=15.29, 6.68 Hz, 1H) 8.09 (s, 1H).

Example 9(4)

2-[(2-{(2R)-2-[(1E,3S)-3-hydroxy-4,4-dimethyl-1-heptenyl]-5-oxo-1-pyrrolidinyl}ethyl)sulfanyl]-1,3-thiazole-4-carboxylic acid (Compound 9-4)

TLC: Rf0.46 (ethyl acetate:methanol:acetic acid=8:1:1);
NMR (CDCl$_3$): δ 0.89 (m, 9H) 1.23 (m, 4H) 1.77 (m, 1H) 2.37 (m, 3H) 3.69 (m, 8H) 5.56 (ddd, J=15.42, 8.83, 0.82 Hz, 1H) 5.84 (dd, J=15.29, 6.68 Hz, 1H) 8.09 (m, 1H).

Example 9(5)

2-[(2-{(2R)-2-[(1E,3R)-3-methoxy-4,4-dimethyl-1-octenyl]-5-oxo-1-pyrrolidinyl}ethyl)sulfanyl]-1,3-thiazole-4-carboxylic acid (Compound 9-5)

TLC: Rf0.70 (ethyl acetate:methanol:acetic acid=15:1:1);
NMR (CDCl$_3$): δ 0.87 (m, 9H) 1.22 (m, 6H) 1.80 (m, 1H) 2.39 (m, 3H) 3.69 (m, 10H) 5.48 (dd, J=15.33, 8.51 Hz, 1H) 5.63 (dd, J=15.33, 7.50 Hz, 1H) 8.09 (s, 1H).

Example 9(6)

2-{[2-((2R)-2-{(1E,3R)-3-[1-(4-fluorobutyl)cyclobutyl]-3-hydroxy-1-propenyl}-5-oxo-1-pyrrolidinyl)ethyl]sulfanyl}-1,3-thiazole-4-carboxylic acid (Compound 9-6)

TLC: Rf0.33 (ethyl acetate:methanol:acetic acid=5:1:1);
NMR (CDCl$_3$): δ 1.63 (m, 13H) 2.36 (m, 3H) 3.96 (m, 10H) 5.64 (m, 1H) 5.82 (dd, J=15.30, 5.70 Hz, 1H) 8.10 (s, 1H).

Example 9(7)

2-[(2-{(2R)-2-[(1E)-3-hydroxy-4-phenoxy-1-butenyl]-5-oxo-1-pyrrolidinyl}ethyl)sulfanyl]-1,3-thiazole-4-carboxylic acid (Compound 9-7)

TLC: Rf0.26 (ethyl acetate:methanol:acetic acid=15:1:1);
NMR (CDCl$_3$): δ 1.81 (m, 1H) 2.36 (m, 3H) 3.39 (m, 3H) 3.81 (m, 2H) 4.01 (m, 4H) 4.58 (m, 1H) 5.80 (m, 1H) 5.88 (m, 1H) 6.89 (m, 2H) 6.98 (m, 1H) 7.29 (m, 2H) 8.06 (m, 1H).

Example 10

2-{[2-((2R)-2-{[(3-butoxyphenyl)amino]methyl}-5-oxo-1-pyrrolidinyl)ethyl]sulfanyl}-1,3-thiazole-4-carboxylic acid (Compound 10)

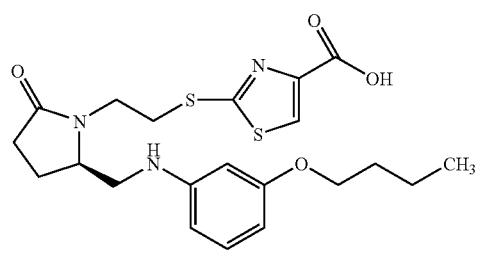

To a solution of the compound 5 (319 mg) in methylene chloride (2.40 mL) were added (3-butoxyphenyl)amine (119 mg) and acetic acid (0.10 mL) and the solution was stirred at room temperature for 1 hour. To the reaction solution was added sodium triacetoxyborohydride (161 mg) and the solution was stirred at room temperature over night. The reaction solution was diluted with ethyl acetate, washed with saturated sodium bicarbonate solution, water and brine, dried over anhydride sodium sulfate and concentrated. The obtained residue was purified by column chromatography on silica gel (hexane:ethyl acetate=2:3). The title compound (76.3 mg) having the following physical data was obtained by the same procedure as Example 8 using the obtained compound.

TLC: Rf0.64 (ethyl acetate:methanol:acetic acid=8:1:1);
NMR (CDCl$_3$): δ 0.97 (t, J=7.32 Hz, 3H) 1.48 (m, 2H) 1.74 (m, 2H) 1.94 (m, 1H) 2.36 (m, 3H) 3.43 (m, 7H) 3.92 (t, J=6.50 Hz, 2H) 4.03 (m, 1H) 6.21 (m, 2H) 6.32 (m, 1H) 7.08 (m, 1H) 8.09 (s, 1H).

Example 11

Tert-butyl (2R)-2-({[tert-butyl(dimethyl)silyl]oxy}methyl)-5-oxopyrrolidine-1-carboxylate (Compound 11)

To a solution of (5R)-5-(hydroxymethyl)pyrrolidin-2-one (6.42 g) in dimethylformamide (50 mL) were added imidazole (4.6 g) and tert-butyldimethylsilyl chloride (9.2 g) and the solution was stirred at room temperature for 1.5 hours. The reaction solution was poured into ice water and extracted with ethyl acetate. The organic layer was washed with brine and dried over anhydrous magnesium sulfate. The reaction solution was filtrated and concentrated. To a solution of the obtained compound in tetrahydrofuran (150 mL) were added triethylamine (9.33 mL), dimethylaminopyridine (1.36 g) and di-tert-butyl dicarbonate (14.6 g) and the solution was stirred at room temperature overnight. Water was added to the reaction solution, which was extracted with ethyl acetate. The organic layer was washed with brine and dried over anhydrous magnesium sulfate. The reaction solution was filtrated and concentrated. The obtained residue was purified by flush column chromatography (n-hexane:ethyl acetate=10:1) to give the title compound (18.38 g) having the following physical data.

TLC: Rf0.59 (n-hexane:ethyl acetate=3:1);
NMR (CDCl$_3$): δ 0.03 (s, 3H) 0.05 (s, 3H) 0.88 (s, 9H) 1.53 (s, 9H) 2.07 (m, 2H) 2.37 (ddd, J=17.53, 9.38, 2.56 Hz, 1H) 2.70 (m, 1H) 3.69 (dd, J=10.44, 2.38 Hz, 1H) 3.92 (dd, J=10.43, 4.04 Hz, 1H) 4.16 (m, 1H).

Example 12

Tert-butyl (2R)-2-({[tert-butyl(dimethyl)silyl]oxy}methyl)-5-oxo-2,5-dihydro-1H-pyrrole-1-carboxylate (Compound 12)

Lithium diisopropylamide (2M solution in heptane/tetrahydrofuran/ethylbenzene) solution (11.98 mL) was added dropwise slowly to a solution of the compound 11 (6.58 g) in tetrahydrofuran (15 mL) and the solution was stirred at 30 minutes. A solution of Benzeneselenenyl chloride (4.59 g) in tetrahydrofuran (30 mL) was added dropwise slowly to the reaction solution, which was stirred at −78° C. for 1 hour. To the reaction solution was added an aqueous saturated ammonium chloride solution at −78° C. The reaction solution was extracted with ethyl acetate. The organic layer was washed with brine and dried over anhydrous magnesium sulfate. The reaction solution was filtrated through Celite (Brand name) and concentrated. The obtained residue was purified by flush column chromatography (n-hexane:ethyl acetate=20:1). To a solution of the obtained compound (3.87 g) in tetrahydrofuran/ethyl acetate (2:3) (80 mL) were added sodium bicarbonate (1.68 g) and 30% hydrogen peroxide solution (3.2 mL) at 0° C. After 1 hour, to the reaction mixture was added water. The reaction solution was extracted with ethyl acetate. The organic layer was washed with an aqueous saturated sodium bicarbonate solution and brine, and dried over anhydrous magnesium sulfate. The reaction solution was filtrated through Celite (Brand name) and concentrated. The obtained residue was purified by flush column chromatography (n-hexane:ethyl acetate=15:1) to give the title compound (1.89 g) having the following physical data.

TLC: Rf0.40 (n-hexane:ethyl acetate=3:1);

NMR (CDCl$_3$): δ 0.04 (s, 3H) 0.05 (s, 3H) 0.87 (s, 9H) 1.56 (s, 9H) 3.71 (dd, J=9.61, 6.68 Hz, 1H) 4.15 (dd, J=9.70, 3.66 Hz, 1H) 4.60 (m, 1H) 6.13 (dd, J=6.22, 1.65 Hz, 1H) 7.26 (dd, J=6.04, 2.20 Hz, 1H).

Example 13

Tert-butyl (1R,2R,5S)-2-(hydroxymethyl)-4-oxo-3-azabicyclo[3.1.0]hexane-3-carboxylate (Compound 13)

Reaction A: To a solution of the compound 12 (1.25 g) and palladium acetate (171 mg) in diethylether (30 mL) was excessive amounts of a solution of diazomethane in ether (83 mL). The reaction mixture was filtrated through Celite (Brand name) and concentrated. The reaction mixture was purified by flush column chromatography (n-hexane:ethyl acetate=9:1).

Reaction B: To a solution of the obtained compound (1.21 g) in methanol (35 mL) was added 10-camphorsulfonic acid (32 mg) and the solution was stirred at room temperature overnight. The reaction solution was concentrated and water was added thereto. The solution was extracted with ethyl acetate. The organic layer was washed with brine and dried over anhydrous magnesium sulfate. The reaction solution was filtrated through Celite (Brand name) and concentrated to give the title compound (703 mg) having the following physical data. The compound was used in next reaction without purification.

TLC: Rf0.58 (ethyl acetate);

NMR (CDCl$_3$): δ 0.77 (m, 1H) 1.19 (m, 1H) 1.51 (s, 9H) 1.88 (m, 1H) 2.01 (m, 1H) 2.42 (m, 1H) 3.84 (d, J=4.03 Hz, 2H) 4.11 (td, J=4.44, 1.19 Hz, 1H).

Example 14

(1S,4R,5R)-4-[(3,5-dichlorophenoxy)methyl]-3-azabicyclo[3.1.0]hexan-2-one (Compound 14)

To a solution of the compound 13 (677 mg) in tetrahydrofuran (10 mL) were added triethylamine (0.62 mL) and methanesulfonyl chloride (0.28 mL) at 0° C. and the solution was stirred at 25 minutes. Water was added to the reaction solution, which was extracted by ethyl acetate. The organic layer was washed with brine and dried over anhydrous magnesium sulfate. The reaction solution was filtrated and concentrated. To a solution of the obtained residue in dimethylformamide (10 mL) were added cesium carbonate (1.46 g) and 3,5-dichlorophenol (583 mg) and the solution was stirred at 40° C. overnight. Water was added to the reaction solution, which was extracted with ethyl acetate. The organic layer was washed with brine and dried over anhydrous magnesium sulfate. The reaction solution was filtrated through Celite (Brand name) and concentrated. The obtained residue was purified by flush column chromatography (n-hexane:ethyl acetate=10:1). To a solution of the obtained compound (505 mg) in methylene chloride (3.00 mL) was added trifluoroacetic acid (0.50 mL) and the solution was stirred at room temperature for 1 hour. The reaction solution was diluted with ethyl acetate and washed with an aqueous sodium bicarbonate solution and brine. The reaction solution was dried over anhydrous sodium sulfate and concentrated to give the title compound (369 mg) having the following physical data. The compound was used in next reaction without purification.

TLC: Rf0.54 (ethyl acetate);

NMR (CDCl$_3$): δ 0.81 (m, 1H) 1.22 (m, 1H) 1.89 (m, 2H) 3.91 (m, 3H) 5.55 (s, 1H) 6.80 (d, J=1.83 Hz, 2H) 7.00 (t, J=1.83 Hz, 1H).

Example 15

2-[(2-{(1R,2R,5S)-2-[(3,5-dichlorophenoxy)methyl]-4-oxo-3-azabicyclo[3.1.0]hex-3-yl}ethyl)sulfanyl]-1,3-thiazole-4-carboxylic acid (Compound 15)

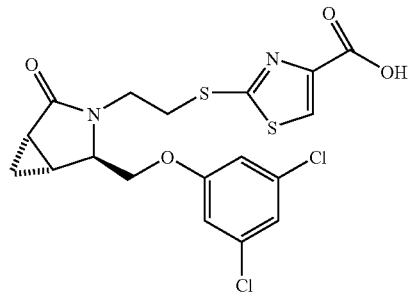

By the same procedure as a series of reactions of the reaction B of example 2→example 3→the reaction A of example 4→example 8 using the compound 14 instead of the compound 1, the title compound having the following physical data was obtained.

TLC: Rf0.77 (ethyl acetate:methanol:acetic acid=8:1:1);

NMR (CDCl$_3$): δ 0.63 (m, 1H) 1.19 (m, 1H) 1.82 (m, 1H) 2.03 (m, 1H) 3.38 (m, 3H) 4.00 (m, 4H) 6.82 (d, J=1.65 Hz, 2H) 6.99 (s, 1H) 8.10 (s, 1H).

Example 16

(5Z)-7-[(1R,2S,5S)-2-({[tert-butyl(diphenyl)silyl]oxy}methyl)-5-hydroxycyclopenthyl]-5-heptenoic acid (Compound 16)

To a solution of (3aR,4S,6aS)-4-({[tert-butyl(diphenyl)silyl]oxy}methyl)hexahydro-2H-cyclopenta[b]furan-2-one (3.15 g) in anhydrous toluene (32.0 mL) was added diisobuthylaluminium hydride (0.95 M in hexane) (9.20 mL) at −78° C. and the solution was stirred for 30 minutes. Water was added to the reaction solution, which was extracted with ethyl acetate. The organic layer was washed with saturated potassium hydrogen tartrate solution and brine, dried over anhydrous sodium sulfate and concentrated. To a solution of (4-carboxybutyl)(triphenyl)phosphonium bromide (8.89 g) in anhydrous tetrahydrofuran (60.0 mL) was added potassium tert-butoxide (4.50 g) and the solution was stirred at room temperature for 1 hour. To the reaction solution was added a solution of the above-obtained residue in tetrahydrofuran (20.0 mL) at 0° C. and the solution was stirred at room temperature for 1 hour. An aqueous saturated ammonium chloride solution was added to the reaction solution, which was extracted with tert-butyl methyl ether. The organic layer was washed with brine, dried over anhydrous sodium sulfate and concentrated to give the title compound (3.85 g) having the following physical data. The compound was used in next reaction without purification.

TLC: Rf0.52 (ethyl acetate);

NMR (CDCl$_3$): δ 1.04 (s, 9H) 2.07 (m, 14H) 3.66 (m, 2H) 4.20 (m, 1H) 5.38 (m, 2H) 7.35 (m, 10H).

Example 17

Methyl 7-[(1R,2S,5S)-2-({[tert-butyl(diphenyl)silyl]oxy}methyl)-5-hydroxycyclopentyl]heptanoate (Compound 17)

To a solution of compound 16 (3.85 g) in acetone (32.0 mL) were added potassium carbonate (1.67 g) and methane iodide (0.75 mL) at 0° C. and the solution was stirred at room temperature overnight. The reaction solution was diluted with ethyl acetate, washed with an aqueous saturated ammonium chloride solution and brine, dried over anhydrous sodium sulfate and concentrated. The obtained residue was purified by column chromatography on silica gel (hexane:ethyl acetate=6:1). Under an atmosphere of argon, palladium carbon (650 mg) was added a solution of the obtained compound in methanol (32.0 mL) and then the solution was stirred at room temperature for 3 hours under an atmosphere of hydrogen. The reaction solution was filtrated through Celite (Brand name) and concentrated to give the title compound (3.18 g) having the following physical data. The compound was used in next reaction without purification.

TLC: Rf0.42 (hexane:ethyl acetate=2:1);

NMR (CDCl$_3$): δ 1.05 (s, 9H) 1.45 (m, 16H) 2.30 (t, J=7.51 Hz, 2H) 3.63 (m, 5H) 4.22 (m, 1H) 7.39 (m, 6H), 7.66 (m, 4H).

Example 18

Methyl 7-[(1R,2S,5S)-2-({[tert-butyl(diphenyl)silyl]oxy}methyl)-5-hydroxycyclopentyl]-2-(phenylseleno)heptanoate (Compound 18)

To a solution of diisopropylamine (2.60 mL) in anhydrous tetrahydrofuran (64.0 mL) was added n-butyl lithium (1.59 M in hexane) (12.0 mL) at −78° C. and the solution was stirred for 30 minutes. To the reaction solution was added slowly a solution of the compound 17 (3.18 g) in anhydrous tetrahydrofuran (20.0 mL) at −78° C. and the solution was stirred for 1 hour. A solution of diphenyl diselenide (2.82 g) in anhydrous tetrahydrofuran (10.0 mL) was added thereto at −78° C. and the solution temperature was risen to −10° C. for 2 hour. An aqueous saturated ammonium chloride solution was added to the reaction mixture, which was extracted with ethyl acetate. The organic layer was washed with brine, dried over anhydrous sodium sulfate and concentrated. The obtained residue was purified by column chromatography on silica gel (hexane:ethyl acetate=6:1), to give the title compound (2.93 g) having the following physical data.

TLC: Rf0.47 (hexane:ethyl acetate=2:1);

NMR (CDCl$_3$): δ 1.04 (s, 9H) 1.66 (m, 16H) 3.59 (m, 6H) 4.20 (m, 1H) 7.35 (m, 9H) 7.62 (m, 6H).

Example 19

Methyl 7-[(1R,2S,5S)-2-(acetyloxy)-5-formylcyclopentyl]-2-(phenylseleno)heptanoate (Compound 19)

To a solution of the compound 18 (2.93 g) in pyridine (5.00 mL) was added anhydrous acetic acid (0.85 mL) at 0° C. Moreover, 4-N,N-dimethylaminopyridine (30.0 mg) was added thereto and the solution was stirred at room temperature for 2 hours. The reaction solution was diluted with ethyl acetate, washed with 1N hydrochloric acid and brine, dried over anhydrous sodium sulfate and concentrated. The title compound (1.83 g) having the following physical data was obtained by the same procedure by the same procedure as a series of reactions of the reaction B of example 4→example 5 using the compound 14.

TLC: Rf0.42 (hexane:ethyl acetate=2:1);

NMR (CDCl$_3$): δ 1.33 (m, 19H) 3.59 (m, 1H) 3.63 (s, 3H) 5.27 (m, 1H) 7.30 (m, 3H) 7.58 (dd, J=7.69, 1.83 Hz, 2H) 9.63 (d, J=2.93 Hz, 1H).

Example 20

Methyl 7-{(1R,2S,5R)-2-acetyloxy-5-[(1E,5S)-5-methyl-3-oxo-1-nonenyl]cyclopentyl}-2-(phenylseleno)heptanoate (Compound 20)

By the same procedure as the reaction of example 6 using dimethyl [(4S)-4-methyl-2-oxooctyl]phosphonate instead of dimethyl (3,3-dimethyl-2-oxoheptyl)phosphonate, the title compound having the following physical data was obtained.

TLC: Rf0.58 (hexane:ethyl acetate=2:1);

NMR (CDCl$_3$): δ 0.89 (m, 6H) 1.68 (m, 26H) 2.33 (m, 1H) 2.50 (m, 1H) 3.56 (m, 1H) 3.62 (s, 3H) 5.24 (m, 1H) 6.10 (d, J=15.74 Hz, 1H) 6.64 (dd, J=15.74, 8.97 Hz, 1H) 7.31 (m, 3H) 7.58 (dd, J=7.69, 1.65 Hz, 2H).

Example 21

Methyl 7-{(1R,2S,5R)-2-(acetyloxy)-5-[(1E,3S,5S)-5-methyl-3-(tetrahydro-2H-pyran-2-yloxy)-1-nonenyl]cyclopentyl}-2-(phenylseleno)heptanoate (Compound 21)

Reaction A: To a solution of the compound 20 (2.33 g) in anhydrous tetrahydrofuran (20.0 mL) were added (R)-2-methyl-CBS-oxazaborolidine (1M in toluene) (1.70 mL) and borane-tetrahydrofuran complex (1M in tetrahydrofuran) (3.30 mL) at 0° C. and the solution was stirred at room temperature for 1 hour. Ethanol and water were added to the reaction solution, which was diluted with ethyl acetate. The diluted solution was washed with 1N hydrochloric acid, water and brine, dried over anhydrous sodium sulfate and concentrated. The obtained residue was purified by column chromatography on silica gel (hexane:ethyl acetate=4:1).

Reaction B: To a solution of the obtained compound in toluene (26.0 mL) were added dihydropyran (0.48 mL) and p-toluenesulfonic acid 1-hydrate (20.0 mg) and the solution was stirred at room temperature overnight. Triethylamine was added to the reaction solution, which was concentrated. The obtained residue was purified by column chromatography on silica gel (hexane:ethyl acetate=9:1), to give the title compound (1.63 g) having the following physical data.

TLC: Rf0.37 (hexane:ethyl acetate=4:1);

NMR (CDCl$_3$): δ 0.87 (m, 6H) 1.63 (m, 33H) 2.34 (m, 1H) 3.56 (m, 5H) 3.85 (m, 1H) 4.14 (m, 1H) 4.67 (m, 1H) 5.18 (m, 2H) 5.44 (m, 1H) 7.31 (m, 3H) 7.58 (m, 2H).

Example 22

Methyl 7-{(1R,2S,5R)-2-hydroxy-5-[(1E,3S,5S)-5-methyl-3-(tetrahydro-2H-pyran-2-yloxy)-1-nonenyl]cyclopentyl}-2-phenylseleno)heptanoate (Compound 22)

To a solution of the compound 21 (507 mg) in methanol (7.00 mL) was added potassium carbonate (128 mg) and the solution was stirred at room temperature overnight. The reaction solution was diluted with ethyl acetate and washed with an aqueous saturated ammonium chloride solution and brine. The reaction solution was dried over anhydrous sodium sulfite and concentrated. The obtained residue was purified by column chromatography on silica gel (hexane:ethyl acetate=4:1), to give the title compound (370 mg) having the following physical data.

TLC: Rf0.41 (hexane:ethyl acetate=2:1);

NMR (CDCl$_3$): δ 0.87 (m, 6H) 1.56 (m, 30H) 2.31 (m, 1H) 3.48 (m, 1H) 3.59 (m, 1H) 3.62 (s, 3H) 3.85 (m, 1H) 4.12 (m, 2H) 4.67 (s, 1H) 5.14 (m, 1H) 5.43 (m, 1H) 7.32 (m, 3H) 7.58 (m, 2H).

Example 23

(2E)-7-{(1R,2R)-2-[(1E,3S,5S)-5-methyl-3-(tetrahydro-2H-pyran-2-yloxy)-1-nonenyl]-5-oxocyclopentyl}-2-heptenoic acid (Compound 23)

Reaction A: To a solution of the compound 22 (367 mg) in ethyl acetate (3.00 mL)/tetrahydrofuran (2.00 mL) were added sodium bicarbonate (124 mg) and 35.5% hydrogen peroxide solution (0.20 mL) at 10° C. and the solution was stirred at room temperature for 30 minutes. The reaction solution was diluted with ethyl acetate and washed with an aqueous saturated sodium bicarbonate solution and brine. The reaction solution was dried over anhydrous sodium sulfate and concentrated. The obtained residue was dissolved into 1,2-dimethoxyethane (5.00 mL) and water (2.00 mL). Lithium hydroxide (33.0 mg) was added thereto and the solution was stirred at room temperature at 9 hours. The reaction solution was diluted with ethyl acetate, washed an aqueous saturated ammonium chloride solution and brine, dried over anhydrous sodium sulfate and concentrated.

Reaction B: To a solution of the obtained residue in acetone (11.0 mL) was added 2.67M Jones reagent (1.20 mL) at −30° C. for 30 minutes. 2-propanol was added to the reaction solution, which was diluted with tert-butyl methyl ether. The diluted solution was washed with water and brine, dried over anhydrous magnesium sulfate and concentrated. The obtained residue was purified by column chromatography on silica gel (hexane:ethyl acetate=2:1), to give the title compound (173 mg) having the following physical data.

TLC: Rf0.50 (ethyl acetate);

NMR (CDCl$_3$): δ 0.88 (m, 6H) 1.84 (m, 29H) 3.52 (m, 1H) 3.84 (m, 1H) 4.14 (m, 1H) 4.68 (m, 1H) 5.31 (dd, J=15.38, 8.42 Hz, 1H) 5.60 (m, 1H) 5.81 (dd, J=15.74, 1.46 Hz, 1H) 7.03 (m, 1H).

Example 24

(2E)-7-{(1R,2R)-2-[(1E,3S,5S)-3-hydroxy-5-methyl-1-nonenyl]-5-oxocyclopentyl}-2-heptenoic acid (Compound 24)

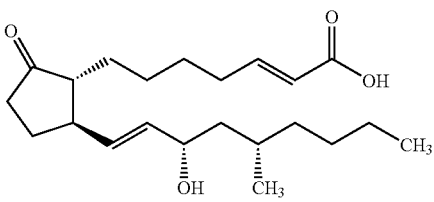

To the compound 23 (171 mg) was added acetic acid/tetrahydrofuran/water (65:10:35) (4.00 mL) and the solution was stirred at 50° C. for 50 minutes. The reaction solution was diluted with ethyl acetate, washed with water and brine, dried over anhydrous magnesium sulfate and concentrated. The obtained residue was purified by column chromatography on silica gel (hexane:ethyl acetate=1:1), to give the title compound (119 mg) having the following physical data.

TLC: Rf0.29 (ethyl acetate);

NMR (CDCl$_3$): δ 0.90 (m, 6H) 1.40 (m, 16H) 1.84 (m, 1H) 2.16 (m, 4H) 2.39 (m, 2H) 4.21 (m, 1H) 5.59 (m, 2H) 5.82 (d, J=15.74 Hz, 1H) 7.03 (m, 1H).

Example 25

(2E)-7-{(1R,2R,3R)-3-hydroxy-2-[(1E,3S,5S)-3-hydroxy-5-methyl-1-undecenyl]-5-oxocyclopentyl}-2-heptenoic acid (Compound 25)

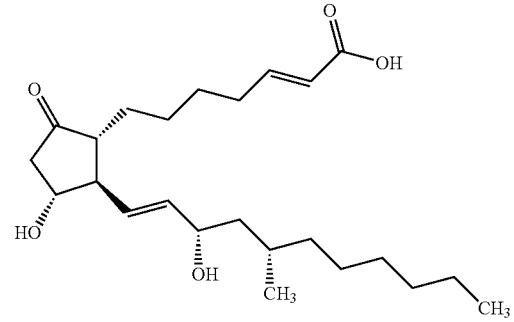

By the same procedure as a series of reactions of Example 16→Example 17→Example 18→Example 19→Example 6→Example 21→Example 22→Example 23→Example 24 using (3aR,4S,5R,6aS)-4-({[tert-butyl(diphenyl)silyl]oxy}methyl)-5-(tetrahydro-2H-pyran-2-yloxy)hexahydro-2H-cyclopenta[b]furan-2-one instead of (3aR,4S,6aS)-4-({[tert-butyl(diphenyl)silyl]oxy}methyl)hexahydro-2H-cyclopenta[b]furan-2-one and using dimethyl [(4S)-4-methyl-2-oxodecyl]phosphonate instead of dimethyl (3,3-dimethyl-2-oxoheptyl)phosphonate, the title compound having the following physical data was obtained.

TLC: Rf0.40 (chloroform:tetrahydrofuran:acetic acid=10:2:1);

NMR (CDCl$_3$): δ 7.01 (1H, dt, J=15.5 Hz), 5.80 (1H, d, J=16.0 Hz), 5.70-5.40 (2H, m), 4.25-4.11 (1H, m), 4.04 (1H, q, J=7.5 Hz), 2.74 (1H, dd, J=18.0 Hz), 0.92-0.75 [3H, t (23-CH$_3$)+3H, d (17-CH$_3$)].

Example 26

(2E)-7-{(1R,2S)-2-[(1E,3S,5S)-3-hydroxy-5-methyl-1-nonenyl]-5-oxo-3-cyclopenten-1-yl}-2-heptenoic acid (Compound 26)

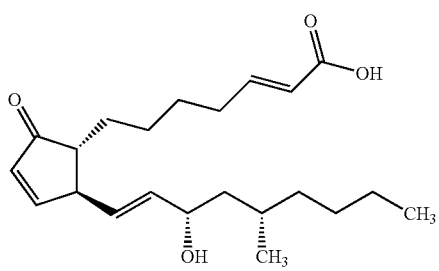

The title compound having the following physical data was obtained by the dehydration reaction of (2E)-7-{(1R,2R,3R)-3-hydroxy-2-[(1E,3S,5S)-3-hydroxy-5-methyl-1-nonenyl]-5-oxocyclopentyl}-2-heptenoic acid (Reg No. 88852-12-4) with hydrochloric acid.

TLC: Rf0.30 (ethyl acetate).

Example 27

Ethyl 2-({2-[(1R,2S,5S)-2-({[tert-butyl)(diphenyl)silyl]oxy}methyl)-5-hydroxycyclopentyl]ethyl}thio)-1,3-thiazole-4-carboxylate (Compound 27)

To a solution of (3aR,4S,6aS)-4-({[tert-butyl(diphenyl)silyl]oxy}methyl)hexahydro-2H-cyclopenta[b]furan-2-one (1.00 g) in anhydrous tetrahydrofuran (9.00 mL) was added lithium aluminum hydride (97.0 mg) at 0° C. and the solution was stirred for 20 minutes. At 0° C., water was added to the reaction solution, which was extracted with ethyl acetate. The reaction solution was washed an aqueous saturated sodium tartrate solution and brine, dried over anhydrous sodium sulfate and concentrated. A solution of the obtained residue and diisopropylethylamine (1.29 mL) in anhydrous tetrahydrofuran (9.00 mL) was added to a solution of methanesulfonyl chloride (0.23 mL) in anhydrous tetrahydrofuran (5.00 mL) at −5° C. and the solution was stirred for 20 minutes. To the reaction solution was added anhydrous methanol (43.0 μL) at −5° C. and the solution was stirred for 15 minutes. To the reaction solution was added trimethylsilyl chloride (0.49 mL) at −5° C. and the solution was stirred at room temperature for 10 minutes. To the reaction solution were added potassium carbonate (1.10 g), potassium thioacetate (578 mg) and anhydrous dimethylformamide (20.0 mL) and the solution was stirred at 50° C. for 5 hours. The reaction solution was poured into ice water. The solution was extracted with tert-butyl methyl ether, washed with water and brine, dried over anhydrous sodium sulfate and concentrated. To a solution of the obtained residue in ethanol (13.0 mL) were added tri-n-butylphosphine (0.07 mL), ethyl 2-bromo-1,3-thiazole-4-carboxylate (657 mg) and potassium carbonate (770 mg) and the solution was stirred at room temperature for 1 hour. Moreover the reaction solution was stirred at 50° C. overnight. The reaction solution was diluted with ethyl acetate and washed with an aqueous saturated ammonium chloride solution, water and brine. The reaction mixture was dried over anhydrous sodium sulfate and concentrated. The obtained residue was dissolved in tetrahydrofuran (8.60 mL). 1N hydrochloric acid (1.86 mL) was added thereto at 0° C. and the solution was stirred at room temperature for 30 minutes. The reaction solution was diluted with ethyl acetate, washed with water and brine, dried over anhydrous sodium sulfate and concentrated. The obtained residue was purified by column chromatography on silica gel (hexane:ethyl acetate=4:1), to give the title compound (624 mg) having the following physical data.

TLC: Rf0.36 (hexane:ethyl acetate=2:1);

NMR (CDCl$_3$): δ 1.05 (s, 9H) 1.38 (t, J=7.14 Hz, 3H) 1.77 (m, 8H) 2.82 (m, 1H) 3.20 (s, 1H) 3.58 (m, 3H) 4.41 (m, 3H) 7.41 (m, 6H) 7.65 (m, 4H) 7.96 (s, 1H).

Example 28

Ethyl 2-[(2-{(1R,2S,5R)-2-(acetyloxy)-5-[(1E,3S,5S)-5-methyl-3-(tetrahydro-2H-pyran-2-yloxy)-1-nonenyl]cyclopentyl}ethyl)thio]-1,3-thiazole-4-carboxylate (Compound 28)

By the same procedure as a series of reactions of Example 19→Example 6→Example 21 using the compound 27 instead of the compound 18 and using dimethyl [(4S)-4-methyl-2-oxodecyl]phosphonate instead of dimethyl (3,3-dimethyl-2-oxoheptyl)phosphonate, the title compound (442 mg) having the following physical data was obtained.

TLC: Rf0.64 (hexane:ethyl acetate=2:1);

NMR (CDCl$_3$): δ 0.86 (m, 6H) 1.47 (m, 25H) 2.04 (s, 3H) 2.39 (m, 1H) 3.24 (m, 2H) 3.49 (m, 1H) 3.85 (m, 1H) 4.14 (m, 1H) 4.40 (q, J=7.14 Hz, 2H) 4.64 (m, 1H) 5.23 (m, 2H) 5.45 (m, 1H) 8.02 (s, 1H).

Example 29

Ethyl 2-[(2-{(1R,2R)-2-[(1E,3S,5S)-3-hydroxy-5-methyl-1-nonenyl]-5-oxocyclopentyl}ethyl)thio]-1,3-thiazole-4-carboxylate (Compound 29)

Reaction A: The same reaction as Example 22 was carried out using a solution of the compound 28 (442 mg) in ethanol (7.70 mL) instead of a solution of the compound 21 (507 mg) in methanol (7.00 mL).

Reaction B: To a solution of the compound obtained in Reaction A (242 mg) in dimethylsulfoxide (1.10 mL)/ethyl acetate (2.20 mL) were added diisopropylamine (0.63 mL) and sulfur trioxide-pyridine complex (286 mg) at 10° C. and the solution was stirred at room temperature for 2 hours. Water was added to the reaction solution. The solution was extracted with ethyl acetate, washed with an aqueous saturated ammonium chloride solution, water and brine, dried over anhydrous sodium sulfate and concentrated. The title compound (144 mg) having the following physical data was obtained by the same procedure by the same procedure as the reaction of example 24 using the obtained residue instead of the compound 23.

TLC: Rf0.17 (hexane:ethyl acetate=2:1);

NMR (CDCl$_3$): δ 0.88 (m, 6H) 1.77 (m, 18H) 2.40 (m, 2H) 3.41 (m, 2H) 4.13 (m, 1H) 4.39 (q, J=7.14 Hz, 2H) 5.67 (m, 2H) 8.01 (s, 1H).

Example 30

2-[(2-{(1R,2R)-2-[(1E,3S,5S)-3-hydroxy-5-methyl-1-nonenyl]-5-oxocyclopentyl}ethyl)sulfanyl]-1,3-thiazole-4-carboxylic acid (Compound 30)

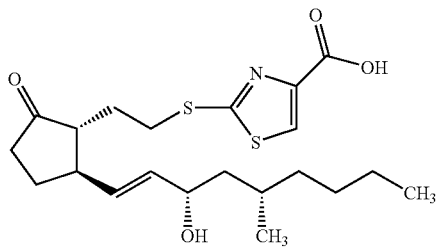

To a solution of the compound 29 (142 mg) in dimethylsulfoxide (7.00 mL)/phosphate buffer (7.00 mL) was added esterase from porcine liver (0.850 mL) and the solution was stirred at room temperature for 4 hours. The reaction solution was diluted with ethyl acetate and washed with an aqueous saturated ammonium sulfate solution, 1N hydrochloric acid, water and brine. The reaction solution was dried over anhydrous sodium sulfate and concentrated. The obtained residue was purified by column chromatography on silica gel (ethyl acetate), to give the title compound (88.0 mg) having the following physical data.

TLC: Rf0.29 (ethyl acetate:methanol=10:1);
NMR (CDCl$_3$): δ 0.87 (m, 6H) 1.29 (m, 10H) 1.66 (m, 1H) 2.11 (m, 4H) 2.47 (m, 2H) 3.36 (m, 3H) 4.21 (m, 1H) 5.67 (m, 2H) 8.10 (s, 1H).

Example 30(1)

2-[(2-{(1R,2R)-2-[(1E,3R)-3-hydroxy-4,4-dimethyl-1-octenyl]-5-oxocyclopentyl}ethyl)sulfanyl]-1,3-thiazole-4-carboxylic acid (Compound 30-1)

By the same procedure as a series of reactions of Example 19→Example 6→Example 21→Example 29→Example 30 using the compound 27 instead of the compound 18, the title compound having the following physical data was obtained.

TLC: Rf0.28 (ethyl acetate:methanol=10:1);
NMR (CDCl$_3$): δ 0.87 (m, 9H) 1.25 (m, 6H) 1.68 (m, 1H) 2.13 (m, 5H) 2.48 (m, 2H) 3.37 (m, 4H) 3.84 (d, J=5.49 Hz, 1H) 5.70 (m, 2H) 8.11 (s, 1H).

Example 31

7-{(1R,2R,3R)-3-hydroxy-2-[(1E,3S,5S)-3-hydroxy-5-methyl-1-nonenyl]-5-oxocyclopentyl}-6-oxoheptanoic acid (Compound 31)

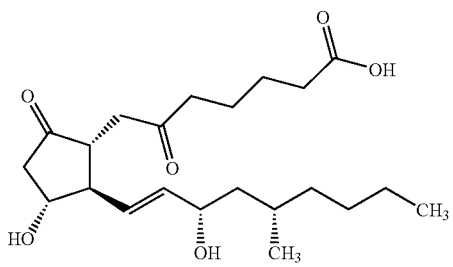

By the same procedure as the reaction of Example 30 using methyl 7-{(1R,2R,3R)-3-hydroxy-2-[(1E,3S,5S)-3-hydroxy-5-methyl-1-nonenyl]-5-oxocyclopentyl}-6-oxoheptanoate (Reg No. 70667-26-4) instead of the compound 29, the title compound having the following physical data was obtained.

TLC: Rf0.35 (chloroform:tetrahydrofuran:acetic acid=10:2:1).

Example 32(1)-32(18)

By the same procedure as a series of reactions of Example 6→Example 7→Example 8 using a corresponding phosphonate instead of dimethyl (3,3-dimethyl-2-oxoheptyl)phosphonate, the following title compounds were obtained.

Example 32(1)

2-[(2-{(4S)-4-[(1E,3R)-3-(1-butylcyclobutyl)-3-hydroxy-1-propenyl]-2-oxo-1,3-oxazolidin-3-yl}ethyl)sulfanyl]-1,3-thiazole-4-carboxylic acid (Compound 32-1)

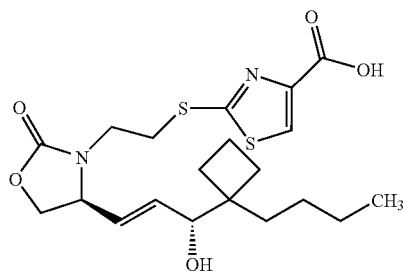

TLC: Rf0.20 (methylene chloride:methanol:acetic acid=18:1:1);
NMR (CDCl$_3$): δ 0.91 (t, J=6.59 Hz, 3H), 1.28 (m, 5H), 1.50 (m, 1H), 1.82 (m, 6H), 3.46 (m, 3H), 3.71 (m, 1H), 3.98 (m, 1H), 4.13 (m, 1H), 4.43 (m, 2H), 5.69 (m, 1H), 5.93 (dd, J=15.44, 5.77 Hz, 1H), 8.12 (s, 1H).

Example 32(2)

2-{[2-((4S)-4-{(1E,3R)-3-hydroxy-3-[1-(3-methoxypropyl)cyclobutyl]-1-propenyl}-2-oxo-1,3-oxazolidin-3-yl)ethyl]sulfanyl}-1,3-thiazole-4-carboxylic acid (Compound 32-2)

TLC: Rf0.24 (ethyl acetate:methanol:acetic acid=15:1:1);
NMR (CDCl$_3$): δ 1.74 (m, 10H) 3.53 (m, 9H) 3.97 (m, 1H) 4.13 (m, 1H) 3.94 (m, 2H) 4.47 (m, 2H) 5.72 (ddd, J=15.15, 8.74, 1.37 Hz, 1H) 6.06 (dd, J=15.38, 4.76 Hz, 1H) 8.10 (s, 1H).

Example 32(3)

2-[(2-{(4S)-4-[(1E,3R)-3-hydroxy-7-methoxy-4,4-dimethyl-1-heptenyl]-2-oxo-1,3-oxazolidin-3-yl}ethyl)sulfanyl]-1,3-thiazole-4-carboxylic acid (Compound 32-3)

TLC: Rf0.43 (methylene chloride:methanol:acetic acid=17:2:1);
NMR (CDCl$_3$): δ 0.81 (s, 3H), 0.88 (s, 3H), 1.30-1.71 (m, 4H), 3.39-3.67 (m, 9H), 3.92-4.06 (m, 2H), 4.39-4.52 (m, 2H), 5.70 (ddd, J=15.29, 8.24, 1.74 Hz, 1H), 6.06 (dd, J=15.29, 4.85 Hz, 1H), 8.09 (s, 1H).

Example 32(4)

2-{[2-((4S)-4-{(1E,3R)-3-hydroxy-3-[1-(2-phenyl-ethyl)cyclobutyl]-1-propenyl}-2-oxo-1,3-oxazolidin-3-yl)ethyl]sulfanyl}-1,3-thiazole-4-carboxylic acid (Compound 32-4)

TLC: Rf0.42 (methylene chloride:methanol=5:1);
NMR (CDCl$_3$): δ 1.56-2.13 (m, 8H) 2.64 (m, 2H) 3.36-3.54 (m, 3H) 3.60-3.76 (m, 1H) 3.97 (m, 1H) 4.24 (dd, J=5.58, 1.19 Hz, 1H) 4.36-4.49 (m, 2H) 5.73 (m, 1H) 5.97 (dd, J=15.47, 5.58 Hz, 1H) 7.13-7.22 (m, 3H) 7.28 (m, 2H) 8.09 (s, 1H).

Example 32(5)

2-{[2-((4S)-4-{(1E)-3-[1-(2-ethoxyethyl)cyclobutyl]-3-hydroxy-1-propenyl}-2-oxo-1,3-oxazolidin-3-yl)ethyl]sulfanyl}-1,3-thiazole-4-carboxylic acid (Compound 32-5)

TLC: Rf0.26 (methylene chloride:methanol=5:1);
NMR (CDCl$_3$): δ 1.21 (t, J=7.05 Hz, 3H) 1.55-1.98 (m, 6H) 2.00-2.16 (m, 2H) 3.35-3.75 (m, 8H) 3.93-4.05 (m, 1H) 4.08-4.17 (m, 1H) 4.36-4.49 (m, 2H) 5.65 (m, 1H) 5.94 (m, 1H) 8.10 and 8.11 (each s, total 1H).

Example 32(6)

2-[(2-{(2R)-2-[(1E)-4-(3-fluorophenoxy)-3-hydroxy-1-butenyl]-5-oxo-1-pyrrolidinyl}ethyl)sulfanyl]-1,3-thiazole-4-carboxylic acid (Compound 32-6)

TLC: Rf0.45 (ethyl acetate:methanol:acetic acid=5:1:1);
NMR (CDCl$_3$): δ 1.62-1.95 (m, 1H), 2.10-2.63 (m, 3H), 2.97-4.82 (m, 10H), 5.65-5.99 (m, 2H), 6.49-6.80 (m, 3H), 7.11-7.33 (m, 1H), 8.07 (s, 1H).

Example 32(7)

2-[(2-{(4S)-4-[(1E,3R)-3-hydroxy-4-methyl-4-phenyl-1-pentenyl]-2-oxo-1,3-oxazolidin-3-yl}ethyl)sulfanyl]-1,3-thiazole-4-carboxylic acid (Compound 32-7)

TLC: Rf0.14 (methylene chloride:methanol:acetic acid=18:1:1);
NMR (CDCl$_3$): δ 1.32 (s, 3H), 1.35 (s, 3H), 3.15-3.64 (m, 4H), 3.88 (dd, J=8.33, 7.05 Hz, 1H), 4.20-4.42 (m, 3H), 5.49 (ddd, J=15.29, 8.56, 1.10 Hz, 1H), 5.75 (dd, J=15.29, 6.13 Hz, 1H), 7.17-7.42 (m, 5H), 8.12 (s, 1H).

Example 32(8)

2-{[2-((4S)-4-{(1E,3R)-3-hydroxy-3-[1-(4-methyl-3-pentenyl)cyclobutyl]-1-propenyl}-2-oxo-1,3-oxazolidin-3-yl)ethyl]sulfanyl}-1,3-thiazole-4-carboxylic acid (Compound 32-8)

TLC: Rf0.41 (methylene chloride:methanol=5:1);
NMR (DMSO-D$_6$): δ 1.11-2.05 (m, 10H) 1.53 (s, 3H) 1.61 (s, 3H) 3.13-3.49 (m, 3H) 3.50-3.63 (m, 1H) 3.81-3.94 (m, 2H) 4.39 (dd, J=8.23, 8.23 Hz, 1H) 4.48 (m, 1H) 4.84 (m, 1H) 5.02 (m, 1H) 5.53 (dd, J=15.28, 8.60 Hz, 1H) 5.81 (dd, J=15.28, 6.50 Hz, 1H) 8.34 (s, 1H) 13.0 (br, 1H).

Example 32(9)

2-{[2-((4S)-4-{(1E,3R)-3-[1-(cyclohexylmethyl)cyclobutyl]-3-hydroxyl-1-propenyl}-2-oxo-1,3-oxazolidin-3-yl)ethyl]sulfanyl}-1,3-thiazole-4-carboxylic acid (Compound 32-9)

TLC: Rf0.56 (ethyl acetate:methanol=2:1);
NMR (CDCl$_3$): δ 0.79-2.07 (m, 19H) 3.35-3.80 (m, 4H) 3.93-4.06 (m, 1H) 4.22 (d, J=5.58 Hz, 1H) 4.35-4.52 (m, 2H) 5.64-5.80 (m, 1H) 5.98 (dd, J=15.46, 5.58 Hz, 1H) 8.12 (s, 1H).

Example 32(10)

2-{[2-((4S)-{(1E,3R)-3-hydroxy-3-[1-(2-methoxyethyl)cyclobutyl]-1-propenyl}-2-oxo-1,3-oxazolidin-3-yl)ethyl]sulfanyl}-1,3-thiazole-4-carboxylic acid (Compound 32-10)

TLC: Rf0.48 (methylene chloride:methanol:acetic acid=17:2:1);
NMR (CDCl$_3$): δ 1.55-2.13 (m, 8H), 3.35 (s, 3H), 3.37-3.75 (m, 6H), 3.94-4.06 (m, 1H), 4.10-4.16 (m, 1H), 4.34-4.51 (m, 2H), 5.66 (ddd, J=15.37, 8.42, 1.46 Hz, 1H), 5.94 (dd, J=15.37, 4.94 Hz, 1H), 8.11 (s, 1H).

Example 32(11)

2-{[2-((4S)-4-{(1E,3R)-3-hydroxy-3-[1-(4-methyl-pentyl)cyclobutyl]-1-propenyl}-2-oxo-1,3-oxazolidin-3-yl)ethyl]sulfanyl}-1,3-thiazol-4-carboxylic acid (Compound 32-11)

TLC: Rf0.47 (methylene chloride:methanol=5:1);
NMR (DMSO-D$_6$): δ 0.82 (d, J=6.59 Hz, 6H) 0.94-1.80 (m, 11H) 1.84-2.03 (m, 2H) 3.14-3.45 (m, 3H) 3.50-3.63 (m, 1H) 3.82 (m, 1H) 3.89 (dd, J=8.23, 6.40 Hz, 1H) 4.40 (dd, J=8.23, 8.23 Hz, 1H) 4.44-4.53 (m, 1H) 4.81 (d, J=4.21 Hz, 1H) 5.51 (dd, J=15.28, 8.69 Hz, 1H) 5.80 (dd, J=15.28, 6.68 Hz, 1H) 8.35 (s, 1H).

Example 32(12)

2-{[2-((4S)-4-{(1E,3R)-3-hydroxy-3-[1-(3-methyl-2-butenyl)cyclobutyl]-1-propenyl}-2-oxo-1,3-oxazolidin-3-yl)ethyl]sulfanyl}-1,3-thiazole-4-carboxylic acid (Compound 32-12)

TLC: Rf0.44 (methylene chloride:methanol=5:1);
NMR (DMSO-D$_6$): δ 1.43-1.76 (m, 4H) 1.54 (s, 3H) 1.67 (s, 3H) 1.78-1.96 (m, 3H) 2.04-2.19 (m, 1H) 3.15-3.46 (m, 3H) 3.51-3.65 (m, 1H) 3.81-3.94 (m, 2H) 4.39 (dd, J=8.23, 8.23 Hz, 1H) 4.43-4.53 (m, 1H) 4.83 (br, 1H) 5.17 (t, J=7.23 Hz, 1H) 5.51 (dd, J=15.28, 8.69 Hz, 1H) 5.83 (dd, J=15.28, 6.31 Hz, 1H) 8.34 (s, 1H).

Example 32(13)

2-{[2-((4S)-4{(1E,3R)-3-[1-(2-butynyl)cyclobutyl]-3-hydroxy-1-propenyl}-2-oxo-1,3-oxazolidin-3-yl)ethyl]sulfanyl}-1,3-thiazole-4-carboxylic acid (Compound 32-13)

TLC: Rf0.23 (methylene chloride:methanol=5:1);
NMR (DMSO-D$_6$): δ 1.56-2.11 (m, 10H) 2.25 (m, 1H) 3.19-3.45 (m, 3H) 3.51-3.64 (m, 1H) 3.90 (dd, J=8.32, 6.59

Hz, 1H) 3.95-4.02 (m, 1H) 4.38 (dd, J=8.32, 8.32 Hz, 1 H) 4.47 (m, 1H) 4.95 (d, J=4.21 Hz, 1H) 5.54 (dd, J=15.19, 8.69 Hz, 1H) 5.85 (dd, J=15.19, 6.22 Hz, 1H) 8.35 (s, 1H).

Example 32(14)

2-{[2-((4S)-4-{(1E,3R)-3-[1-(2-cyclohexylethyl)cyclobutyl]-3-hydroxy-1-propenyl}-2-oxo-1,3-oxazolidin-3-yl)ethyl]sulfanyl}-1,3-thiazole-4-carboxylic acid (Compound 32-14)

TLC: Rf0.23 (ethyl acetate:methanol=5:1);
NMR (CDCl$_3$): δ 0.56-2.04 (m, 21H) 3.31-3.82 (m, 6H) 3.90-4.04 (m, 1H) 4.06-4.18 (m, 1H) 4.33-4.51 (m, 2H) 5.68 (ddd, J=15.19, 8.55, 1.28 Hz, 1H) 5.91 (dd, J=15.19, 5.85 Hz, 1H) 8.11 (s, 1H).

Example 32(15)

2-[(2-{(4S)-4-[(1E,3R)-3-hydroxy-3-(1-isopentylcyclobutyl)-1-propenyl]-2-oxo-1,3-oxazolidin-3-yl}ethyl)sulfanyl]-1,3-thiazole-4-carboxylic acid (Compound 32-15)

TLC: Rf0.70 (methylene chloride:methanol=5:1);
NMR (CDCl$_3$): δ 0.88 (d, J=6.6 Hz, 3H), 0.89 (d, J=6.6 Hz, 3H) 1.05-2.07 (m, 11H) 3.37-3.56 (m, 3H) 3.66-3.78 (m, 1H) 3.98 (m, 1H) 4.10-4.17 (m, 1H) 4.36-4.49 (m, 2H) 5.68 (m, 1H) 5.92 (dd, J=15.28, 5.58 Hz, 1H) 8.12 (s, 1H).

Example 32(16)

2-{[2-(4S)-4-{(1E,3R)-3-[1-(3,3-dimethylbutyl)cyclobutyl]-3-hydroxy-1-propenyl}-2-oxo-1,3-oxazolidin-3-yl)ethyl]sulfanyl}-1,3-thiazole-4-carboxylic acid (Compound 32-16)

TLC: Rf0.46 (methylene chloride:methanol=5:1);
NMR (CDCl$_3$): δ 0.87 (s, 9H) 1.05-2.06 (m, 10H) 3.36-3.79 (m, 4H) 3.98 (m, 1H) 4.08-4.17 (m, 1H) 4.37-4.49 (m, 2H) 5.70 (m, 1H) 5.93 (dd, J=15.30, 5.70 Hz, 1H) 8.12 (s, 1H).

Example 32(17)

2-{[2-((4S)-4{(1E,3R)-3-[1-(5-fluoropentyl)cyclobutyl]-3-hydroxy-1-propenyl}-2-oxo-1,3-oxazolidin-3-yl)ethyl]sulfanyl}-1,3-thiazole-4-carboxylic acid (Compound 32-17)

TLC: Rf0.56 (ethyl acetate:methanol:acetic acid=15:1:1);
NMR (CDCl$_3$): δ 1.20-2.03 (m, 14H) 2.66-3.79 (m, 6H) 3.89-4.06 (m, 1H) 4.11-4.19 (m, 1H) 4.30-4.60 (m, 4H) 5.70 (dd, J=15.55, 9.00 Hz, 1H) 5.93 (dd, J=15.55, 5.31 Hz, 1H) 8.12 (s, 1H).

Example 32(18)

2-{[2-((4S)-4-{(1E,3R)-3-[1-(cyclopropylmethyl)cyclobutyl]-3-hydroxy-1-propenyl}-2-oxo-1,3-oxazolidin-3-yl)ethyl]sulfanyl}-1,3-thiazole-4-carboxylic acid (Compound 32-18)

TLC: Rf0.47 (ethyl acetate:methanol:acetic acid=15:1:1);
NMR (CDCl$_3$): δ 0.01-0.59 (m, 4H) 0.61-0.88 (m, 1H) 1.37 (d, J=6.00 Hz, 2H) 1.68-2.03 (m, 6H) 2.26-2.97 (m, 2H) 3.32-3.80 (m, 4H) 3.91-4.05 (m, 1H) 4.30 (dd, J=5.31, 1.37 Hz, 1H) 4.33-4.55 (m, 2H) 5.71 (ddd, J=15.37, 8.46, 1.37 Hz, 1H) 5.95 (dd, J=15.37, 5.31 Hz, 1H) 8.12 (s, 1H).

Example 33(1)-33(5)

By the same procedure as a series of reactions of Example 2→Example 3→Example 4→Example 5→Example 6→Example 7→Example 8 using (5R)-5-(hydroxymethyl)pyrrolidin-2-one or (4R)-4-(hydroxymethyl)-1-methylimidazolidin-2-one instead of the compound 1 and using a corresponding phosphonate instead of dimethyl (3,3-dimethyl-2-oxoheptyl)phosphonate, the following title compounds were obtained.

Example 33(1)

2-[(2-{(2R)-2-[(1E,3R)-4-(cyclohexyloxy)-3-hydroxy-1-butenyl]-5-oxo-1-pyrrolidinyl}ethyl)sulfanyl]-1,3-thiazole-4-carboxylic acid (Compound 33-1)

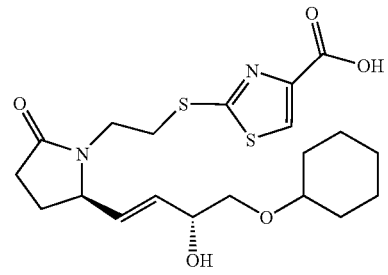

TLC: Rf0.41 (ethyl acetate:methanol:acetic acid=8:1:1);
NMR (CDCl$_3$): δ 1.26 (m, 5H) 1.53 (m, 1H) 1.79 (m, 5H) 2.36 (m, 3H) 3.52 (m, 7H) 4.20 (m, 4H) 5.71 (m, 2H) 8.10 (s, 1H).

Example 33(2)

2-[(2-{(2R)-2-[(1E)-3-hydroxy-4-(4-methylphenoxy)-1-butenyl]-5-oxo-1-pyrrolidinyl}ethyl)sulfanyl]-1,3-thiazole-4-carboxylic acid (Compound 33-2)

TLC: Rf0.22 (ethyl acetate:methanol:acetic acid=8:1:1);
NMR (CDCl$_3$): δ 1.71-1.91 (m, 1H) 2.15-2.60 (m, 6H) 3.14-4.28 (m, 10H) 4.49-4.65 (m, 1H) 5.67-5.94 (m, 2H) 6.79 (d, J=8.24 Hz, 2H) 7.08 (d, J=8.60 Hz, 2H) 8.06 (s, 1H).

Example 33(3)

2-[(2-{(2R)-2-[(1E)-3-hydroxy-4-(2-methylphenoxy)-1-butenyl]-5-oxo-1-pyrrolidinyl}ethyl)sulfanyl]-1,3-thiazole-4-carboxylic acid (Compound 33-3)

TLC: Rf0.26 (ethyl acetate:methanol:acetic acid=8:1:1);
NMR (CDCl$_3$): δ 1.72-1.88 (m, 1H) 2.15-2.58 (m, 6H) 3.29-3.40 (m, 2H) 3.41-3.59 (m, 1H) 3.75-4.05 (m, 3H) 4.15-4.26 (m, 1H) 4.53-4.66 (m, 1H) 5.69-5.84 (m, 1H) 5.84-5.95 (m, 1H) 6.79 (d, J=8.60 Hz, 1H) 6.89 (t, J=7.32 Hz, 1H) 7.15 (t, J=6.50 Hz, 2H) 8.05 (d, J=2.01 Hz, 1H).

Example 33(4)

2-[(2-{(5S)-5-[(1E,3S,5S)-3-hydroxy-5-methyl-1-nonenyl]-3-methyl-2-oxo-1-imidazolidinyl}ethyl)sulfanyl]-1,3-thiazole-4-carboxylic acid (Compound 33-4)

TLC: Rf0.19 (methylene chloride:methanol:acetic acid=18:1:1);
NMR (CDCl$_3$): δ 0.90 (m, 6H), 1.31 (m, 9H), 2.80 (s, 3H), 3.01 (dd, J=8.79, 8.06 Hz, 1H), 3.39 (m, 4H), 3.66 (ddd, J=13.68, 9.20, 5.86 Hz, 1H), 4.09 (q, J=8.30 Hz, 1H), 4.26 (m, 1H), 5.58 (ddd, J=15.38, 8.74, 0.82 Hz, 1H), 5.83 (dd, J=15.38, 6.22 Hz, 1H), 8.08 (s, 1H).

Example 33(5)

2-[(2-{(5S)-5-[(1E)-3-hydroxy-4-phenoxy-1-butenyl]-3-methyl-2-oxo-1-imidazolidinyl}ethyl)sulfanyl]-1,3-thiazole-4-carboxylic acid (Compound 33-5)

TLC: Rf0.13 (methylene chloride:methanol:acetic acid=18:1:1);
NMR (CDCl$_3$): δ 2.80 (s, 3H), 3.03 (m, 1H), 3.35 (m, 2H), 3.50 (m, 2H), 3.65 (m, 1H), 3.91 (dd, J=9.25, 6.87 Hz, 1H), 4.02 (m, 1H), 4.13 (m, 1H), 4.59 (m, 1H), 5.80 (m, 1H), 5.93 (dd, J=15.38, 5.13 Hz, 1H), 6.89 (m, 2H), 6.99 (m, 1H), 7.30 (m, 2H), 8.04 and 8.05 (each s, totally 1H).

Example 34(1)-34(16)

By the same procedure as a series of reactions of Example 1→Example 2→Example 3→Example 4→Example 5→Example 6→Example 7→Example 8 using D-threonine methyl ester hydrochloride instead of D-serine methyl ester hydrochloride and using a corresponding phosphonate instead of dimethyl (3,3-dimethyl-2-oxoheptyl)phosphonate, the following title compounds were obtained.

Example 34(1)

2-[(2-{(4S,5S)-4-[(1E)-3-hydroxy-4,4-dimethyl-1-octenyl]-5-methyl-2-oxo-1,3-oxazolidin-3-yl}ethyl)sulfanyl]-1,3-thiazole-4-carboxylic acid (Compound 34-1)

TLC: Rf0.69 (ethyl acetate:methanol:acetic acid=8:1:1);
NMR (CDCl$_3$): δ 0.88 (m, 9H) 1.22 (m, 6H) 1.38 (d, J=6.22 Hz, 3H) 3.50 (m, 4H) 3.89 (m, 2H) 4.23 (m, 1H) 5.59 (m, 1H) 5.95 (m, 1H) 8.11 (m, 1H).

Example 34(2)

2-{[2-((4S,5S)-4-{(1E)-3-[1-(4-fluorobutyl)cyclobutyl]-3-hydroxy-1-propenyl}-5-methyl-2-oxo-1,3-oxazolidin-3-yl)ethyl]sulfanyl}-1,3-thiazole-4-carboxylic acid (Compound 34-2)

TLC: Rf0.39 (ethyl acetate:methanol:acetic acid=15:1:1);
NMR (CDCl$_3$): δ 1.63 (m, 15H) 3.93 (m, 11H) 5.67 (m, 1H) 5.95 (m, 1H) 8.10 (m, 1H).

Example 34(3)

2-[(2-{(4S,5S)-4-[(1E)-3-hydroxy-4-phenoxy-1-butenyl]-5-methyl-2-oxo-1,3-oxazolidin-3-yl}ethyl)sulfanyl]-1,3-thiazole-4-carboxylic acid (Compound 34-3)

TLC: Rf0.36 (ethyl acetate:methanol:acetic acid=15:1:1);
NMR (CDCl$_3$): δ 1.38 (d, J=6.22 Hz, 3H) 3.66 (m, 9H) 4.26 (m, 1H) 4.60 (m, 1H) 5.79 (m, 1H) 6.01 (m, 1H) 6.88 (d, J=8.06 Hz, 2H) 6.99 (m, 1H) 7.29 (m, 2H) 8.07 (m, 1H).

Example 34(4)

2-[(2-{(4S,5S)-4-[(1E)-3-(1-butylcyclobutyl)-3-hydroxy-1-propenyl]-5-methyl-2-oxo-1,3-oxazolidin-3-yl}ethyl)sulfanyl]-1,3-thiazole-4-carboxylic acid (Compound 34-4)

TLC: Rf0.21 (methylene chloride:methanol:acetic acid=18:1:1);
NMR (CDCl$_3$): δ 0.91 (m, 3H), 1.28 (m, 5H), 1.38 (m, 3H), 1.52 (m, 1H), 1.83 (m, 6H), 3.52 (m, 4H), 3.88 (dd, J=8.60, 8.24 Hz, 1H), 4.20 (m, 2H), 5.65 (m, 1H), 5.93 (m, 1H), 8.12 and 8.11 (each s, totally 1H).

Example 34(5)

2-[(2-{(4S,5S)-4-[(1E)-8-fluoro-3-hydroxy-4,4-dimethyl-1-octenyl]-5-methyl-2-oxo-1,3-oxazolidin-3-yl}ethyl)sulfanyl]-1,3-thiazole-4-carboxylic acid (Compound 34-5)

TLC: Rf0.38 (ethyl acetate:methanol:acetic acid=15:1:1);
NMR (CDCl$_3$): δ 0.88 (m, 6H) 1.35 (m, 7H) 1.65 (m, 2H) 3.52 (m, 4H) 3.91 (m, 2H) 4.23 (m, 1H) 4.38 (m, 1H) 4.54 (m, 1H) 5.61 (m, 1H) 5.96 (m, 1H) 8.11 (m, 1H).

Example 34(6)

2-{[2-((4S,5S)-{(1E)-3-hydroxy-3-[1-(3-methoxypropyl)cyclobutyl]-1-propenyl}-5-methyl-2-oxo-1,3-oxazolidin-3-yl)ethyl]sulfanyl}-1,3-thiazole-4-carboxylic acid (Compound 34-6)

TLC: Rf0.37 (ethyl acetate:methanol:acetic acid=15:1:1);
NMR (CDCl$_3$): δ 1.69 (m, 13H) 3.53 (m, 9H) 3.97 (m, 1H) 4.20 (m, 2H) 5.66 (m, 1H) 6.06 (m, 1H) 8.10 (s, 1H).

Example 34(7)

2-[(2-{(4S,5S)-4-[(1E)-3-hydroxy-7-methoxy-4,4-dimethyl-1-heptenyl]-5-methyl-2-oxo-1,3-oxazolidin-3-yl}ethyl)sulfanyl]-1,3-thiazole-4-carboxylic acid (Compound 34-7)

TLC: Rf0.22 (methylene chloride:methanol:acetic acid=18:1:1);
NMR (CDCl$_3$): δ 0.82 and 0.85 (each s, totally 3H), 0.87 and 0.88 (each s, totally 3H), 1.36 and 1.37 (each d, J=6.22 Hz, totally 3H), 1.40-1.69 (m, 4H), 3.41 and 3.43 (each s, totally 3H), 3.44-3.67 (m, 6H), 3.86-4.01 (m, 2H), 4.16-4.30 (m, 1H), 5.50-5.73 (m, 1H), 5.96-6.11 (m, 1H), 8.09 and 8.10 (each s, totally 1H).

Example 34(8)

2-{[2-((4S,5S)-4-{(1E)-3-[1-(2-ethoxyethyl)cyclobutyl]-3-hydroxy-1-propenyl}-5-methyl-2-oxo-1,3-oxazolidin-3-yl)ethyl]sulfanyl}-1,3-thiazole-4-carboxylic acid (Compound 34-8)

TLC: Rf0.40 (methylene chloride:methanol=4:1);
NMR (CDCl$_3$): δ 1.20 and 1.21 (each t, J=7.2 Hz, total 3H) 1.38 (d, J=6.22 Hz, 3H) 1.56-2.16 (m, 8H) 3.17-3.74 (m, 8H) 3.89 (m, 1H) 4.12-4.17 (m, 1H) 4.24 (m, 1H) 5.62 (m, 1H) 5.95 (m, 1H) 8.103 and 8.107 (each s, total 1H).

Example 34(9)

2-[(2-{(4S,5S)-4-[(1E)-3-(1-benzylcyclobutyl)-3-hydroxy-1-propenyl]-5-methyl-2-oxo-1,3-oxazolidin-3-yl}ethyl)sulfanyl]-1,3-thiazole-4-carboxylic acid (Compound 34-9)

TLC: Rf0.27 (ethyl acetate:methanol:water=40:10:1);
NMR (DMSO-D$_6$): δ 1.20-2.02 (m, 9H) 2.40-2.55 (m, 1H) 2.68-2.84 (m, J=13.00 Hz, 1H) 3.18-3.35 (m, 1H) 3.38-3.50 (m, 2H) 3.49-3.65 (m, 1H) 3.84-3.90 (m, 1H) 3.96-4.09 (m, 1H) 4.16-4.29 (m, 1H) 4.87-5.01 (m, 1H) 5.46-5.62 (m, 1H) 5.93-6.14 (m, 1H) 6.95-7.43 (m, 5H) 8.08-8.53 (m, 1H) 12.75-13.38 (m, 1H).

Example 34(10)

2-{[2-((4S,5S)-4-{(1E)-3-hydroxy-3-[1-(4-methoxybenzyl)cyclobutyl]-1-propenyl}-5-methyl-2-oxo-1,3-oxazolidin-3-yl)ethyl]sulfanyl}-1,3-thiazole-4-carboxylic acid (Compound 34-10)

TLC: Rf0.27 (ethyl acetate:methanol:water=40:10:1);
NMR (DMSO-D$_6$): δ 1.21-2.01 (m, 9H) 2.41 (d, J=13.55 Hz, 1H) 2.63-2.77 (m, 1H) 3.20-3.37 (m, 1H) 3.38-3.47 (m, 2H) 3.50-3.63 (m, 1H) 3.71 (s, 3H) 3.81-3.90 (m, 1H) 3.95-4.10 (m, 1H) 4.15-4.29 (m, 1H) 4.84-4.97 (m, 1H) 5.44-5.61 (m, 1H) 5.92-6.12 (m, 1H) 6.83 (d, J=8.60 Hz, 2H) 7.08 (d, J=8.60 Hz, 2H) 8.12-8.55 (m, 1H) 12.75-13.38 (m, 1H).

Example 34(11)

2-({2-[(4S,5S)-4-((1E)-3-hydroxy-3-{1-[(2E)-2-pentenyl]cyclobutyl}-1-propenyl)-5-methyl-2-oxo-1,3-oxazolidin-3-yl]ethyl}sulfanyl)-1,3-thiazole-4-carboxylic acid (Compound 34-11)

TLC: Rf0.28 (methylene chloride:methanol:acetic acid=18:1:1);
NMR (CDCl$_3$): δ 0.98 (t, J=7.41 Hz, 3H), 1.39 (d, J=6.22 Hz, 3H), 1.64-2.37 (m, 10H), 3.31-3.73 (m, 4H), 3.85-3.96 (m, 1H), 4.07-4.32 (m, 2H), 5.40-5.57 (m, 2H), 5.57-5.71 (m, 1H), 5.88-6.01 (m, 1H), 8.11 and 8.12 (each s, 3H).

Example 34(12)

2-{[2-((4S,5S)-4-{(1E)-3-hydroxy-3-[1-(3-methoxypropyl)cyclopentyl]-1-propenyl}-5-methyl-2-oxo-1,3-oxazolidin-3-yl)ethyl]sulfanyl}-1,3-thiazole-4-carboxylic acid (Compound 34-12)

TLC: Rf0.41 (ethyl acetate:methanol:acetic acid=15:1:1);
NMR (CDCl$_3$): δ 1.23-1.74 (m, 15H) 3.37-3.69 (m, 9H) 3.90-4.29 (m, 3H) 5.48-5.77 (m, 1H) 6.03-6.17 (m, 1H) 8.09 (s, 1H).

Example 34(13)

2-{[2-((4S,5S)-4-{(1E,3R)-3-hydroxy-3-[1-(3-methoxypropyl)cyclobutyl]-1-propenyl}-5-methyl-2-oxo-1,3-oxazolidin-3-yl)ethyl]sulfanyl}-1,3-thiazole-4-carboxylic acid (Compound 34-13)

TLC: Rf0.37 (ethyl acetate:methanol:acetic acid=15:1:1);
NMR (CDCl$_3$): δ 1.21-2.08 (m, 13H) 3.33-3.68 (m, 11H) 3.85-4.02 (m, 1H) 4.07-4.28 (m, 2H) 5.69 (dd, J=15.46, 9.15 Hz, 1H) 6.06 (dd, J=15.46, 4.30 Hz, 1H) 8.07 (s, 1H).

Example 34(14)

2-{[2-((4S,5S)-4-{(1E)-3-hydroxy-3-[1-(4-methyl-3-pentenyl)cyclobutyl]-1-propenyl}-5-methyl-2-oxo-1,3-oxazolidin-3-yl)ethyl]sulfanyl}-1,3-thiazole-4-carboxylic acid (Compound 34-14)

TLC: Rf0.22 (methylene chloride:methanol=5:1);
NMR (CDCl$_3$): δ 1.21-2.13 (m, 10H) 1.37 and 1.38 (each d, J=6.3 Hz, total 3H) 1.61 (s, 3H) 1.69 (m, 3H) 3.30-3.71 (m, 4H) 3.89 (dd, J=8.32 Hz, 1H) 4.12-4.31 (m, 2H) 5.07 (m, 1H) 5.58-5.73 (m, 1H) 5.88-5.99 (m, 1H) 8.10 and 8.11 (each s, total 1H).

Example 34(15)

2-{[2-((4S,5S)-4-{(1E)-3-hydroxy-3-[1-(2-pentynyl)cyclobutyl]-1-propenyl}-5-methyl-2-oxo-1,3-oxazolidin-3-yl)ethyl]sulfanyl}-1,3-thiazole-4-carboxylic acid (Compound 34-15)

TLC: Rf0.21 (methylene chloride:methanol=5:1);
NMR (CDCl$_3$): δ 1.13 (t, J=7.50 Hz, 3H) 1.39 (d, J=6.22 Hz, 3H) 1.69-2.41 (m, 10H) 3.30-3.72 (m, 4H) 3.89 (m, 1H) 4.16-4.34 (m, 2H) 5.65-5.77 (m, 1H) 5.94 (dd, J=15.3, 5.1 Hz, 1H) 8.10 and 8.11 (each s, total 1H).

Example 34(16)

2-{[2-((4S,5S)-4-{(1E)-3-hydroxy-3-[1-(4,4,4-trifluorobutyl)cyclobutyl]-1-propenyl}-5-methyl-2-oxo-1,3-oxazolidin-3-yl]ethyl]sulfanyl}-1,3-thiazole-4-carboxylic acid (Compound 34-16)

TLC: Rf0.52 (ethyl acetate:methanol:acetic acid=15:1:1);
NMR (CDCl$_3$): δ 1.31-2.69 (m, 17H) 3.31-3.75 (m, 4H) 3.83-3.95 (m, 1H) 4.06-4.32 (m, 2H) 5.59-5.79 (m, 1H) 5.85-6.02 (m, 1H) 8.12 (s, 1H).

Example 35

(1S,4R,5R)-4-({[tert-butyl(dimethyl)silyl]oxy}methyl)-3-azabicyclo[3.1.0]hexan-2-one (Compound 35)

To a solution of the compound prepared by the Reaction A in Example 13 (690 mg) in methylene chloride (10.0 mL) was added dropwise trifluoroacetic acid (0.480 mL) at 0° C. and the solution was stirred for 3 hours. An aqueous saturated sodium bicarbonate solution was added to the reaction solution, which was extracted with ethyl acetate. The reaction solution was washed with water and brine, dried over anhydrous sodium sulfate and concentrated to give the title compound (487 mg) having the following physical data TLC: Rf0.38 (ethyl acetate);
NMR (CDCl$_3$): δ 0.07 (s, 6H) 0.68-0.77 (m, 1H) 0.90 (s, 9H) 1.06-1.20 (m, 1H) 1.70-1.87 (m, 2H) 3.47-3.68 (m, 3H) 5.31 (s, 1H).

Example 36

2-[(2-{(1R,2S,5S)-2-[(1E,3S,5S)-3-hydroxy-5-methyl-1-nonenyl]-4-oxo-3-azabicyclo[3.1.0]hex-3-yl}ethyl)sulfanyl]-1,3-thiazole-4-carboxylic acid (Compound 36)

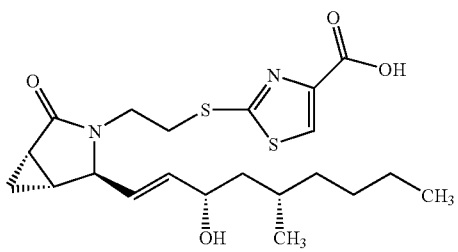

By the same procedure as a series of reactions of the Reaction B of Example 2→Example 3→Example 4→Example 5→Example 6→Example 7→Example 8 using the compound 35 instead of the compound prepared by the Reaction A in Example 2 and using dimethyl [(4S)-4-methyl-2-oxooctyl]phosphonate instead of dimethyl (3,3-dimethyl-2-oxoheptyl)phosphonate, the title compound having the following physical data was obtained.

TLC: Rf0.25 (ethyl acetate:methanol:acetic acid=15:1:1);
NMR (CDCl$_3$): δ 0.58 (m, 1H) 0.89 (m, 7H) 1.25 (m, 9H) 1.74 (m, 1H) 1.99 (m, 1H) 3.42 (m, 6H) 4.01 (dd, J=8.51 Hz, 1H) 4.25 (m, 1H) 5.57 (dd, J=15.65, 8.51 Hz, 1H) 5.83 (dd, J=15.65, 6.30 Hz, 1H) 8.09 (s, 1H).

Example 37

Ethyl 3-hydroxy-3-methyloctanoate (Compound 37)

To a solution of 2-heptanone (10.1 mL) in 1,4-dioxane (150 mL) were added ethyl bromoacetate (9.6 mL), zinc (8.5 g) and iodine (3.7 g) at room temperature and the solution was sonicated. After 2 hours 1N hydrochloric acid was added dropwise to the reaction solution, which was extracted with ethyl acetate. The organic layer was washed with water and brine, dried over anhydrous magnesium sulfate and concentrated. The obtained residue purified by flush column chromatography (n-hexane:ethyl acetate=15:1), to give the title compound (13.9 g) having the following physical data.

TLC: Rf0.31 (n-hexane:ethyl acetate=7:1);
NMR (CDCl$_3$): δ 0.89 (t, J=6.77 Hz, 3H) 1.14-1.60 (m, 14H) 2.43 (d, J=16.50 Hz, 1H) 2.51 (d, J=16.50 Hz, 1H) 3.09-3.98 (m, 1H) 4.18 (q, J=7.14 Hz, 2H).

Example 38

3-methyl-1,3-octandiol (Compound 38)

A solution of the compound 37 (13.86 g) in tetrahydrofuran (100 mL) was added dropwise to a suspension of lithium aluminum hydride (3.9 g) in tetrahydrofuran (100 mL) at 0° C. After 35 minutes, to the reaction solution was added ethyl acetate at 0° C. until foam was lost and 5N hydrochloric acid (20 mL) was added dropwise thereto. The solution temperature was risen to room temperature and the solution was stirred overnight. The reaction solution was dried over anhydrous magnesium sulfate, filtrated through Celite (Brand name) and concentrated. The obtained residue was purified by flush column chromatography (n-hexane:ethyl acetate=1:1), to give the title compound (10.31 g) having the following physical data.

TLC: Rf0.62 (ethyl acetate);
NMR (CDCl$_3$): δ 0.78-0.99 (m, 3H) 1.13-1.43 (m, 9H) 1.43-1.59 (m, 2H) 1.59-1.88 (m, 2H) 2.11-2.76 (m, 2H) 3.69-4.02 (m, 2H).

Example 39

3-methyl-1-[(1-phenyl-1H-tetrazol-5-yl)thio]octan-3-ol (Compound 39)

To a solution of the compound 38 (8.05 g) in toluene (98 mL) were added tetrabutylammonium bromide (1.62 g) and 2N sodium hydroxide (98 mL) at 0° C. and was added dropwise a suspension of tosyl chloride (10.5 g) in toluene (40 mL). The solution temperature was risen to room temperature and the solution was stirred for 1 hour. A solution of 1-phenyl-1H-tetrazole-5-thiol (10.74 g) in toluene was added thereto and the solution was stirred at 60° C. for 3.5 hours. The reaction solution was extracted with tert-butoxymethyl. The organic layer was washed with brine, dried over anhydrous magnesium sulfate and concentrated. The obtained residue was purified by Yamazen Parallel Prep (Brand name; column: 3 L, inject column: 2 L, n-hexane:ethyl acetate=81:19) to give the title compound (14.15 g) having the following physical data.

TLC: Rf0.39 (n-hexane:ethyl acetate=2:1);
NMR (CDCl$_3$): δ 0.90 (t, J=7.50 Hz, 3H) 1.25 (s, 3H) 1.27-1.42 (m, 6H) 1.43-1.57 (m, 2H) 1.65 (s, 1H) 1.95-2.04 (m, 2H) 3.36-3.57 (m, 2H) 7.40-7.73 (m, 5H).

Example 40

3-methyl-1-[(1-phenyl-1H-tetrazol-5-yl)sulfonyl]octan-3-ol (Compound 40)

To a solution of the compound 39 (14.0 g) in methylene chloride (200 mL) was added metachloro perbenzoic acid (27.3 g) at 0° C. The solution temperature was risen to room temperature and the solution was stirred overnight. An aqueous saturated sodium bicarbonate was added to the reaction solution, which was concentrated and extracted with ethyl acetate. The organic layer was washed with an aqueous saturated sodium bicarbonate solution and brine, dried over anhydrous magnesium sulfate and concentrated to give the title compound (15.4 g) having the following physical data
TLC: Rf0.42 (n-hexane:ethyl acetate=2:1);
NMR (CDCl$_3$): δ 0.90 (t, J=6.00 Hz, 3H) 1.24 (s, 3H) 1.27-1.39 (m, 6H) 1.42-1.79 (m, 3H) 1.93-2.26 (m, 2H) 3.75-3.99 (m, 2H) 7.42-7.87 (m, 5H).

Example 41

5-({3-methyl-3-[(trimethylsilyl)oxy]octyl}sulfonyl)-1-phenyl-1H-tetrazole (Compound 41)

To a solution of the compound 39 (15.4 g) in methylene chloride (87 mL) were added imidazole (8.92 g), trimethylsilyl chloride (11.1 mL) at 0° C. and the solution was stirred for 1 hour. Water was added to the reaction solution, which was extracted with ethyl acetate. The organic layer was washed with brine, dried over anhydrous magnesium sulfate and concentrated. The obtained residue was purified by flush column chromatography (n-hexane:ethyl acetate=25:1), to give the title compound (16.95 g) having the following physical data.
TLC: Rf0.43 (n-hexane:ethyl acetate=7:1);
NMR (CDCl$_3$): δ 0.12 (s, 9H) 0.90 (t, J=6.00 Hz, 3H) 1.14-1.39 (m, 9H) 1.41-1.58 (m, 2H) 1.84-2.20 (m, 2H) 3.63-3.94 (m, 2H) 7.46-7.86 (m, 5H).

Example 42

Butyl 2-({2-[(4R,5S)-4-formyl-5-methyl-2-oxo-1,3-oxazolidin-3-yl]ethyl}thio)-1,3-thiazole-4-carboxylate (Compound 42)

By the same procedure as a series of reactions of Example 1→Example 2→Example 3→Example 4→Example 5 using D-threonine methyl ester hydrochloride instead of D-serine methyl ester hydrochloride and using butyl 2-bromo-1,3-thiazole-4-carboxylate instead of ethyl 2-bromo-1,3-thiazole-4-carboxylate, the title compound having the following physical data was obtained.
TLC: Rf0.53 (ethyl acetate).

Example 43

Butyl 2-{[2-((4S,5S)-5-methyl-4-{(1E)-4-methyl-4-[(trimethylsilyl)oxy]-1-nonenyl}-2-oxo-1,3-oxazolidin-3-yl)ethyl]thio}-1,3-thiazole-4-carboxylate (Compound 43)

To a solution of the compound 41 (10.1 g) in dimethoxyethane (79 mL) was slowly added dropwise potassium hexamethyldisilazide (0.5M in toluene, 47.5 mL) at −78° C. and the solution was stirred at −78° C. for 54 minutes. To the reaction solution was slowly added dropwise a solution of the compound 42 (9.84 g) in dimethoxyethane (79 mL) and the solution was stirred at −78° C. for 25 minutes. The solution temperature was risen to 0° C. and the solution was stirred for 50 minutes. To the reaction solution was added an aqueous saturated sodium bicarbonate solution and the solution was extracted with ethyl acetate. The organic layer was washed with an aqueous saturated sodium bicarbonate solution and brine, and dried over anhydrous magnesium sulfate. The reaction solution was filtrated through Celite (Brand name) and concentrated. The obtained residue was purified by Yamazen Parallel Prep (Brand name; column: 3 L, inject column: 2 L, n-hexane:ethyl acetate=84:16) to give the title compound (6.62 g) having the following physical data.
TLC: Rf0.47 (n-hexane:ethyl acetate=2:1);
NMR (CDCl$_3$): δ 0.09 (s, 9H) 0.89 (t, J=6.95 Hz, 3H) 0.97 (t, J=7.32 Hz, 3H) 1.07-1.17 (m, 3H) 1.17-1.54 (m, 13H) 1.63-1.86 (m, 2H) 2.08-2.27 (m, 2H) 3.34-3.74 (m, 4H) 3.87 (dd, J=9.06, 7.68 Hz, 1H) 4.11-4.25 (m, 1H) 4.33 (t, J=6.68 Hz, 2H) 5.29 (dd, J=15.28, 9.06 Hz, 1H) 5.68-5.94 (m, 1H) 8.00 (s, 1H).

Example 44

Butyl 2-[(2-{(4S,5S)-4-[(1E)-4-hydroxy-4-methyl-1-nonenyl]-5-methyl-2-oxo-1,3-oxazolidin-3-yl}ethyl)thio]-1,3-thiazole-4-carboxylate (Compound 44)

To a solution of the compound 43 (6.53 g) in ethyl acetate (114 mL) was slowly added dropwise 4N hydrogen chloride/ethyl acetate solution (14 mL) at 0° C. and the solution was stirred for 10 minutes. An aqueous saturated sodium bicarbonate solution was slowly added dropwise to the reaction solution, which was extracted with ethyl acetate. The organic layer was washed with an aqueous saturated sodium bicarbonate solution and brine, dried over anhydrous magnesium sulfate and concentrated. The obtained residue was purified by Yamazen Parallel Prep (Brand name; column: 3 L, inject column: 2 L, n-hexane:ethyl acetate=40:60) to give the title compound (3.81 g) having the following physical data.
TLC: Rf0.32 (n-hexane:ethyl acetate=1:1);
NMR (CDCl$_3$): δ 0.81-0.92 (m, 3H) 0.97 (t, J=7.41 Hz, 3H) 1.07-1.15 (m, 3H) 1.15-1.53 (m, 13H) 1.56-1.84 (m, 3H) 2.12-2.32 (m, 2H) 3.35-3.75 (m, 4H) 3.91 (t, J=8.97 Hz, 1H) 4.14-4.26 (m, 1H) 4.33 (t, J=6.77 Hz, 2H) 5.36 (ddd, J=14.73, 8.97, 0.64 Hz, 1H) 5.97 (dt, J=14.73, 7.14 Hz, 1H) 7.99 (s, 1H).

Example 45

2-[(2-{(4S,5S)-4-[(1E)-4-hydroxy-4-methyl-1-nonenyl]-5-methyl-2-oxo-1,3-oxazolidin-3-yl}ethyl)sulfanyl]-1,3-thiazole-4-carboxylic acid (Compound 45)

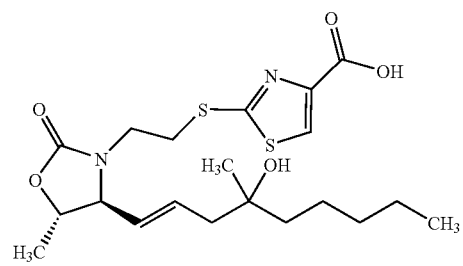

To a solution of the compound 44 (3.7 g) in methanol (37 mL) was added dropwise 2N aqueous sodium hydroxide solution (11 mL) at 0° C. The solution temperature was risen to room temperature and the solution was stirred for 45 minutes. After the reaction solution was cooled to 0° C., 2N hydrochloric acid was added thereto and the solution was extracted with ethyl acetate. The organic layer was washed with water and brine, dried over anhydrous magnesium sulfate and concentrated. The obtained residue was purified by flush column chromatography (n-hexane:ethyl acetate=1:1) to give the title compound (2.95 g) having the following physical data.

TLC: Rf0.31 (ethyl acetate:methanol:acetic acid=15:1:1);
NMR (CDCl$_3$): δ 0.69-1.02 (m, 3H), 0.99-1.63 (m, 14H), 2.13-2.43 (m, 2H), 3.27-3.58 (m, 3H), 3.58-3.74 (m, 1H), 3.82-3.94 (m, 1H), 3.97-4.81 (m, 3H), 5.24-5.47 (m, 1H), 5.81-6.19 (m, 1H), 7.89-8.26 (m, 1H).

Example 45(1)-45(24)

By the same procedure as a series of reactions of Example 39→Example 40→Example 41→Example 42→Example 43→Example 44→Example 45 using a corresponding alcohol derivative instead of the compound 38 and using the compound 42 or the compound 5, the following title compound were obtained.

Example 45(1)

2-[(2-{(4S)-4-[(1E,4S)-4-(1-ethylcyclobutyl)-4-hydroxy-1-butenyl]-2-oxo-1,3-oxazolidin-3-yl}ethyl)sulfanyl]-1,3-thiazole-4-carboxylic acid (Compound 45-1)

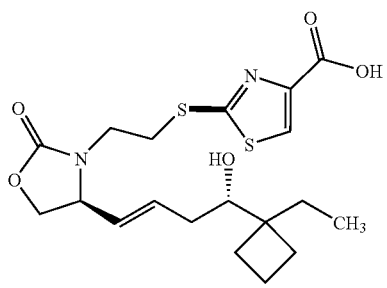

TLC: Rf0.44 (ethyl acetate:methanol:acetic acid=8:1:1);
NMR (CDCl$_3$): δ 0.91 (t, J=7.51 Hz, 3H), 1.13-2.39 (m, 10H), 3.25-4.67 (m, 8H), 4.91-6.53 (m, 4H), 8.12 (s, 1H).

Example 45(2)

2-[(2-{(4S)-4-[(1E)-4-hydroxy-4-methyl-1-nonenyl]-2-oxo-1,3-oxazolidin-3-yl}ethyl)sulfanyl]-1,3-thiazole-4-carboxylic acid (Compound 45-2)

TLC: Rf0.48 (ethyl acetate:methanol:acetic acid=15:1:1);
NMR (CDCl$_3$): δ 0.68-1.02 (m, 3H), 1.02-1.64 (m, 11H), 2.09-2.47 (m, 2H), 2.73-5.07 (m, 9H), 5.24-5.57 (m, 1H), 5.76-6.24 (m, 1H), 7.79-8.33 (m, 1H).

Example 45(3)

2-[(2-{(4S)-4-[(1E)-5-cyclohexyl-4-hydroxy-4-methyl-1-pentenyl]-2-oxo-1,3-oxazolidin-3-yl}ethyl)sulfanyl]-1,3-thiazole-4-carboxylic acid (Compound 45-3)

TLC: Rf0.50 (ethyl acetate:methanol:acetic acid=15:1:1);
NMR (CDCl$_3$): δ 0.78-1.90 (m, 16H) 2.11-2.44 (m, 2H) 2.83 (s, 2H) 3.30-3.79 (m, 4H) 3.87-4.04 (m, 1H) 4.28-4.50 (m, 2H) 5.38 (dd, J=14.91, 8.69 Hz, 1H) 5.5-6.11 (m, 1H) 8.09 (s, 1H).

Example 45(4)

2-[(2-{(4S)-2-oxo-4-[(1E)-8,8,8-trifluoro-4-hydroxy-4-methyl-1-octenyl]-1,3-oxazolidin-3-yl}ethyl)sulfanyl]-1,3-thiazole-4-carboxylic acid (Compound 45-4)

TLC: Rf0.42 (ethyl acetate:methanol:acetic acid=15:1:1);
NMR (CDCl$_3$): δ 1.18 (s, 3H) 1.43-1.79 (m, 4H) 1.92-2.40 (m, 4H) 2.87 (s, 2H) 3.34-3.77 (m, 4H) 3.88-4.04 (m, 1H) 4.29-4.55 (m, 2H) 5.43 (dd, J=15.28, 8.32 Hz, 1H) 5.90-6.12 (m, 1H) 8.10 (s, 1H).

Example 45(5)

2-[(2-{(4S,5S)-4-[3-(1-hydroxycyclohexyl)-1-propenyl]-5-methyl-2-oxo-1,3-oxazolidin-3-yl}ethyl)sulfanyl]-1,3-thiazole-4-carboxylic acid (Compound 45-5)

TLC: Rf0.43 (methylene chloride:methanol=4:1);
NMR (CDCl$_3$): δ 1.16-1.71 (m, 13H) 2.22-2.40 (m, 2H) 3.28-3.75 (m, 4H) 3.90-3.85 (m, 1H) 4.01-4.46 (m, 2H) 5.35-5.52 (m, 1H) 5.90-6.15 (m, 1H) 8.10 (s, 1H).

Example 45(6)

2-[(2-{(4S,5S)-4-[4-hydroxy-7-methoxy-4-methyl-1-heptenyl]-5-methyl-2-oxo-1,3-oxazolidin-3-yl}ethyl)sulfanyl]-1,3-thiazole-4-carboxylic acid (Compound 45-6)

TLC: Rf0.47 (methylene chloride:methanol=4:1);
NMR (CDCl$_3$): δ 1.15 (s, 3H) 1.30-1.44 (m, 3H) 1.49-1.83 (m, 4H) 2.12-2.46 (m, 2H) 3.41 (s, 3H) 3.43-3.75 (m, 6H) 3.84-3.98 (m, 1H) 4.06-4.38 (m, 1H) 5.30-5.51 (m, 1H) 5.84-6.21 (m, 1H) 8.08 (s, 1H).

Example 45(7)

2-[(2-{(4S,5S)-4-[(1E)-4-hydroxy-4-methyl-1-octenyl]-5-methyl-2-oxo-1,3-oxazolidin-3-yl}ethyl)sulfanyl]-1,3-thiazole-4-carboxylic acid (Compound 45-7)

TLC: Rf0.39 (ethyl acetate:methanol:acetic acid=15:1:1);
NMR (CDCl$_3$): δ 0.77-0.99 (m, 3H), 1.09-1.20 (m, 3H), 1.19-1.56 (m, 9H), 2.14-2.45 (m, 2H), 3.27-3.59 (m, 3H), 3.58-3.73 (m, 1H), 3.79-3.94 (m, 1H), 4.15-4.30 (m, 1H), 4.30-4.93 (m, 2H), 5.18-5.51 (m, 1H), 5.80-6.22 (m, 1H), 8.10 (s, 1H).

Example 45(8)

2-[(2-{(4S,5S)-4-[(1E)-4-hydroxy-4-methyl-1-decenyl]-5-methyl-2-oxo-1,3-oxazolidin-3-yl}ethyl)sulfanyl]-1,3-thiazole-4-carboxylic acid (Compound 45-8)

TLC: Rf0.61 (ethyl acetate:methanol:acetic acid=15:1:1);
NMR (CDCl$_3$): δ 0.71-1.03 (m, 3H), 1.07-1.59 (m, 16H), 2.10-2.48 (m, 2H), 2.99-3.79 (m, 6H), 3.77-3.95 (m, 1H), 4.13-4.31 (m, 1H), 5.20-5.48 (m, 1H), 5.86-6.17 (m, 1H), 8.06-8.13 (m, 1H).

Example 45(9)

2-[(2-{(4S,5S)-4-[(1E)-5-cyclohexyl-4-hydroxy-4-methyl-1-pentenyl]-5-methyl-2-oxo-1,3-oxazolidin-3-yl}ethyl)sulfanyl]-1,3-thiazole-4-carboxylic acid (Compound 45-9)

TLC: Rf0.56 (ethyl acetate:methanol:acetic acid=15:1:1);
NMR (CDCl$_3$): δ 0.81-1.86 (m, 19H) 2.15-2.76 (m, 4H) 3.28-3.73 (m, 4H) 3.79-3.93 (m, 1H) 4.15-4.28 (m, 1H) 5.36 (dd, J=15.28, 9.06 Hz, 1H) 5.89-6.08 (m, 1H) 8.10 (s, 1H).

Example 45(10)

2-[(2-{(4S,5S)-4-[(1E)-8-fluoro-4-hydroxy-4-methyl-1-octenyl]-5-methyl-2-oxo-1,3-oxazolidin-3-yl}ethyl)sulfanyl]-1,3-thiazole-4-carboxylic acid (Compound 45-10)

TLC: Rf0.44 (ethyl acetate:methanol:water=40:10:1);
NMR (CDCl$_3$): δ 1.18 (s, 3H) 1.38 (d, J=6.22 Hz, 3H) 1.41-1.78 (m, 6H) 2.19-2.37 (m, 2H) 3.31-3.74 (m, 4H) 3.82-3.91 (m, 1H) 4.17-4.27 (m, 1H) 4.33-4.42 (m, 1H) 4.48-4.59 (m, 1H) 5.38 (dd, J=16.56, 9.06 Hz, 1H) 5.90-6.09 (m, 1H) 8.04-8.17 (m, 1H).

Example 45(11)

2-[(2-{(4S,5S)-5-methyl-2-oxo-4-[(1E)-8,8,8-trifluoro-4-hydroxy-4-methyl-1-octenyl]-1,3-oxazolidin-3-yl}ethyl)sulfanyl]-1,3-thiazole-4-carboxylic acid (Compound 45-11)

TLC: Rf0.52 (ethyl acetate:methanol:water=40:10:1);
NMR (CDCl$_3$): δ 1.19 (s, 3H) 1.38 (d, J=6.22 Hz, 3H) 1.45-1.73 (m, 4H) 1.97-2.17 (m, 2H) 2.24-2.35 (m, 2H) 3.31-3.74 (m, 4H) 3.79-3.95 (m, 1H) 4.15-4.31 (m, 1H) 5.39 (dd, J=15.28, 8.87 Hz, 1H) 5.91-6.11 (m, 1H) 8.10 (s, 1H).

Example 45(12)

2-[(2-{(4S,5S)-4-[(1E)-4-hydroxy-4-methyl-1-pentenyl]-5-methyl-2-oxo-1,3-oxazolidin-3-yl}ethyl)sulfanyl]-1,3-thiazole-4-carboxylic acid (Compound 45-12)

TLC: Rf0.29 (ethyl acetate:methanol:acetic acid=10:1:1);
NMR (CDCl$_3$): δ 1.23 (s, 3H), 1.24 (s, 3H), 1.38 (d, J=6.40 Hz, 3H), 2.11-2.45 (m, 2H), 3.13-4.08 (m, 7H), 4.14-4.31 (m, 1H), 5.37 (dd, J=15.1, 8.97 Hz, 1H), 6.03 (dt, J=15.1, 7.46, 7.32 Hz, 1H), 8.10 (s, 1H).

Example 45(13)

2-[(2-{(4S,5S)-4-[(1E)-4-hydroxy-4-isopropyl-1-octenyl]-5-methyl-2-oxo-1,3-oxazolidin-3-yl}ethyl)sulfanyl]-1,3-thiazole-4-carboxylic acid (Compound 45-13)

TLC: Rf0.40 (ethyl acetate:methanol:acetic acid=15:1:1);
NMR (CDCl$_3$): δ 0.69-1.05 (m, 9H), 1.07-1.53 (m, 9H), 1.62-1.90 (m, 1H), 2.01-2.56 (m, 2H), 3.04-4.72 (m, 8H), 5.16-5.55 (m, 1H), 5.88-6.23 (m, 1H), 8.06-8.13 (m, 1H).

Example 45(14)

2-[(2-{(4S,5S)-4-[(1E)-10-fluoro-4-hydroxy-4-methyl-1-decenyl]-5-methyl-2-oxo-1,3-oxazolidin-3-yl}ethyl)sulfanyl]-1,3-thiazole-4-carboxylic acid (Compound 45-14)

TLC: Rf0.57 (ethyl acetate:methanol:water=40:10:1);
NMR (CDCl$_3$): δ 1.16 (s, 3H) 1.21-1.52 (m, 11H) 1.56-1.79 (m, 2H) 2.17-2.40 (m, 2H) 3.31-3.78 (m, 4H) 3.87 (t, J=8.23 Hz, 1H) 4.16-4.28 (m, 1H) 4.31-4.41 (m, 1H) 4.47-4.56 (m, 1H) 5.37 (dd, J=15.09, 9.06 Hz, 1H) 5.91-6.12 (m, 1H) 8.10 (s, 1H).

Example 45(15)

2-[(2-{(4S,5S)-4-[(1E,6E)-4-hydroxy-4-methyl-1,6-nonadienyl]-5-methyl-2-oxo-1,3-oxazolidin-3-yl}ethyl)sulfanyl]-1,3-thiazole-4-carboxylic acid (Compound 45-15)

TLC: Rf0.35 (methylene chloride:methanol:acetic acid=18:1:1);
NMR (CDCl$_3$): δ 0.99 and 1.00 (each t, J=7.41 Hz, totally 3H), 1.14 and 1.15 (each s, totally 3H), 1.38 (d, J=6.22 Hz, 3H), 1.97-2.38 (m, 6H), 3.31-3.73 (m, 4H), 3.82-3.91 (m, J=8.87, 7.78 Hz, 1H), 4.17-4.29 (m, 1H), 5.29-5.49 (m, 2H), 5.51-5.65 (m, 1H), 5.92-6.08 (m, 1H), 8.10 (s, 1H).

Example 45(16)

2-[(2-{(4S,5S)-4-[(1E)-4-hydroxy-4-methyl-6-phenyl-1-hexenyl]-5-methyl-2-oxo-1,3-oxazolidin-3-yl}ethyl)sulfanyl]-1,3-thiazole-4-carboxylic acid (Compound 45-16)

TLC: Rf0.48 (ethyl acetate:methanol:acetic acid=18:1:1);
NMR (CDCl$_3$): δ 1.17-1.27 (m, 3H) 1.36 (t, J=6.30 Hz, 3H) 1.63-1.86 (m, 2H) 2.15-2.81 (m, 4H) 3.21-4.37 (m, 8H) 5.38 (dd, J=15.30, 8.70 Hz, 1H) 5.96-6.15 (m, 1H) 7.00-7.40 (m, 5H) 7.98-8.13 (m, 1H).

Example 45(17)

2-[(2-{(4S,5S)-4-[(1E)-5-cyclobutyl-4-hydroxy-4-methyl-1-pentenyl]-5-methyl-2-oxo-1,3-oxazolidin-3-yl}ethyl)sulfanyl]-1,3-thiazole-4-carboxylic acid (Compound 45-17)

TLC: Rf0.57 (methylene chloride:methanol=4:1);
NMR (CDCl$_3$): δ 1.12 (s, 3H) 1.38 (d, J=6.22 Hz, 3H) 1.54-2.11 (m, 8H) 2.15-2.35 (m, 2H) 2.35-2.52 (m, 1H) 3.25-3.77 (m, 5H) 3.81-3.93 (m, 1H) 4.17-4.28 (m, 1H) 5.28-5.42 (m, 1H) 5.91-6.11 (m, 1H) 8.10 (s, 1H).

Example 45(18)

2-[(2-{(4S,5S)-4-[(1E)-5-cyclopropyl-4-hydroxy-4-methyl-1-pentenyl]-5-methyl-2-oxo-1,3-oxazolidin-3-yl}ethyl)sulfanyl]-1,3-thiazole-4-carboxylic acid (Compound 45-18)

TLC: Rf0.61 (methylene chloride:methanol=4:1);
NMR (CDCl$_3$): δ 0.03-0.14 (m, 2H) 0.44-0.58 (m, 2H) 0.63-0.78 (m, 1H) 1.23 (s, 3H) 1.31-1.50 (m, 5H) 2.20-2.49 (m, 2H) 3.26-3.98 (m, 6H) 4.17-4.29 (m, 1H) 5.37 (dd, J=17.93, 9.15 Hz, 1H) 5.93-6.13 (m, 1H) 8.10 (s, 1H).

Example 45(19)

2-[(2-{(4S,5S)-4-[(1E)-4-hydroxy-4-methyl-1-octen-5-in-1-yl]-5-methyl-2-oxo-1,3-oxazolidin-3-yl}ethyl)sulfanyl]-1,3-thiazole-4-carboxylic acid (Compound 45-19)

TLC: Rf0.47 (methylene chloride:methanol=5:1);
NMR (DMSO-d$_6$): δ 1.01 (t, J=7.50 Hz, 3H) 1.20-1.33 (m, 6H) 2.14 (m, 2H) 2.20-2.31 (m, 2H) 3.35-3.61 (m, 4H) 3.95 (m, 1H) 4.19 (m, 1H) 5.23 (m, 1H) 5.39 (dd, J=15.10, 9.00 Hz, 1H) 5.86 (dt, J=15.30, 7.20 Hz, 1H) 8.34 (s, 1H).

Example 45(20)

2-[(2-{(4S,5S)-4-[(1E)-5-cyclopentyl-4-hydroxy-4-methyl-1-pentenyl]-5-methyl-2-oxo-1,3-oxazolidin-3-yl}ethyl)sulfanyl]-1,3-thiazole-4-carboxylic acid (Compound 45-20)

TLC: Rf0.50 (ethyl acetate:methanol:acetic acid=18:1:1);
NMR (CDCl$_3$): δ 0.96-1.16 (m, 3H) 1.18 (s, 3H) 1.37 (d, J=6.22 Hz, 3H) 1.40-1.93 (m, 8H) 2.18-2.42 (m, 2H) 3.23-3.76 (m, 4H) 3.87 (t, J=9.15 Hz, 1H) 4.16-4.27 (m, 1H) 4.28-4.65 (m, 2H) 5.35 (ddd, J=15.28, 9.15, 1.56 Hz, 1H) 5.91-6.13 (m, 1H) 8.09-8.09 (m, 1H).

Example 45(21)

2-[(2-{(4S,5S)-4-[(1E,5E,7E)-4-hydroxy-4-methyl-1,5,7-nonatrienyl]-5-methyl-2-oxo-1,3-oxazolidin-3-yl}ethyl)sulfanyl]-1,3-thiazole-4-carboxylic acid (Compound 45-21)

TLC: Rf0.31 (methylene chloride:methanol:acetic acid=18:1:1);
NMR (CDCl$_3$): δ 1.29-1.39 (m, 6H), 1.76 (d, J=6.95 Hz, 3H), 2.30-2.42 (m, 2H), 3.26-3.70 (m, 4H), 3.75-3.86 (m, 1H), 4.14-4.27 (m, 1H), 5.33 (dd, J=14.91, 9.42 Hz, 1H), 5.49-6.23 (m, 5H), 8.09 and 8.10 (each s, totally 1H).

Example 45(22)

2-[(2-{(4S,5S)-4-[(1E)-4-hydroxy-1-nonenyl]-5-methyl-2-oxo-1,3-oxazolidin-3-yl}ethyl)sulfanyl]-1,3-thiazole-4-carboxylic acid (Compound 45-22)

TLC: Rf0.61 (ethyl acetate:methanol:acetic acid=15:1:1);
NMR (CDCl$_3$): δ 0.81-0.94 (m, 3H) 1.14-1.64 (m, 11H) 2.07-3.16 (m, 4H) 3.30-3.78 (m, 5H) 3.79-3.90 (m, 1H) 4.13-4.31 (m, 1H) 5.25-5.53 (m, 1H) 5.80-6.07 (m, 1H) 8.11 (s, 1H).

Example 45(23)

2-[(2-{(4S,5S)-4-[(1E)-6-cyclobutyl-4-hydroxy-4-methyl-1-hexenyl]-5-methyl-2-oxo-1,3-oxazolidin-3-yl}ethyl)sulfanyl]-1,3-thiazole-4-carboxylic acid (Compound 45-23)

TLC: Rf0.50 (ethyl acetate:methanol:water=40:10:1);
NMR (CDCl$_3$): δ 1.16 (s, 3H) 1.25-1.65 (m, 9H) 1.73-1.92 (m, 2H) 1.94-2.38 (m, 5H) 3.28-3.74 (m, 4H) 3.87 (t, J=8.23 Hz, 1H) 4.16-4.28 (m, 1H) 4.50-5.16 (m, 1H) 5.36 (dd, J=16.19, 9.06 Hz, 1H) 5.93-6.11 (m, 1H) 8.10 (s, 1H).

Example 45(24)

2-[(2-{(4S,5S)-4-[(1E)-5-cyclohexyl-4-hydroxy-1-pentenyl]-5-methyl-2-oxo-1,3-oxazolidin-3-yl}ethyl)sulfanyl]-1,3-thiazole-4-carboxylic acid (Compound 45-24)

TLC: Rf0.47 (ethyl acetate:methanol:acetic acid=15:1:1);
NMR (CDCl$_3$): δ 0.67-1.89 (m, 16H), 2.09-2.42 (m, 2H), 3.14-4.09 (m, 8H), 4.12-4.32 (m, 1H), 5.21-5.54 (m, 1H), 5.78-6.11 (m, 1H), 8.11 (s, 1H).

Example 46

2-[(2-{(4S,5S)-4-[3-(1-butylcyclobutyl)-3-hydroxypropyl]-5-methyl-2-oxo-1,3-oxazolidin-3-yl}ethyl)sulfanyl]-1,3-thiazole-4-carboxylic acid (Compound 46)

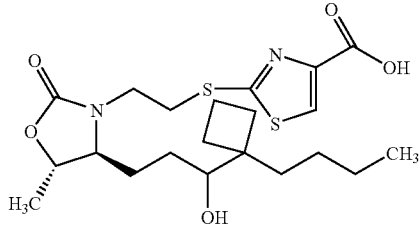

To a solution of ethyl ester of the compound 34-4 (175 mg) in ethanol (3 mL) was added p-toluenesulfonylhydrazide (6 g) and the solution was dissolved at 90° C. Sodium acetate (4.5 g) was added thereto and the solution was stirred for 10 hours. After standing to cool to room temperature, the reaction solution was concentrated. Ethyl acetate and water was added thereto and the solution was extracted with ethyl acetate. The organic layer was washed with 1N hydrochloric acid, an aqueous saturated sodium bicarbonate solution and brine, dried over anhydrous sodium sulfate and concentrated. The obtained residue was purified by column chromatography on silica gel (Fuji-silysia, FL60D, 60 mL, n-hexane:ethyl acetate=9.11). The title compound having the following physical data was obtained by the same procedure by the same procure as the reaction of example 8 using the obtained residue instead of the compound 7.

TLC: Rf0.22 (methylene chloride:methanol:acetic acid=18:1:1);
NMR (CDCl$_3$): δ 0.93 (m, 3H), 1.34 (m, 10H), 1.76 (m, 9H), 3.61 (m, 6H), 4.31 (m, 1H), 8.10 and 8.09 (each s, totally 1H).

Example 46(1)-46(6)

By the same procedure by the same procedure as the reaction of example 46 using the corresponding ester compound instead of ethyl ester of the compound 34-4, the following title compounds were obtained.

Example 46(1)

2-({2-[(4S,5S)-4-(3-hydroxy-4-phenoxybutyl)-5-methyl-2-oxo-1,3-oxazolidin-3-yl]ethyl}sulfanyl)-1,3-thiazole-4-carboxylic acid (Compound 46-1)

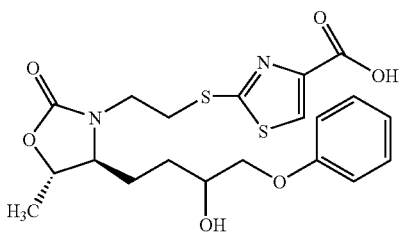

TLC: Rf0.26 (ethyl acetate:methanol:acetic acid=15:1:1);
NMR (CDCl$_3$): δ 1.39 (d, J=6.22 Hz, 3H) 1.83 (m, 4H) 3.49 (m, 6H) 3.90 (m, 4H) 4.32 (m, 1H) 6.89 (d, J=8.06 Hz, 2H) 6.98 (t, J=7.32 Hz, 1H) 7.30 (m, 2H) 8.08 (s, 1H).

Example 46(2)

2-({2-[(4S,5S)-4-(8-fluoro-3-hydroxy-4,4-dimethyloctyl)-5-methyl-2-oxo-1,3-oxazolidin-3-yl]ethyl}sulfanyl)-1,3-thiazole-4-carboxylic acid (Compound 46-2)

TLC: Rf0.37 (ethyl acetate:methanol:acetic acid=15:1:1);
NMR (CDCl$_3$): δ 0.89 (m, 6H) 1.62 (m, 13H) 3.57 (m, 6H) 4.34 (m, 2H) 4.53 (m, 1H) 5.59 (m, 1H) 8.10 (m, 1H).

Example 46(3)

2-({2-[(2S)-2-(3-hydroxy-4-phenoxybutyl)-5-oxo-1-pyrrolidinyl]ethyl}sulfanyl)-1,3-thiazole-4-carboxylic acid (Compound 46-3)

TLC: Rf0.23 (ethyl acetate:methanol:acetic acid=8:1:1);
NMR (CDCl$_3$): δ 1.65 (m, 4H) 2.27 (m, 4H) 3.69 (m, 8H) 6.18 (m, 2H) 6.89 (m, 2H) 6.96 (m, 1H) 7.28 (m, 2H) 8.06 (s, 1H).

Example 46(4)

2-[(2-{(2S)-2-[4-(3-fluorophenoxy)-3-hydroxybutyl]-5-oxo-1-pyrrolidinyl}ethyl)sulfanyl]-1,3-thiazole-4-carboxylic acid (Compound 46-4)

TLC: Rf0.48 (ethyl acetate:methanol:acetic acid=5:1:1);
NMR (CDCl$_3$): δ 1.20-2.64 (m, 8H), 2.99-5.21 (m, 10H), 6.43-6.78 (m, 3H), 7.08-7.36 (m, 1H), 8.07 (s, 1H).

Example 46(5)

2-[(2-{(2S)-2-[3-hydroxy-4-(4-methylphenoxy)butyl]-5-oxo-1-pyrrolidinyl}ethyl)sulfanyl]-1,3-thiazole-4-carboxyl acid (Compound 46-5)

TLC: Rf0.20 (ethyl acetate:methanol:acetic acid=8:1:1);
NMR (CDCl$_3$): δ 1.45-2.56 (m, 11H) 3.20-4.22 (m, 10H) 6.79 (d, J=8.60 Hz, 2H) 7.08 (d, J=8.60 Hz, 2H) 8.06 (s, 1H).

Example 46(6)

2-({2-[(4S)-4-(4-hydroxy-4-methyloctyl)-2-oxo-1,3-oxazolidin-3-yl]ethyl}sulfanyl)-1,3-thiazole-4-carboxylic acid (Compound 46-6)

TLC: Rf0.43 (ethyl acetate:methanol:acetic acid 15:1:1);
NMR (CDCl$_3$): δ 0.79-1.01 (m, 3H) 1.04-2.29 (m, 15H) 3.13-4.05 (m, 8H) 4.31-4.50 (m, 1H) 8.08 (s, 1H).

Example 47

(2E)-7-{(1R,2R)-2-[(1E,3R)-3-hydroxy-4,4-dimethyl-1-octenyl]-5-oxocyclopentyl}-2-heptenoic acid (Compound 47)

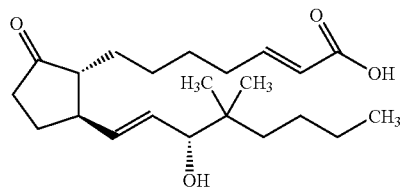

By the same procedure as a series of reactions of Example 6→Example 21→Example 22→Example 23→Example 24 using the compound 19 instead of the compound 5, the title compound having the following physical data was obtained.

TLC: Rf0.41 (n-hexane:ethyl acetate=1:2);
NMR (CDCl$_3$): δ 0.85 (s, 3H) 0.91 (s, 3H) 0.92 (m, 3H) 1.41 (m, 14H) 1.85 (m, 1H) 2.14 (m, 3H) 2.44 (m, 2H) 3.83 (d, J=6.04 Hz, 1H) 5.63 (m, 2H) 5.81 (d, J=15.74 Hz, 1H) 7.04 (m, 1H).

Example 48

7-{(1R,2R)-2-[(1E,3S,5S)-3-hydroxy-5-methyl-1-nonenyl]-5-oxocyclopentyl}heptanoic acid (Compound 48)

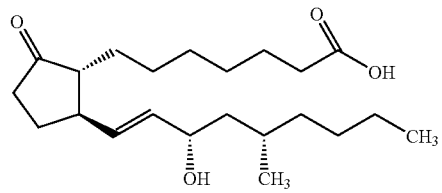

By the same procedure as a series of reactions of Example 19→Example 20→Example 21→Example 8→the Reaction B of Example 23→Example 24 using the compound 17 instead of the compound 18, the title compound having the following physical data was obtained.

TLC: Rf0.46 (n-hexane:ethyl acetate=1:2);

NMR (CDCl$_3$): δ 0.89 (m, J=5.95, 5.95 Hz, 6H) 1.42 (m, 19H) 1.85 (m, J=6.41 Hz, 1H) 2.11 (m, 3H) 2.36 (m, 4H) 4.21 (m, 1H) 5.59 (m, 2H).

Example 49

Ethyl 2-({2-[(1R,2S,5S)-2-(acetyloxy)-5-formylcyclopentyl]ethyl}thio)-1,3-thiazole-4-carboxylate (Compound 49)

By the same procedure as the reaction of Example 19 using the compound 17 instead of the compound 18, the title compound having the following physical data was obtained.

TLC: Rf0.27 (hexane:ethyl acetate=2:1);

NMR (CDCl$_3$): δ 1.32-1.49 (m, 3H) 1.78-2.15 (m, 9H) 2.35-2.51 (m, 1H) 2.69-2.84 (m, 1H) 3.10-3.31 (m, 2H) 4.32-4.48 (m, 2H) 5.29-5.37 (m, 1H) 8.02 (s, 1H) 9.67 (d, J=2.74 Hz, 1H).

Example 50

2-[(2-{(1R,2R,5S)-2-[(1E)-5-cyclohexyl-4-hydroxy-4-methyl-1-pentenyl]-5-hydroxycyclopentyl}ethyl)thio]-1,3-thiazole-4-carboxylic acid (Compound 50)

By the same procedure as a series of reactions of Example 43→Example 44→Example 45 using 5-({4-cyclohexyl-3-methyl-3-[(trimethylsilyl)oxy]butyl}sulfonyl)-1-phenyl-1H-tetrazole instead of the compound 41 and using the compound 49 instead of the compound 42, the title compound having the following physical data was obtained.

TLC: Rf0.39 (ethyl acetate:methanol:acetic acid=15:1:1).

NMR (CDCl$_3$): δ 0.84-2.25 (m, 25H) 2.33-2.53 (m, 1H) 2.77-3.92 (m, 5H) 4.48-4.57 (m, 1H) 5.28-5.40 (m, 1H) 5.42-5.57 (m, 1H) 8.08 (s, 1H).

Example 51

Ethyl 2-[(2-{(1R,2R,5S)-2-[(1E)-5-cyclohexyl-4-hydroxy-4-methyl-1-pentenyl]-5-hydroxycyclopentyl}ethyl)thio]-1,3-thiazole-4-carboxylate (Compound 51)

To a solution of the compound 50 in N,N-dimethylformamide (10 mL) were added potassium carbonate (1.20 g) and ethane iodide (0.350 mL) at 0° C. and the solution was stirred at room temperature for 3 hours. To the reaction solution was added an aqueous saturated sodium chloride solution and the solution was extracted with ethyl acetate. The organic layer was washed with water and brine, dried over anhydrous sodium sulfate and concentrated. The obtained residue was purified by column chromatography on silica gel (n-hexane:ethyl acetate=4:1) to give the title compound (1.03 g) having the following physical data.

TLC: Rf0.21 (hexane:ethyl acetate=2:1);

NMR (CDCl$_3$): δ 0.83-2.13 (m, 26H) 2.16 (d, J=6.95 Hz, 2H) 2.26-2.49 (m, 1H) 2.81-2.98 (m, 1H) 3.50-3.69 (m, 1H) 4.39 (q, J=7.14 Hz, 2H) 4.43-4.49 (m, 1H) 5.24-5.53 (m, 2H) 7.97 (s, 1H).

Example 52

Ethyl 2-[(2-{(1R,2R)-2-[(1E)-5-cyclohexyl-4-hydroxy-4-methyl-1-pentenyl]-5-oxocyclopentyl}ethyl)thio]-1,3-thiazole-4-carboxylate (Compound 52)

To a solution of the compound 51 (242 mg) in dimethylsulfoxide (2.0 mL)/ethyl acetate (4.0 mL) were added diisopropylethylamine (0.70 mL) and sulfur trioxide-pyridine complex (320 mg) at 10° C. and the solution was stirred for 30 minutes. Water was added to the reaction solution, which was extracted with ethyl acetate. The organic layer was washed 1N hydrochloric acid, water and brine, anhydrous sodium sulfate and concentrated. The obtained residue was purified by column chromatography on silica gel (n-hexane:ethyl acetate=7:3) to give the title compound (154 mg) having the following physical data.

TLC: Rf0.24 (hexane:ethyl acetate=2:1);

NMR (CDCl$_3$): δ 0.83-2.27 (m, 27H) 2.31-2.58 (m, 2H) 3.42 (t, J=7.23 Hz, 2H) 4.39 (q, J=7.14 Hz, 2H) 5.41-5.55 (m, 1H) 5.61-5.75 (m, 1H) 8.01 (s, 1H).

Example 53

2-[(2-{(1R,2R)-2-[(1E)-5-cyclohexyl-4-hydroxy-4-methyl-1-pentenyl]-5-oxocyclopentyl}ethyl)sulfanyl]-1,3-thiazole-4-carboxylic acid (Compound 53)

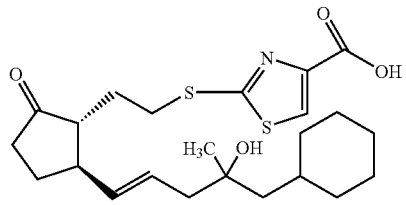

By the same procedure as the reaction of Example 30 using the compound 52 instead of the compound 29, the title compound (109 mg) having the following physical data was obtained.

TLC: Rf0.29 (ethyl acetate:acetic acid=100:1);

NMR (CDCl$_3$): δ 0.82-2.61 (m, 26H) 3.36 (t, J=7.41 Hz, 2H) 3.40-3.68 (m, 2H) 5.51 (dd, J=15.00, 9.00 Hz, 1H) 5.60-5.78 (m, 1H) 8.10 (s, 1H).

Example 54

Ethyl 2-[(2-{(1R,2S,5R)-2-(acetyloxy)-5-[(1E)-4-hydroxy-4-methyl-1-nonenyl]cyclopentyl}ethyl)thio]-1,3-thiazole-4-carboxylate (Compound 54)

To a solution of (3-hydroxy-3-methyloctyl)(triphenyl)phosphonium iodide (800 mg) in anhydrous tetrahydrofuran (9.00 mL) was added n-butyllithium (1.60M in hexane, 1.90 mL) at room temperature and the solution was stirred for 1 hour. To the solution was added a solution of the compound 49 (349 mg) in anhydrous tetrahydrofuran (6.00 mL) was slowly added at −78° C. and the solution was stirred for 2 hours. The solution temperature was risen to room temperature. The reaction solution was poured into ice water and extracted with ethyl acetate. The organic layer was washed water and brine, dried over anhydrous sodium sulfate and concentrated. The obtained residue was purified by column chromatography on silica gel (n-hexane:ethyl acetate=4:1) to give the title compound (178 mg) having the following physical data.

TLC: Rf0.61 (hexane:ethyl acetate=1:1);
NMR (CDCl$_3$): δ 0.83-0.93 (m, 3H) 1.11 (s, 3H) 1.18-2.22 (m, 23H) 2.31-2.53 (m, 1H) 3.16-3.38 (m, 2H) 4.40 (q, J=7.01 Hz, 2H) 5.20-5.40 (m, 2H) 5.43-5.60 (m, 1H) 7.97-8.07 (m, 1H).

Example 55

2-[(2-{(1R,2S,5R)-2-hydroxy-5-[(1E)-4-methyl-4-(tetrahydro-2H-pyran-2-yloxy)-1-nonenyl]cyclopentyl}ethyl)thio]-1,3-thiazole-4-carboxylic acid (Compound 55)

By the same procedure as a series of reactions of the Reaction B of Example 21→Example 8 using the compound 54 instead of the compound prepared by the Reaction A of Example 21, the title compound having the following physical data was obtained.

TLC: Rf0.63 (ethyl acetate:methanol:acetic acid=15:1:1).
NMR (CDCl$_3$): δ 0.82-0.95 (m, 3H) 1.15 (s, 3H) 1.18-3.01 (m, 26H) 3.34-3.68 (m, 3H) 3.88-4.03 (m, 1H) 4.48-4.57 (m, 1H) 4.71-4.79 (m, 1H) 5.16-5.57 (m, 2H) 8.04-8.10 (m, 1H).

Example 56

Methyl 2-[(2-{(1R,2S,5R)-2-hydroxy-5-[(1E)-4-methyl-4-(tetrahydro-2H-pyran-2-yloxy)-1-nonenyl]cyclopentyl}ethyl)thio]-1,3-thiazole-4-carboxylate (Compound 56)

By the same procedure as the reaction of Example 51 using the compound 55 instead of the compound 50 and using methane iodide instead of ethane iodide, the title compound having the following physical data was obtained.

TLC: Rf0.32 (hexane:ethyl acetate=2:1);
NMR (CDCl$_3$): δ 0.88 (t, J=7.04 Hz, 3H) 1.15 (s, 3H) 1.18-2.43 (m, 24H) 2.80-2.98 (m, 1H) 3.17 (s, 1H) 3.39-3.49 (m, 1H) 3.50-3.69 (m, 1H) 3.88-3.99 (m, 4H) 4.38-4.54 (m, 1H) 4.67-4.81 (m, 1H) 5.15-5.31 (m, 1H) 5.33-5.50 (m, 1H) 7.98 (s, 1H).

Example 57

2-[(2-{(1R,2R)-2-[(1E)-4-hydroxy-4-methyl-1-nonenyl]-5-oxocyclopentyl}ethyl)sulfanyl]-1,3-thiazole-4-carboxylic acid (Compound 57)

By the same procedure as a series of reactions of the Reaction B of Example 29→Example 30 using the compound 56 (61.8 mg) instead of the compound prepared by the Reaction A of Example 29, the title compound (50.8 mg) having the following physical data was obtained.

TLC: Rf0.67 (ethyl acetate:methanol:acetic acid=15:1:1);
NMR (CDCl$_3$): δ 0.88 (t, J=6.68 Hz, 3H) 1.02-2.59 (m, 21H) 2.70-3.75 (m, 4H) 5.51 (dd, J=15.00, 9.00 Hz, 1H) 5.59-5.77 (m, 1H) 8.10 (s, 1H).

Example 58

Methyl (5Z)-7-{(1R,2R,3R,5R)-5-chloro-2-[(1E,5S)-5-methyl-3-oxo-1-nonenyl]-3-(tetrahydro-2H-pyran-2-yloxy)cyclopentyl}-5-heptenoate (Compound 58)

By the same procedure as the reaction of Example 6 using methyl (5Z)-7-[(1R,2R,3R,5R)-5-chloro-2-formyl-3-(tetrahydro-2H-pyran-2-yloxy)cyclopentyl]-5-heptenoate (Reg. No. 261772-21-8) instead of the compound 5 and using dimethyl [(4S)-4-methyl-2-oxooctyl]phosphonate instead of dimethyl (3,3-dimethyl-2-oxoheptyl)phosphonate, the title compound (360 mg) having the following physical data was obtained.

TLC: Rf0.67 (ethyl acetate:n-hexane=1:2).

Example 59

Methyl (5Z)-7-{(1R,2R,3R,5R)-5-chloro-2-[(1E,3S,5S)-3-hydroxy-5-methyl-1-nonenyl]-3-(tetrahydro-2H-pyran-2-yloxy)cyclopentyl}-5-heptenoate (Compound 59)

By the same procedure as the Reaction A of Example 21 using the compound 58 instead of the compound 20, the title compound having the following physical data was obtained.

TLC: Rf0.38 (ethyl acetate:n-hexane=1:2).

Example 60

Methyl (5Z)-7-{(1R,2R,3R,5R)-5-chloro-3-hydroxy-2-[(1E,3S,5S)-3-hydroxy-5-methyl-1-nonenyl]cyclopentyl}-5-heptenoate (Compound 60)

A solution of the compound 59 (223 mg) and p-toluenesulfonic acid 1-hydrate (24 mg) in methanol (3 mL) was stirred at room temperature for 30 minutes. The reaction solution was diluted with ethyl acetate, washed with water and brine, dried over anhydrous sodium sulfate and concentrated. The obtained residue was purified by column chromatography on silica gel (ethyl acetate:n-hexane=1:4→1:2→1:1→2:1) to the title compound (173 mg) having the following physical data.

TLC: Rf0.57 (ethyl acetate).

Example 61

(5Z)-7-{(1R,2R,3R,5R)-5-chloro-3-hydroxy-2-[(1E,3S,5S)-3-hydroxy-5-methyl-1-nonen-1-yl]cyclopentyl}-5-heptenoic acid (Compound 61)

By the same procedure as the reaction of Example 8 using the compound 60 instead of the compound 7, the title compound (78.6 mg) having the following physical data was obtained.

TLC: Rf0.47 (methanol:ethyl acetate=1:10);

NMR (CDCl₃): δ 0.89 (m, 6H) 1.42 (m, 11H) 2.16 (m, 10H) 4.13 (m, 3H) 5.52 (m, 4H).

Example 62

Methyl 2-{[2-((4S)-4-{(1E,3R)-3-[1-(4-fluorobutyl)cyclobutyl]-3-hydroxy-1-propenyl}-2-oxo-1,3-oxazolidin-3-yl)ethyl]sulfanyl}-1,3-thiazole-4-carboxylate (Compound 62)

To a solution of methyl 2-{[2-((4S)-4-{(1E,3R)-3-[1-(4-fluorobutyl)cyclobutyl]-3-hydroxy-1-propenyl}-2-oxo-1,3-oxazolidin-3-yl)ethyl]sulfanyl}-1,3-thiazole-4-carboxylate (methyl ester of compound 8-1) (78.0 mg) in methanol (1.0 mL) were added sodium tungstate (VI) dihydrate (14.0 mg) and 30% hydrogen peroxide solution (0.19 mL) at 0° C. and the solution was stirred for 1 hour and then for 3 hours at room temperature. Water was added to the reaction solution, which was extracted with ethyl acetate. The organic layer was washed with water and brine, dried over anhydrous sodium sulfate and concentrated. The obtained residue was purified by column chromatography on silica gel (n-hexane:ethyl acetate=2:3) to give the title compound (70.4 mg) having the following physical data.

TLC: Rf0.32 (hexane:ethyl acetate=1:4);

NMR (CDCl₃): δ 1.32-2.08 (m, 12H) 3.62-3.92 (m, 4H) 3.95-4.05 (t, 4H) 4.15-4.27 (m, 1H) 4.39 (m, 1H) 4.45-4.63 (m, 3H) 5.64-5.78 (m, 1H) 6.03 (dd, J=15.37, 5.49 Hz, 1H) 8.50 (s, 1H).

Example 63

2-{[2-((4S)-4-{(1E,3R)-3-[1-(4-fluorobutyl)cyclobutyl]-3-hydroxy-1-propenyl}-2-oxo-1,3-oxazolidin-3-yl)ethyl]sulfonyl}-1,3-thiazole-4-carboxylic acid (Compound 63)

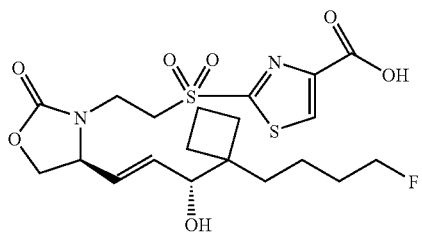

By the same procedure as the reaction of Example 8 using the compound 62 instead of the compound 7, the title compound having the following physical data was obtained.

TLC: Rf0.31 (ethyl acetate:methanol:acetic acid=15:1:1);

NMR (CDCl₃): δ 1.31-2.07 (m, 12H) 3.41 (s, 2H) 3.60-4.11 (m, 5H) 4.22 (d, J=5.31 Hz, 1H) 4.32-4.62 (m, 4H) 5.72 (dd, J=14.91, 8.69 Hz, 1H) 6.03 (dd, J=14.91, 5.31 Hz, 1H) 8.59 (s, 1H).

Example 63(1)

2-[(2-{(1R,2R)-2-[(1E)-5-cyclohexyl-4-hydroxy-4-methyl-1-pentenyl]-5-oxocyclopentyl}ethyl)sulfonyl]-1,3-thiazole-4-carboxylic acid (Compound 63-1)

By the same procedure as a series of reactions of Example 62→Example 8 using the compound 52 instead of methyl 2-{[2-((4S)-4-{(1E,3R)-3-[1-(4-fluorobutyl)cyclobutyl]-3-hydroxy-1-propenyl}-2-oxo-1,3-oxazolidin-3-yl)ethyl]sulfanyl}-1,3-thiazole-4-carboxylate (methyl ester of compound 8-1), the title compound having the following physical data was obtained.

TLC: Rf0.38 (ethyl acetate:methanol:acetic acid=15:1:1);

NMR (CDCl₃): δ 0.86-1.88 (m, 18H) 1.94-2.52 (m, 8H) 3.25 (s, 2H) 3.52-3.91 (m, 2H) 5.54 (dd, J=15.64, 8.87 Hz, 1H) 5.66-5.82 (m, 1H) 8.59 (s, 1H).

Example 64

Less polar: (9S,13R)-13-methyl-13-(4,4,4-trifluorobutyl)-7,14-dioxa-2,18-dithia-5,19-diazatricyclo[14.2.1.0⁵,⁹]nonadeca-1(19),10,16-triene-6,15-dione (compound 64-1)

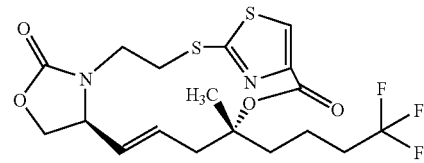

More polar: (9S,13S)-13-methyl-13-(4,4,4-trifluorobutyl)-7,14-dioxa-2,18-dithia-5,19-diazatricyclo[14.2.1.0⁵,⁹]nonadeca-1(19),10,16-triene-6,15-dione (Compound 62)

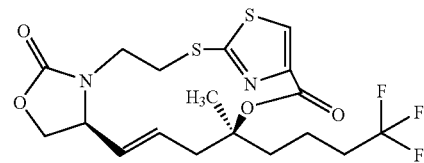

To a solution of the compound 45-4 (208 mg) in anhydrous tetrahydrofuran (5.0 mL) were added triethylamine (0.08 mL), 2,4,6-trichlorobenzoylchloride (0.08 mL) at 0° C. The solution was stirred for 1 hour and then 30 minutes at room temperature. Anhydrous toluene (45.0 mL) was added to the reaction solution, which was filtrated. The obtain filtrate was added to a solution of 4-(dimethylamine)pyridine (272 mg) in anhydrous toluene (45.0 ml) with heating to reflux and the solution was allowed to return to room temperature. 1N hydrochloric acid was added to the reaction solution, which was extracted with ethyl acetate. The organic layer was washed with water and brine, dried over anhydrous sodium sulfate and concentrated. The obtained residue was purified by column chromatography on silica gel (Fuji-silysia, FL60D, 75 cc, hexane:ethyl acetate=4:1) to give the title compound (less polar: 83.9 mg, more polar: 75.0 mg) having the following physical data.

Less Polar:
TLC: Rf0.57 (hexane:ethyl acetate=1:1);
NMR (CDCl₃): δ 1.51-1.72 (m, 2H) 1.74 (s, 3H) 1.80-2.28 (m, 3H) 2.32-2.62 (m, 3 H) 3.23-3.49 (m, 2H) 3.58-3.83 (m, 2H) 3.84-3.98 (m, 1H) 4.29-4.52 (m, 2H) 5.57 (dd, J=15.09, 8.51 Hz, 1H) 5.80-5.99 (m, 1H) 7.97 (s, 1H).

More Polar:
TLC: Rf0.49 (hexane:ethyl acetate=1:1);
NMR (CDCl₃): δ 1.45-1.85 (m, 5H) 1.90-2.23 (m, 4H) 2.31-2.51 (m, 1H) 2.73 (dd, J=13.81, 11.44 Hz, 1H) 3.26-3.47 (m, 2H) 3.61-3.79 (m, 2H) 3.85-3.98 (m, 1H) 4.27-4.49 (m, 2H) 5.55 (dd, J=14.18, 8.14 Hz, 1H) 5.89-6.05 (m, 1H) 7.95 (s, 1H).

Example 65(1)

2-[(2-{(4S)-2-oxo-4-[(1E,4R)-8,8,8-trifluoro-4-hydroxy-4-methyl-1-octenyl]-1,3-oxazolidin-3-yl}ethyl)sulfanyl]-1,3-thiazole-4-carboxylic acid (Compound 65-1)

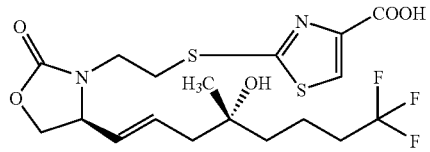

By the same procedure as the reaction of Example 8 using the compound 64-1 (Less polar) instead of the compound 7 and using a mixture of tetrahydrofuran and methanol instead of methanol, the title compound having the following physical data was obtained.
TLC: Rf0.44 (ethyl acetate:methanol:acetic acid=15:1:1);
NMR (CDCl₃): δ 1.19 (s, 3H) 1.42-1.77 (m, 4H) 1.96-2.22 (m, 2H) 2.29 (d, J=7.32 Hz, 2H) 3.31-3.81 (m, 6H) 3.91-4.03 (m, 1H) 4.32-4.52 (m, 2H) 5.43 (dd, J=15.73, 8.05 Hz, 1H) 5.91-6.08 (m, 1H) 8.11 (s, 1H).

Example 65(2)

2-[(2-{(4S)-2-oxo-4-[(1E,4S)-8,8,8-trifluoro-4-hydroxy-4-methyl-1-octenyl]-1,3-oxazolidin-3-yl}ethyl)sulfanyl]-1,3-thiazole-4-carboxylic acid (Compound 65-2)

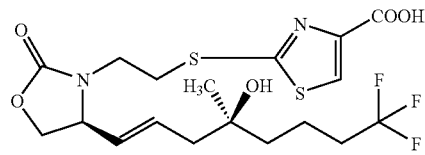

By the same procedure as the reaction of Example 8 using the compound 64-2 (More polar) instead of the compound 7 and using a mixture of tetrahydrofuran and methanol instead of methanol, the title compound having the following physical data was obtained.
TLC: Rf0.46 (ethyl acetate:methanol:acetic acid=15:1:1);
NMR (CDCl₃): δ 1.19 (s, 3H) 1.43-1.76 (m, 4H) 1.94-2.13 (m, 2H) 2.17-2.42 (m, 2H) 3.32-3.81 (m, 6H) 3.90-4.04 (m, 1H) 4.28-4.53 (m, 2H) 5.43 (dd, J=15.19, 8.60 Hz, 1H) 5.92-6.10 (m, 1H) 8.11 (s, 1H).

Example 66

Methyl [(2R)-2-({[tert-butyl(dimethyl)silyl]oxy}methyl)-5-oxo-1-pyrrolidinyl]acetate (Compound 66)

To a solution of (5R)-5-({[tert-butyl(dimethyl)silyl]oxy}methyl)-2-pyrrolidinone (11.2 g) in tetrahydrofuran (97 mL) were potassium tert-butoxide (6.27 g) and methyl bromoacetate (8.11 g) at 0° C. and the solution was stirred for 2 hours. To the reaction solution were added water, ethyl acetate and hexane and the reaction solution was separated. The aqueous layer was extracted with ethyl acetate. The combined organic layer was washed with water and brine, dried over anhydrous sodium sulfate and concentrated to give the title compound (14.3 g) having the following physical data.
TLC: Rf0.38 (n-hexane:ethyl acetate=3:2);
NMR (CDCl₃): δ 0.04 (s, 6H) 0.87 (s, 9H) 1.64-1.79 (m, 1H) 2.07-2.25 (m, 1H) 2.32-2.54 (m, 2H) 3.54-3.77 (m, 2H) 3.72 (s, 3H) 3.78-3.90 (m, 1H) 3.95 (d, J=17.66 Hz, 1H) 4.46 (d, J=17.66 Hz, 1H).

Example 67

2-[(2R)-2-({[tert-butyl(dimethyl)silyl]oxy}methyl)-5-oxo-1-pyrrolidinyl]acetamide (Compound 67)

To a solution of the compound 66 (13.7 g) in methanol (91 mL) was added 28% ammonia (91 mL) at room temperature and the solution was stirred overnight. The reaction solution was concentrated. Brine and ethyl acetate were added thereto and the solution was separated. The aqueous layer was extracted with ethyl acetate. The combined organic layer was dried over anhydrous sodium sulfate and concentrated. The obtained residue was purified by column chromatography on silica gel (ethyl acetate-methanol=1:0→97:3→95:5→90:10) to give the title compound (10.1 g) having the following physical data.
TLC: Rf0.32 (ethyl acetate:methanol=9:1);
NMR (CDCl₃): δ 0.06 (s, 3H) 0.08 (s, 3H) 0.88 (s, 9H) 1.89-2.02 (m, 1H) 2.11-2.26 (m, 1H) 2.30-2.44 (m, 1H) 2.46-2.62 (m, 1H) 3.62 (dd, J=10.98, 3.11 Hz, 1H) 3.69-3.77 (m, 1H) 3.83 (dd, J=10.98, 2.74 Hz, 1H) 3.85 (d, J=16.37 Hz, 1H) 4.06 (d, J=16.37 Hz, 1H) 5.35 (s, 1H) 6.55 (s, 1H).

Example 68

2-[(2R)-2-({[tert-butyl(dimethyl)silyl]oxy}methyl)-5-oxo-1-pyrrolidinyl]ethanethioamide (Compound 68)

To a solution of the compound 67 (9.50 g) in methylene chloride (133 mL) was added Lawesson's reagent (6.71 g) at 0° C. and the solution was stirred for 3 hours. To the reaction solution was added an aqueous saturated sodium bicarbonate solution and ethyl acetate and then the solution was separated. The aqueous layer was extracted with ethyl acetate. The combined organic layer was washed with an aqueous saturated sodium bicarbonate solution and brine, dried over anhydrous sodium sulfate and concentrated. The obtained residue was purified by column chromatography on silica gel (n-hexane:ethyl acetate:methanol=60:40:0→33:67:0→0:90:10) to give the title compound (5.30 g) having the following physical data.
TLC: Rf0.51 (n-hexane:ethyl acetate=1:3);
NMR (CDCl₃): δ 0.07 (s, 3H) 0.08 (s, 3H) 0.88 (s, 9H) 1.92-2.06 (m, 1H) 2.11-2.28 (m, 1H) 2.36 (ddd, J=17.06, 10.20, 4.30 Hz, 1H) 2.56 (ddd, J=7.06, 9.83, 8.14 Hz, 1H) 3.62 (dd, J=11.07, 2.38 Hz, 1H) 3.70-3.78 (m, 1H) 3.87 (dd, J=11.07, 2.74 Hz, 1H) 4.17 (d, J=16.17 Hz, 1H) 4.51 (d, J=16.17 Hz, 1H) 7.48 (s, 1H) 8.36 (s, 1H).

Example 69

Ethyl 2-{[(2R)-2-({[tert-butyl(dimethyl)silyl]oxy}methyl)-5-oxo-1-pyrrolidinyl]methyl}-1,3-thiazole-4-carboxylate (Compound 69)

To a solution of the compound 68 (4.50 g) in dimethylformamide (15.0 mL) was ethyl bromopyruvate (2.33 mL) at 0° C. and the solution was stirred at room temperature for 2 hours. To the reaction solution were added imidazole (4.08 g) and tert-butyldimethylsilyl chloride (4.52 g) at 0° C. and the solution was stirred at room temperature for 2 hours. To the reaction solution were added ethyl acetate and water and then the solution was separated. The aqueous layer was extracted with ethyl acetate. The combined organic layer was washed with an aqueous saturated sodium bicarbonate solution, dried over anhydrous sodium sulfate and concentrated. The obtained residue was purified by column chromatography on silica gel (n-hexane:ethyl acetate=3.2→2:3) to give the title compound (4.75 g) having the following physical data.

TLC: Rf0.59 (n-hexane:ethyl acetate=1:3);

NMR (CDCl$_3$): δ −0.03 (s, 3H) −0.00 (s, 3H) 0.83 (s, 9H) 1.40 (t, J=7.14 Hz, 3H) 1.88-2.02 (m, 1H) 2.07-2.22 (m, 1H) 2.30-2.44 (m, 1H) 2.47-2.63 (m, 1H) 3.57 (dd, J=10.79, 3.11 Hz, 1H) 3.68-3.77 (m, 1H) 3.80 (dd, J=10.79, 3.29 Hz, 1H) 4.42 (q, J=7.14 Hz, 2H) 4.66 (d, J=15.92 Hz, 1H) 5.04 (d, J=15.92 Hz, 1H) 8.13 (s, 1H).

Example 70

(5R)-5-({[tert-butyl(dimethyl)silyl]oxy}methyl)-1-{[4-(hydroxymethyl)-1,3-thiazol-2-yl]methyl}-2-pyrrolidine (Compound 70)

To a solution of the compound 69 (1.00 g) in methanol (10.0 mL) was added sodium borohydride (589 mg) at room temperature and the solution was stirred at room temperature for 5 hours. The reaction solution was poured into an aqueous saturated ammonium chloride solution on ice and extracted with ethyl acetate. The organic layer was washed with brine, dried over anhydrous sodium sulfate and concentrated to give the title compound (940 mg) having the following physical data.

TLC: Rf0.30 (n-hexane:ethyl acetate=1:3);

NMR (CDCl$_3$): δ 0.01 (s, 3H) 0.03 (s, 3H) 0.86 (s, 9H) 1.86-2.00 (m, 1H) 2.05-2.20 (m, 1H) 2.30-2.44 (m, 1H) 2.46-2.62 (m, 1H) 3.61 (dd, J=10.43, 3.48 Hz, 1H) 3.70-3.84 (m, 2H) 4.50 (d, J=15.83 Hz, 1H) 4.74 (s, 2H) 5.11 (d, J=15.83 Hz, 1H) 7.13 (s, 1H).

Example 71

2-{[(2R)-2-({[tert-butyl(dimethyl)silyl]oxy}methyl)-5-oxo-1-pyrrolidintyl]methyl}-1,3-thiazole-4-carboaldehyde (Compound 71)

The compound 70 (940 mg) was dissolved in ethyl acetate (5.0 mL) and dimethylsulfoxide (5.0 mL) and triethylamine (1.53 mL) was added thereto. To the mixed solution was added a solution of sulfur trioxide-pyridine complex (1.59 g) in dimethylsulfoxide (5.0 mL) at room temperature and the solution was stirred for 35 minutes. To the solution was added ice water. Ethyl acetate was added thereto and the solution separated. The aqueous layer was extracted with ethyl acetate. The combined organic layer was washed with an aqueous saturated potassium bisulfate, water and brine, dried over anhydrous sodium sulfate and concentrated to give the title compound (880 mg) having the following physical data.

TLC: Rf0.64 (n-hexane:ethyl acetate=1:3);

NMR (CDCl$_3$): δ −0.01 (s, 3H) 0.01 (s, 3H) 0.84 (s, 9H) 1.85-2.00 (m, 1H) 2.06-2.21 (m, 1H) 2.30-2.45 (m, 1H) 2.46-2.63 (m, 1H) 3.61 (dd, J=10.43, 3.48 Hz, 1H) 3.72-3.86 (m, 2H) 4.67 (d, J=15.92 Hz, 1H) 5.06 (d, J=15.92 Hz, 1H) 8.14 (s, 1H) 9.99 (s, 1

Example 72

(2E)-3-(2-{[(2R)-2-({[tert-butyl(dimethyl)silyl]oxy}methyl)-5-oxo-1-pyrrolidinyl]methyl}-1,3-thiazole-4-yl)acrylic acid (Compound 72)

To a solution of the compound 71 (880 mg) in pyridine (12.5 mL) were added malonic acid (468 mg) and piperidine (148 mL) at room temperature and the solution was stirred at 110° C. for 15 minutes. The reaction solution was concentrated. Ethyl acetate and 0.3 M hydrochloric acid were added thereto and the solution separated. The aqueous solution was extracted with ethyl acetate. The combined organic layer was washed with 0.3 M hydrochloric acid and brine, dried over anhydrous sodium sulfate and concentrated to give the title compound (990 mg) having the following physical data.

TLC: Rf0.20 (n-hexane:ethyl acetate=1:2);

NMR (CDCl$_3$): δ 0.01 (s, 3H) 0.02 (s, 3H) 0.86 (s, 9H) 1.84-2.00 (m, 1H) 2.07-2.23 (m, 1H) 2.31-2.46 (m, 1H) 2.47-2.62 (m, 1H) 3.58-3.68 (m, 1H) 3.73-3.87 (m, 2H) 4.60 (d, J=15.92 Hz, 1H) 5.08 (d, J=15.92 Hz, 1H) 6.72 (d, J=15.55 Hz, 1H) 7.42 (s, 1H) 7.64 (d, J=15.55 Hz, 1H).

Example 73

Butyl (2E)-3-(2-{[(2R)-2-({[tert-butyl(dimethyl)silyl]oxy}methyl)-5-oxo-1-pyrrolidinyl]methyl}-1,3-thiazol-4-yl)-2-propenoate (Compound 73)

To a solution of the compound 72 (980 mg) in dimethylformamide (3.00 mL) was added n-butyl iodide (570 μL) at room temperature and then thereto was added potassium carbonate (691 mg) at 0° C. The solution was stirred at room temperature overnight. Water was added to the reaction solution, which was extracted with ethyl acetate. The organic layer was washed water and brine, dried over anhydrous sodium sulfate and concentrated. The organic residue was purified by column chromatography on silica gel (n-hexane:ethyl acetate=78:22→50:50) to give the title compound (960 mg) having the following physical data.

TLC: Rf0.60 (n-hexane:ethyl acetate=1:2);

NMR (CDCl$_3$): δ 0.01 (s, 3H) 0.02 (s, 3H) 0.86 (s, 9H) 0.96 (t, J=7.32 Hz, 3H) 1.36-1.52 (m, 2H) 1.62-1.76 (m, 2H) 1.84-1.99 (m, 1H) 2.04-2.22 (m, 1H) 2.29-2.44 (m, 1H) 2.46-2.62 (m, 1H) 3.58-3.67 (m, 1H) 3.72-3.86 (m, 2H) 4.21 (t, J=6.59 Hz, 2H) 4.57 (dd, J=15.92, 0.73 Hz, 1H) 5.07 (d, J=15.92 Hz, 1H) 6.71 (dd, J=15.50, 0.55 Hz, 1H) 7.36 (s, 1H) 7.55 (dd, J=15.50, 0.46 Hz, 1H).

Example 74

Butyl (2E)-3-(2-{[(2R)-2-(hydroxymethyl)-5-oxo-1-pyrrolidinyl]methyl}-1,3-thiazol-4-yl)-2-propenoate (Compound 74)

To a solution of the compound 73 (952 mg) in n-butanol (4.40 mL) was added 2N hydrochloric acid (2.20 mL) at room temperature and the solution was stirred at room temperature for 3 hours. The reaction solution was concentrated and azeotroped with toluene. Ethyl acetate and an aqueous saturated sodium carbonate solution were added thereto and the solution was separated. The organic layer was washed with brine, dried over anhydrous sodium sulfite and concentrated to give the title compound (710 mg) having the following physical data.

TLC: Rf0.35 (Ethyl acetate);

NMR (CDCl$_3$): δ 0.95 (t, J=7.41 Hz, 3H) 1.34-1.51 (m, 2H) 1.63-1.74 (m, 2H) 1.92-2.09 (m, 1H) 2.09-2.27 (m, 1H) 2.30-2.45 (m, 1H) 2.46-2.63 (m, 1H) 3.53-3.66 (m, 1H) 3.74-3.96 (m, 2H) 4.19 (t, J=6.68 Hz, 2H) 4.43 (d, J=15.92 Hz, 1H) 4.99 (dd, J=8.42, 5.85 Hz, 1H) 5.06 (d, J=15.92 Hz, 1H) 6.59 (dd, J=15.69, 0.46 Hz, 1H) 7.40 (t, J=0.46 Hz, 1H) 7.55 (dd, J=15.69, 0.37 Hz, 1H).

Example 75

Butyl 3-(2-{[(2R)-2-(hydroxymethyl)-5-oxo-1-pyrrolidinyl]methyl}-1,3-thiazol-4-yl)propanoate (Compound 75)

To a solution of the compound 74 (350 mg) in tetrahydrofuran (4.0 mL) and n-butanol (1.30 mL) was nickel chloride hexahydrate (246 mg) at room temperature and then thereto was added sodium borohydride (156 mg) at 0° C. The solution was stirred for 1 hour. The reaction solution was diluted with ethyl acetate and filtrated through Celite (Brand name). The obtained filtrate was washed an aqueous saturated ammonium chloride solution and brine, dried over anhydrous sodium sulfate and concentrated. The obtained residue was purified by column chromatography on silica gel (ethyl acetate:methanol=1:0→19:1) to give the title compound (244 mg) having the following physical data.

TLC: Rf0.32 (ethyl acetate:methanol=19:1);

NMR (CDCl$_3$): δ 0.92 (t, J=7.32 Hz, 3H) 1.27-1.43 (m, 2H) 1.52-1.65 (m, 2H) 1.92-2.07 (m, 1H) 2.08-2.23 (m, 1H) 2.36 (ddd, J=17.02, 10.25, 6.59 Hz, 1H) 2.53 (ddd, J=16.92, 10.34, 6.22 Hz, 1H) 2.69 (t, J=7.50 Hz, 2H) 3.05 (t, J=7.50 Hz, 2H) 3.54 (ddd, J=12.72, 8.60, 3.93 Hz, 1H) 3.71-3.79 (m, 1H) 3.84 (ddd, J=12.62, 5.76, 2.29 Hz, 1H) 4.07 (t, J=6.68 Hz, 2H) 4.32 (d, J=15.92 Hz, 1H) 5.07 (d, J=15.92 Hz, 1H) 5.56 (dd, J=8.60, 5.67 Hz, 1H) 6.92 (t, J=0.91 Hz, 1H).

Example 76

3-{2-[((2R)-2-{(1E,3R)-3-[1-(4-fluorobutyl)cyclobutyl]-3-hydroxy-1-propenyl}-5-oxo-1-pyrrolidinyl)methyl]-1,3-thiazole-4-yl}propanoic acid (Compound 76)

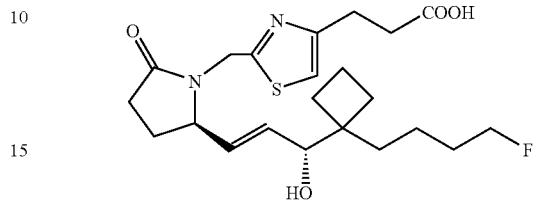

By the same procedure as a series of reactions of Example 5→Example 6→Example 7→Example 8 using the compound 75 instead of the compound 4 and using dimethyl {2-[1-(4-fluorobutyl)cyclobutyl]-2-oxoethyl}phosphonate instead of dimethyl (3,3-diethyl-2-oxoheptyl)phosphonate, the title compound having the following physical data was obtained.

TLC: Rf0.41 (methylene chloride:methanol:acetic acid=18:1:1);

NMR (CDCl$_3$): δ 1.31-2.04 (m, 13H), 2.21-2.60 (m, 3H), 2.75 (t, J=6.77 Hz, 2H), 3.05 (t, J=6.77 Hz, 2H), 4.06-4.23 (m, 2H), 4.39 (dt, J=47.30, 5.99 Hz, 2H), 4.39 (d, J=15.83 Hz, 1H), 4.92 (d, J=15.83 Hz, 1H), 5.60 (ddd, J=15.37, 8.55, 1.10 Hz, 1H), 5.80 (dd, J=15.37, 5.85 Hz, 1H), 6.93 (s, 1H).

Biological Example

It was demonstrated by e.g. the below experiment that the prostaglandin-like compound has cauda equina blood flow-increasing effect and weak blood pressure-lowering effect.

The common procedure based on the fundamental biological means was used as all procedures. Furthermore, the measuring method of the present invention was modified to improve the accuracy and/or sensitivity of measurement for evaluating the compound of the present invention. The detailed experimental method was as follows. (i) The measurement of the cauda equina blood flow and the blood pressure Experiment: 1.5 g/kg of urethane was administered intraperitoneally to the rat to be anesthetized, and the catheter, which is for measurement of blood pressure and ventricular rate, was placed in left carotid artery in supine position. The rat was reversed to prone position and the lumbar part was incised in the median line. The laminectomy was given to the fifth lumbar vertebra and the spinal cord (cauda equina) was exposed. The cauda equina blood flow was measured by the laser-Doppler flowmetry (OMEGAFLD FLO-NI and ADVANCE LASER FLOWMETER ALF21N, OMEGA WAVE Inc.) through a noncontact probe (ST-N type, OMEGA WAVE Inc.) and recorded with LINEARCORDER (Graphtech). The systemic blood pressure and the ventricular rate were measured from a left carotid artery with amplifier for the pressure measurement (GOULD) through a pressure transducer and recorded with LINEARCORDER (Graphtech).

After confirming each parameter of blood pressure, ventricular rate and blood flow was stabilized, the test compound was administrated by continuous infusion through the winged needle placed in caudal vein for 30 minutes. It observed until 30 minutes after the administration and the increase rate of the cauda equina blood flow was calculated. The increase rate of the cauda equina blood flow (%)=(B−A)/A×100

A: the cauda equina blood flow before the administration of the test compound

B: the cauda equina blood flow after the administration of the test compound

As a result, the compounds of the present invention increased the cauda equina blood flow although they had weak blood pressure-lowering effect. For instance, the compound 8-1 increased 35% of the cauda equina blood flow, while it decreased only 6 mmHg of the blood pressure. Moreover, the compound 53 increased 31% of the cauda equina blood flow, while it decreased only 10 mmHg of the blood pressure.

FORMULATION EXAMPLE

Formulation Example 1

The following components were admixed in a conventional method and punched out to obtain 10,000 tablets each containing 0.5 mg of the active ingredient.

| | |
|---|---|
| The compound 8-1 | 5.0 g |
| Carboxymethyl cellulose calcium | 20 g |
| Magnesium stearate | 10 g |
| Microcrystalline cellulose | 920 g |

Formulation Example 2

The following components were admixed in a conventional method, and the solution was sterilized in a conventional method, placed at 1 mL into vials and freeze-dried in a conventional method to thereby obtain 10,000 vials each containing 0.2 mg of the active ingredient.

| | |
|---|---|
| The compound 8-1 | 2.0 g |
| Mannitol | 500 g |
| Distilled water | 10 L |

INDUSTRIAL APPLICABILITY

The prostaglandin-like compound having weak blood pressure-lowering effect and an effect increasing cauda equina blood flow is effective for treatment for lumbago, lower limb pain, lower limb numbness, intermittent claudication, bladder and rectal disorders or sexual dysfunctions, and it is unlikely to be caused severe side effects to the general circulation. Therefore, the prostaglandin-like compound having weak blood pressure-lowering effect is useful as medicament.

The invention claimed is:

1. A compound of 2-[(2-{(1R,2R)-2-[(1E)-4-hydroxy-4-methyl-1-nonenyl]-5-oxocyclopentyl}ethyl)sulfanyl]-1,3-thiazole-4-carboxylic acid, an R-configuration or an S-configuration thereof due to the presence of an asymmetric carbon, or a salt thereof.

2. The compound according to claim 1, which is 2-[(2-{(1R,2R)-2-[(1E)-4-hydroxy-4-methyl-1-nonenyl]-5-oxocyclopentyl}ethyl)sulfanyl]-1,3-thiazole-4-carboxylic acid or a salt thereof.

3. The compound according to claim 1, which is
   the R-configuration of 2-[(2-{(1R,2R)-2-[(1E)-4-hydroxy-4-methyl-1-nonenyl]-5-oxocyclopentyl}ethyl)sulfonyl]-1,3-thiazole-4-carboxylic acid or a salt thereof.

4. The compound according to claim 1, which is
   the S-configuration of 2-[(2-{(1R,2R)-2-[(1E)-4-hydroxy-4-methyl-1-nonenyl]-5-oxocyclopentyl}ethyl)sulfanyl]-1,3-thiazole-4-carboxylic acid or a salt thereof.

\* \* \* \* \*